US007345065B2

(12) United States Patent
Gil et al.

(10) Patent No.: US 7,345,065 B2
(45) Date of Patent: Mar. 18, 2008

(54) METHODS AND COMPOSITIONS FOR ALLEVIATING PAIN

(75) Inventors: Daniel W. Gil, Corona Del Mar, CA (US); John E. Donello, Dana Point, CA (US)

(73) Assignee: Allergan, Inc., Irvine, CA (US)

( * ) Notice: Subject to any disclaimer, the term of this patent is extended or adjusted under 35 U.S.C. 154(b) by 606 days.

(21) Appl. No.: 10/153,154

(22) Filed: May 21, 2002

(65) Prior Publication Data

US 2003/0229088 A1 Dec. 11, 2003

(51) Int. Cl.
*A61K 31/425* (2006.01)
*A31K 31/17* (2006.01)
(52) U.S. Cl. .................................. 514/365; 514/587
(58) Field of Classification Search ............... 514/365, 514/587
See application file for complete search history.

(56) References Cited

U.S. PATENT DOCUMENTS

| 5,021,410 A | 6/1991 | Burke ........................ 514/213 |
| 6,313,172 B1 * | 11/2001 | Chow et al. ................ 514/587 |
| 6,329,369 B1 * | 12/2001 | Chow et al. ............. 514/230.5 |

FOREIGN PATENT DOCUMENTS

| WO | WO 99/28300 | 6/1999 |
| WO | WO 01/00586 | 1/2001 |
| WO | WO 01/78702 | 10/2001 |
| WO | WO 01/78703 | 10/2001 |

OTHER PUBLICATIONS

Al-Chaer et al., "A new model of chronic visceral hypersensitivity in adult rats induced by colon irritation during postnatal development," *Gastroenterology* 119:1276-1285 (2000).
Altman et al., "Abnormal regulation of the sympathetic nervous system in $\alpha_2$-adrenergic receptor knockout mice," *Mol. Pharm.* 56:154-161 (1999).
Beeley et al., "Synthesis of a selective alpha-2A adrenoceptor antagonist, BRL 48962, and its characterization at cloned human alpha-adrenoceptors," *Bioorganic & Med. Chem.* 3:1693-1698 (1995).
Bennett and Xie, "A peripheral mononeuropathy in rat that produces disorders of pain sensation like those seen in man," *Pain* 33:87-107 (1988).
Boucher et al., "Potent analgesic effects of GDNF in neuropathic pain states," *Science* 290:124-127 (2000).

(Continued)

*Primary Examiner*—San-Ming Hui
(74) *Attorney, Agent, or Firm*—Joel B. German; Martin A. Voet; Stephen Donovan

(57) ABSTRACT

The present invention provides a method for the long-term relief of chronic pain in a subject by activating in the subject an analgesic $\alpha$-adrenergic receptor in the absence of $\alpha$-2A receptor activation over a period of at least three days, such that relief of chronic pain is maintained in the absence of continued activation of said receptor. The analgesic $\alpha$-adrenergic receptor can be, for example, the $\alpha$-2B receptor.

60 Claims, 15 Drawing Sheets

OTHER PUBLICATIONS

Bylund et al., "International Union of Pharmacology nomenclature of adrenoceptors," *Pharmacol. Rev.*, 46:121-136 (1994).

Calzada and Artiñano, "Alpha-adrenoceptor subtypes," *Pharm. Res.* 44:195-208 (2001).

Conklin et al., "Substitution of three amino acids switches receptor specificity of Gq alpha to that of Gi alpha," *Nature* 363:274-276 (1993).

Dixon et al., "Efficient analysis of experimental observations," *Ann. Rev. Pharmacol. Toxicol.* 20:441-462 (1980).

Dray, "Neurogenic mechanisms and neuropeptides in chronic pain," *Progress in Brain Res.* 110:85-94 (1996).

Hein and Kobilka, "Adrenergic receptor signal transduction and regulation," *Neuropharmacol.* 34:357-366 (1995).

Hein et al., "Gene substitution/knockout to delineate the role of $\alpha_2$-adrenoceptor subtypes in mediating central effects of catecholamines and imidazolines," *Ann. NY Acad. Science* 881:265-271 (1999).

Hieble et al., "$\alpha$- and $\beta$-adrenoceptors: from the gene to the clinic. 1. Molecular biology and adrenoceptor subclassification," *J. Med. Chem.* 38:3415-3444 (1995).

Kable et al., "In vivo gene modification elucidates subtype-specific functions of $\alpha_2$-adrenergic receptors," *J. Pharm. Exper. Ther.* 293:1-7 (2000).

Kamibayashi and Maze, "Clinical uses of $\alpha_2$-adrenergic agonists," *Anesthesiology* 93:1345-1349 (2000).

Kim and Chung, "An experimental model for peripheral neuropathy produced by segmental spinal nerve ligation in the rat," *Pain* 50:355-363 (1992).

Maze and Fujinaga, "$\alpha_2$ adrenoceptors in pain modulation," *Anesthesiology* 92:934-936 (2000).

Messier et al., "High throughput assays of cloned adrenergic, muscarinic, neurokinin, and neurotrophin receptors in living mammalian cells," *Pharmacol. Toxicol.* 76:308-311 (1995).

Minami et al., "Allodynia evoked by intrathecal administration of prostaglandin E2 to conscious mice," *Pain* 57:217-223 (1994).

Myers, "The pathogenesis of neuropathic pain," *Regional Anesthesia* 20:173-184 (1995) 1994 ASRA Lecture.

Roberts et al., "SK&F 104078, a post-junctionally selective $\alpha_2$-adrenoceptor antagonist in the human saphenous vein in vitro," *Arch. Pharmacol.* 345:327-332 (1992).

Wang et al., "Antisense RNA/DNA-based techniques to probe adrenergic receptor function," *Meth. Mol. Biol.* 126:241-258 (2000).

Woolf and Mannion, "Neuropathic pain: Aetiology, symptoms, mechanisms, and management," *The Lancet* 353:1959-1964 (1999).

Woolf and Salter, "Neuronal plasticity: Increasing the gain in pain," *Science* 288:1765-1768 (2000).

Yaksh, "Spinal systems and pain processing: Development of novel analgesic drugs with mechanistically defined models," *Trends Pharmacol. Science* 8:329-337 (1999).

Yaksh and Harty, "Pharmacology of the allodynia in rats evoked by high dose intrathecal morphine," *J. Pharmacology Exp. Ther.* 244:501-507 (1988).

Young et al., "Novel $\alpha_2$-adrenoceptor antagonists show selectivity for $\alpha_{2A}$- and $\alpha_{2B}$-adrenoceptor subtypes," *Eur. J. of Pharmacol.* 168:381-386 (1989).

* cited by examiner

METHODS AND COMPOSITIONS FOR ALLEVIATING PAIN

BACKGROUND OF THE INVENTION

1. Field of the Invention

This invention relates generally to the treatment of pain and the long-term reversal of chronic pain and, in particular, to α-adrenergic agonists, and selective antagonists of the α-2A adrenergic receptor.

2. Background Information

Clinical pain encompasses nociceptive and neuropathic pain. Each type of pain is characterized by hypersensitivity at the site of damage and in adjacent normal tissue. While nociceptive pain usually is limited in duration and responds well to available opioid therapy, neuropathic pain can persist long after the initiating event has healed, as is evident, for example, in the "ghost pain" that often follows amputation. Chronic pain syndromes such as chronic neuropathic pain are triggered by any of a variety of insults, including surgery, compression injury or trauma, infectious agent, toxic drug, inflammatory disorder, or a metabolic disease such as diabetes or ischemia.

Unfortunately, chronic pain such as chronic neuropathic pain generally is resistant to available drug therapy. Furthermore, current therapies have serious side-effects such as cognitive changes, sedation, nausea and, in the case of narcotic drugs, addiction. Many patients suffering from neuropathic and other chronic pain are elderly or have medical conditions that limit their tolerance to the side-effects associated with available analgesic therapy. The inadequacy of current therapy in relieving neuropathic pain without producing intolerable side-effects often is manifest in the depression and suicidal tendency of chronic pain sufferers.

α-2 adrenergic agonists, which are devoid of respiratory depressant effects and addictive potential, are being developed as alternatives to current analgesics. Such drugs are useful analgesic agents when administered spinally. However, undesirable pharmacological properties of α-adrenergic agonists, specifically sedation and hypotension, limit the utility of these drugs when administered orally or by other peripheral routes. Thus, there is a need for effective analgesic agents that can be administered by oral or other peripheral routes and that lack undesirable side-effects such as sedation and hypotension. The present invention satisfies this need and provides related advantages as well.

The present invention also provides new therapy for chronic pain sufferers, who, until now, have faced a lifetime of daily medication to control their pain. Unfortunately, available treatments for chronic neuropathic pain, such as tricyclic antidepressants, anti-seizure drugs and local anesthetic injections, only alleviate symptoms temporarily and to varying degrees. No available treatment reverses the sensitized pain state or cures pain such as neuropathic pain. Effective drugs that can be administered, for example, once or several times a month and that maintain analgesic activity for several weeks or months, are presently not available. Thus, there is a need for novel methods of providing long-term relief from chronic pain. The present invention satisfies this need and also provides related advantages.

SUMMARY OF THE INVENTION

The present invention provides a method of alleviating pain in a subject by administering to the subject a pharmaceutical composition containing an effective amount of an α-adrenergic agonist and a pharmaceutical composition containing an effective amount of a selective α-2A antagonist. The methods of the invention are useful for alleviating a variety of types of pain including, but not limited to, neuropathic pain such as the pain resulting from diabetic neuropathy; visceral pain; post-operative pain; pain resulting from cancer or cancer treatment; inflammatory pain resulting, for example, from arthritis or irritable bowel syndrome; headache pain and muscle pain.

A variety of α-adrenergic agonists are useful in the invention including pan-α-2 agonists and pan-α-1 pan-α-2 agonists. α-adrenergic agonists useful in alleviating pain according to a method of the invention include, without limitation, clonidine, brimonidine, tizanidine, dexemedetomidine, norepinephrine, Compound 1 and Compound 2, and all pharmaceutically acceptable salts, esters, amides, sterioisomers and racemic mixtures thereof.

A variety of selective α-2A antagonists also are useful in the invention. Such selective α-2A antagonists include, without limitation, 4-imidazoles such as Compound 13 and pharmaceutically acceptable salts, esters, amides, sterioisomers and racemic mixtures thereof, and BRL 48962 or pharmaceutically acceptable salts, esters, amides, sterioisomers and racemic mixtures thereof. In one embodiment, the invention is practiced with a peripherally limited selective α-2A antagonist.

Various routes of administration can be useful for alleviating pain according to a method of the invention. In one embodiment, both the α-adrenergic agonist and selective α-2A antagonist are administered peripherally. In other embodiments, the α-adrenergic agonist is administered orally or through a subcutaneous minipump. In further embodiments, the α-adrenergic agonist is administered orally or through a subcutaneous minipump, and the selective α-2A antagonist is administered by any peripheral route. In yet other embodiments, the selective α-2A antagonist is administered orally or through a subcutaneous minipump. If desired, the selective α-2A antagonist can be administered orally or through a subcutaneous minipump, and the α-adrenergic agonist can be administered by any peripheral route such as orally or through a subcutaneous minipump.

In one embodiment, the invention provides a method of alleviating pain in a subject by administering to the subject a pharmaceutical composition containing an effective amount of an α-adrenergic agonist and a pharmaceutical composition containing an effective amount of a selective α-2A antagonist, where the α-adrenergic agonist and the selective α-2A antagonist each is administered repeatedly or continuously over a period of at least three days. In such a method, pain alleviation can continue, for example, in the absence of significant α-adrenergic agonist levels in the subject.

The present invention further provides an analgesic composition that contains an α-adrenergic agonist with minimal α-2A agonist activity having the ability to produce peripheral analgesia without concomitant sedation. In one embodiment, the analgesic composition produces peripheral analgesia without concomitant sedation and in the substantial absence of hypotensive effects. In another embodiment, the invention provides an analgesic composition that produces peripheral analgesia sufficient to reduce pain by at least 50% without concomitant sedation. In further embodiments, at least a 10-fold, 100-fold or 1000-fold greater dose of the analgesic composition is required to produce a 20% reduction in motor or muscular activity than the dose of the analgesic composition that reduces pain by at least 50%. In a further embodiment, the invention provides an analgesic composition that produces peripheral analgesia sufficient to reduce pain by at least 50% without concomitant sedation and in the substantial absence of hypotensive effects. In another embodiment, the invention provides an analgesic composition that contains an α-adrenergic agonist with minimal α-2A agonist activity having the ability to produce peripheral analgesia without concomitant sedation, where the agonist is not a thiourea or derivative thereof. In a further embodiment, the invention provides an analgesic composition that contains an α-adrenergic agonist with minimal α-2A agonist activity having the ability to produce peripheral analgesia without concomitant sedation, where the agonist is not a thiourea or 4-imidazole or derivative thereof.

Further provided by the invention is a method of alleviating pain in a subject by peripherally administering to the subject a pharmaceutical composition containing an effective amount of an α-adrenergic agonist with minimal α-2A agonist activity, thereby producing peripheral analgesia without concomitant sedation. Such peripheral analgesia can be sufficient to reduce pain, for example, by at least 50% without concomitant sedation. In another embodiment, the peripheral analgesia occurs in the substantial absence of hypotensive effects. In one embodiment, the method is practiced using an α-adrenergic agonist with minimal α-2A agonist activity which is not a thiourea or derivative thereof. In another embodiment, the method is practiced using an α-adrenergic agonist with minimal α-2A agonist activity which is not a thiourea or 4-imidazole or derivative thereof. Pain of various types and etiologies can be alleviated according to a method of the invention. As non-limiting examples, the methods of the invention can be useful in alleviating neuropathic pain, such as the pain resulting from diabetic neuropathy; visceral pain; post-operative pain; pain resulting from cancer or cancer treatment; inflammatory pain such as arthritic pain or irritable bowel syndrome pain; headache pain and muscle pain.

A variety of α-adrenergic agonists with minimal α-2A agonist activity can be useful in the methods of the invention. In one embodiment, the α-adrenergic agonist with minimal α-2A agonist activity is an α-2B agonist with minimal α-2A agonist activity. Such an agonist can be, for example, a thione such as Compound 3 or Compound 11 or a pharmaceutically acceptable salt, ester, amide, sterioisomer or racemic mixture thereof. In one embodiment, a method of the invention is practiced with an α-2B agonist with minimal α-2A agonist activity which is the (−) enantiomer of Compound 3 or a pharmaceutically acceptable salt or ester thereof.

α-2B agonists with minimal α-2A agonist activity useful in the invention further include, but are not limited to, imidazolones. A useful imidazolone α-2B agonist with minimal α-2A agonist activity can be, for example, Compound 4 or a pharmaceutically acceptable salt, ester, amide, sterioisomer or racemic mixture thereof. In one embodiment, the α-2B agonist with minimal α-2A agonist activity is the (+) enantiomer of Compound 4 or a pharmaceutically acceptable salt, ester or amide thereof. In additional embodiments, a method of the invention is practiced using one of the following α-2B agonists with minimal α-2A agonist activity: Compound 5, Compound 6, Compound 7, Compound 8, Compound 9 or Compound 14, or a pharmaceutically acceptable salt, ester, amide, sterioisomer or racemic mixture thereof. An α-adrenergic agonist with minimal α-2A agonist activity can be peripherally administered by any of a variety of routes including, without limitation, oral administration and administration via subcutaneous minipump.

The present invention also provides a method of screening for effective agents that produce peripheral analgesia without concomitant sedation by contacting an α-2A receptor with an α-adrenergic agonist having analgesic activity; and determining whether the agonist has α-2A agonist activity, where the absence of α-2A agonist activity indicates that the α-adrenergic agonist having analgesic activity is an effective agent that produces peripheral analgesia without concomitant sedation.

Further provided herein is a method of screening for effective agents that produce peripheral analgesia without concomitant sedation by contacting an α-2A receptor with an agent; determining whether the agent has α-2A agonist activity; contacting an α-2B receptor with the agent; and determining whether the agent has α-2B agonist activity, where the absence of α-2A agonist activity and the presence of α-2B agonist activity indicate that the agent is an effective agent that produces peripheral analgesia without concomitant sedation.

The invention also provides a method of screening for effective agents that produce peripheral analgesia without concomitant sedation by peripherally administering an α-adrenergic agonist to a control animal having at least wild type levels of α-2A receptor activity; assaying for analgesia in the control animal; peripherally administering to a corresponding animal having reduced levels of α-2A receptor expression or activity an amount of the α-adrenergic agonist similar or greater than the amount administered to the control animal; and assaying for analgesia in the corresponding animal having reduced levels of α-2A receptor expression or activity, where the absence of analgesia in the control animal and the presence of analgesia in the corresponding animal having reduced levels of α-2A receptor expression or activity indicate that the α-adrenergic agonist has excessive α-2A agonist activity, and where the presence of analgesia in the control animal and the presence of analgesia in the corresponding animal having reduced levels of α-2A receptor expression or activity indicate that the α-adrenergic agonist is an effective agent that produces peripheral analgesia without concomitant sedation. In such a method of the invention, the control animal can be, for example, wild type at both α-2A receptor loci. In one embodiment, the control animal is a wild type animal such as a wild type mouse. A variety of corresponding animals are useful in a screening method of the invention. In one embodiment, the invention is practiced with a corresponding animal having a homozygous point mutation at the α-2A receptor locus. In another embodiment, the invention is practiced with a corresponding animal having a point mutation within the α-2A receptor coding sequence. Such a point mutation can occur, for example, at a residue analogous to Asp79 and can be, for example, an Asp79 to Asn mutation. In a further embodiment, the invention is practiced with a corresponding animal having a homozygous α-2A knockout mutation. It is understood that a variety of methodologies can be used to assay for analgesia in the methods of the invention, including, but not limited to, assaying for analgesia following sulprostone sensitization.

If desired, a method of the invention for screening for effective agents that produce peripheral analgesia without concomitant sedation can be practiced by (a) peripherally administering an α-adrenergic agonist to a control animal having at least wild type levels of α-2A and α-2B receptor activity; (b) assaying for analgesia in the control animal; (c) peripherally administering to a corresponding animal having reduced levels of α-2A receptor expression or activity an amount of the α-adrenergic agonist similar or greater than the amount administered to the control animal; (d) assaying for analgesia in the corresponding animal having reduced levels of α-2A receptor expression or activity; (e) peripherally administering the α-adrenergic agonist to a corresponding animal having reduced levels of α-2B receptor expression or activity; and (f) assaying for analgesia in the corresponding animal having reduced levels of α-2B receptor expression or activity, where the absence of analgesia in the control animal and the presence of analgesia in the corresponding animal having reduced levels of α-2A receptor expression or activity indicate that the α-adrenergic agonist has excessive α-2A agonist activity, and where the presence of analgesia in the control animal, the presence of analgesia in said corresponding animal having reduced levels of α-2A receptor expression or activity, and the absence of analgesia in the corresponding animal having reduced levels of α-2B receptor expression or activity indicate that the α-adrenergic agonist is an effective agent that produces peripheral analgesia without concomitant sedation.

The present invention additionally provides a method of screening for effective agents that produce peripheral analgesia without concomitant sedation by peripherally administering an α-adrenergic agonist to a control animal having at least wild type levels of α-2B receptor activity; assaying for analgesia in the control animal; peripherally administering the α-adrenergic agonist to a corresponding animal having reduced levels of α-2B receptor expression or activity; and assaying for analgesia in the corresponding animal having reduced levels of α-2B receptor expression or activity, where the presence of analgesia in the control animal and the absence of analgesia in the corresponding animal having reduced levels of α-2B receptor expression or activity indicate that the α-adrenergic agonist is an effective agent that produces peripheral analgesia without concomitant sedation.

Such a method of the invention can be practiced with a variety of control animals, for example, a control animal which is wild type at both α-2B receptor loci. In one embodiment, the control animal is a wild type animal. In a further embodiment, the control animal is a wild type mouse. Similarly, a variety of corresponding animals are useful in the screening methods of the invention, including corresponding animals which have a heterozygous α-2B knockout mutation or a homozygous α-2B knockout mutation. Analgesia can be assayed using any of a variety of methodologies. In one embodiment, analgesia is assayed following sulprostone sensitization.

The present invention further provides a method for the long-term relief of chronic pain in a subject. The method is practiced by activating in the subject an analgesic α-adrenergic receptor in the absence of α-2A receptor activation over a period of at least three days, such that relief of chronic pain is maintained in the absence of continued receptor activation. In one embodiment, a method of the invention is practiced by administering to the subject a pharmaceutical composition containing an effective amount of an α-adrenergic agonist with minimal α-2A agonist activity over a period of at least three days, such that relief of chronic pain is maintained in the absence of significant agonist levels in the subject. Relief of chronic pain can be maintained, for example, for at least three weeks in the absence of significant agonist levels in the subject. It is understood that the methods of the invention can be used for the long-term relief of any type of chronic pain. As non-limiting examples, such a method can be used for the long-term relief of neuropathic pain; visceral pain; post-operative pain; pain resulting from cancer or cancer treatment; or inflammatory pain.

Long-term chronic pain relief can be achieved according to a method of the invention with any of a variety of α-adrenergic agonists with minimal α-2A agonist activity. Long-term chronic pain relief can be achieved, for example, using an α-2B agonist with minimal α-2A agonist activity. Exemplary α-2B agonists with minimal α-2A agonist activity include, without limitation, thiones such as Compound 3 or Compound 11, or pharmaceutically acceptable salts, esters, amides, sterioisomers or racemic mixtures thereof. In one embodiment, such a thione α-2B agonist with minimal α-2A agonist activity is the (−) enantiomer of Compound 3, or a pharmaceutically acceptable salt or ester thereof. Exemplary α-2B agonists with minimal α-2A agonist activity further include, without limitation, imidazolones such as Compound 4 or a pharmaceutically acceptable salt, ester, amide, sterioisomer or racemic mixture thereof. In one embodiment, such a imidazolone α-2B agonist with minimal α-2A agonist activity is the (+) enantiomer of Compound 4, or a pharmaceutically acceptable salt or ester thereof. Exemplary α-2B agonists with minimal α-2A agonist activity also include, without limitation, compounds such as Compound 5, Compound 6, Compound 7, Compound 8 and Compound 9, and pharmaceutically acceptable salts, esters, amides, sterioisomers and racemic mixtures thereof. An α-adrenergic agonist with minimal α-2A agonist activity can be administered by any of a variety of routes including, but not limited to, all routes of peripheral administration, for example, oral administration or administration via subcutaneous minipump.

In a further embodiment, a method of the invention is practiced by administering to the subject a pharmaceutical composition containing an effective amount of an α-adrenergic agonist and a pharmaceutical composition containing an effective amount of a selective α-2A antagonist over a period of at least three days, such that relief of chronic pain is maintained in the absence of significant agonist levels in the subject. Chronic pain relief can be maintained, for example, for at least three weeks in the absence of significant agonist levels in the subject. A variety of α-adrenergic agonists are useful in the invention including clonidine, brimonidine, tizanidine, dexemedetomidine, norepinephrine and other pan-α-2 agonists and pan-α-1 pan-α-2 agonists as well as Compound 1 or Compound 2, and pharmaceutically acceptable salts, esters, amides, sterioisomers and racemic mixtures thereof. Similarly, a variety of selective α-2A antagonists are useful in long-term relief of chronic pain including, without limitation, Compound 13 and pharmaceutically acceptable salts, esters, amides, sterioisomers and racemic mixtures thereof, and peripherally limited selective α-2A antagonists.

Various routes of administration can be useful for delivering pharmaceutical compositions for the long-term relief of chronic pain. Such routes of administration encompass, but are not limited to, peripheral administration, for example, oral administration or administration via subcutaneous minipump. In one embodiment, the α-adrenergic agonist and selective α-2A antagonist both are administered peripherally. In other embodiments, the α-adrenergic agonist is administered orally or through a subcutaneous minipump, and the selective α-2A antagonist is administered by any peripheral route. In still further embodiments, the selective α-2A antagonist is administered orally or through a subcutaneous minipump and the α-adrenergic agonist is administered by a peripheral route, including but not limited to, orally or via subcutaneous minipump.

DETAILED DESCRIPTION OF THE INVENTION

Figure 1:
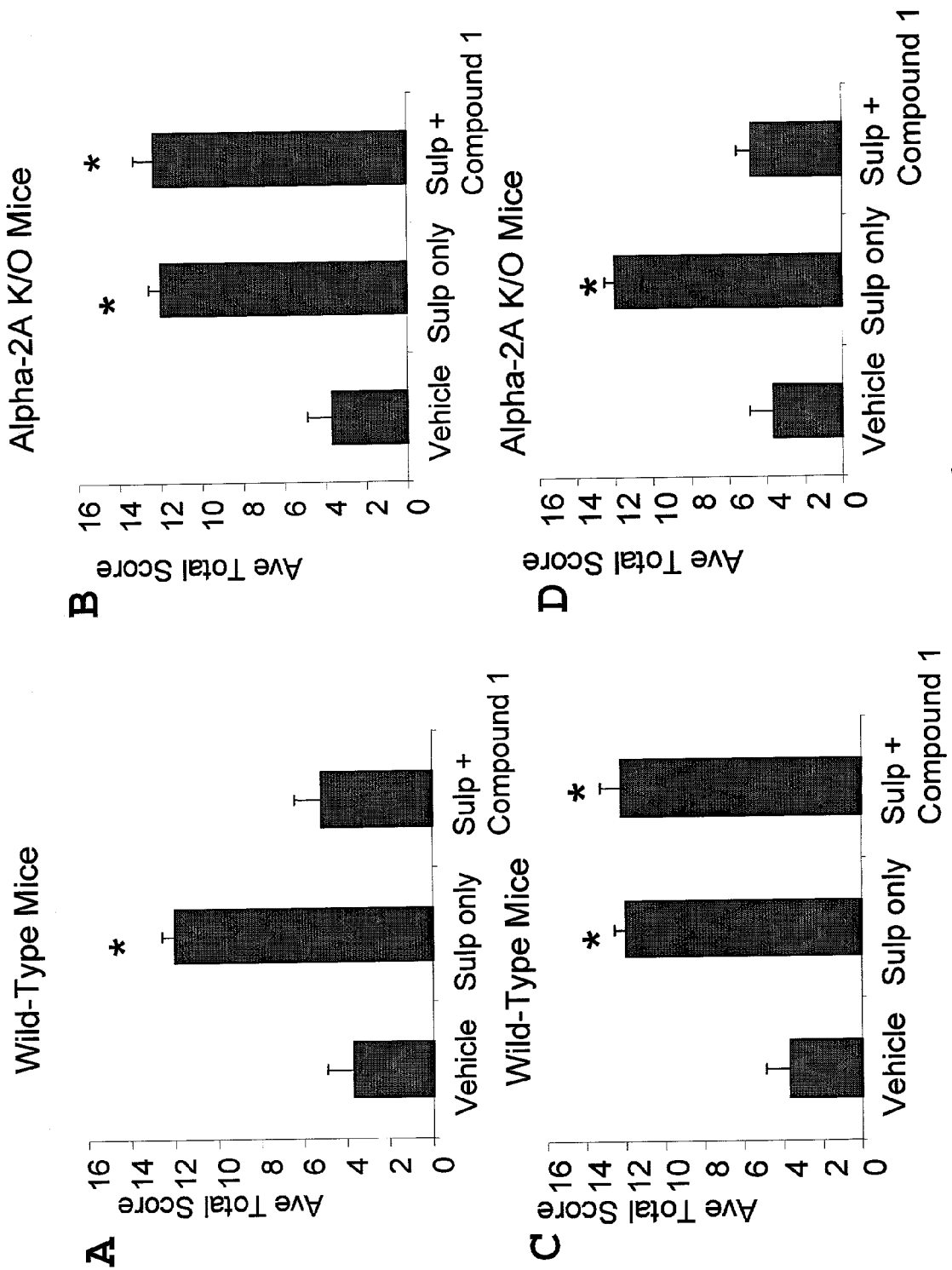
FIG. 1 shows the results obtained with intrathecal (1 μg) or intraperitoneal (30 μg/kg) injection of Compound 1 into sulprostone-sensitized wild type or α-2A knockout animals. Pain sensitivity to light touch was scored as described below. (A) Intrathecal injection into wild type mice. (B) Intrathecal injection into α-2A knockout mice. (C) Intraperitoneal injection into wild type mice. (D) Intraperitoneal injection into α-2A knockout mice. Asterisks indicate a significant result with a p value <0.05.

Adrenergic receptors mediate physiological responses to the catecholamines, norephinephrine and epinephrine, and are members of the superfamily of G protein-coupled receptors having seven transmembrane domains. These receptors, which are divided pharmacologically into α-1, α-2 and α-adrenergic receptor types, are involved in diverse physiological functions including functions of the cardiovascular and central nervous systems. The α-adrenergic receptors mediate most excitatory functions: α-1 adrenergic receptors generally mediate responses in the effector organ, while α-2 adrenergic receptors are located postsynaptically as well as presynaptically, where they regulate release of neurotransmitters. Agonists of α-2 adrenergic receptors currently are used clinically in the treatment of hypertension, glaucoma, spasticity, and attention-deficit disorder, in the suppression of opiate withdrawal, and as adjuncts to general anesthesia.

The α-2 adrenergic receptors presently are classified into three subtypes based on their pharmacological and molecular characterization: α-2A/D (α-2A in human and α-2D in rat); α-2B; and α-2C (Bylund et al., *Pharmacol. Rev.* 46:121-136 (1994); and Hein and Kobilka, *Neuropharmacol.* 34:357-366 (1995)). The α-2A and α-2B subtypes can regulate arterial contraction in some vascular beds, and the α-2A and α-2C subtypes mediate feedback inhibition of norepinephrine release from sympathetic nerve endings. The α-2A subtype also mediates many of the central effects of α-2 adrenergic agonists (Calzada and Artinano, *Pharmacol. Res.* 44: 195-208 (2001); Hein et al., *Ann. NY Acad. Science* 881:265-271 (1999); and Karger (Ed.), α-*Adrenoreceptors: Molecular Biology, Biochemistry and Pharmacology* (1991)).

Although non-selective α-adrenergic agonists having α-2A agonist activity, such as clonidine and dexmeditomidine, have been used for the treatment of various types of pain, such drugs must be administered spinally to achieve analgesia that is separable from sedation. The central analgesic effect of such pan-agonists is mediated by the α-2A receptor expressed in the dorsal horn within the spinal column. The present invention is based on the surprising discovery that, in contrast to the pro-analgesic function of the α-2A receptor in the spinal column, a peripheral α-2A receptor mediates pain. The invention further is based on identification of a peripherally expressed adrenergic receptor, the α-2B receptor, which, when activated, can produce peripheral analgesia.

As disclosed herein, α-adrenergic agonists with α-2A activity such as the pan-agonists clonidine or brimonidine produce no significant analgesia separable from sedation upon peripheral administration to wild type animals. However, analgesia separable from sedation was observed in α-2A knockout mice treated peripherally with these drugs. Furthermore, analgesic activity separable from sedation also was observed in α-2A knockout mice following peripheral administration of α-adrenergic agonists that do not readily cross the blood-brain barrier, such as Compound 1 or para-amino-clonidine (PAC; see Example IIB and FIG. 1D). This peripheral analgesic activity was not observed in wild type animals (FIG. 1C), indicating that a novel analgesic activity of α-adrenergic agonists is unmasked by preventing activation of a peripheral α-2A receptor.

Furthermore, as shown herein in Example III, Chung rats, a well-accepted model of peripheral neuropathy, were peripherally administered an α-2 pan-agonist such as clonidine together with the selective α-2A antagonist, Compound 13, shown in Table 1. In contrast to the results obtained when clonidine was peripherally administered alone, peripheral co-administration of clonidine with the selective α-2A antagonist produced an analgesic effect separable from sedation, confirming that blockade of the α-2A receptor can reveal a peripheral analgesic activity of α-adrenergic agonists in genetically unaltered animals (see FIG. 4A).

TABLE 1

Structures of Various alpha-Adrenergic Agonists and Antagonists

COMPOUND

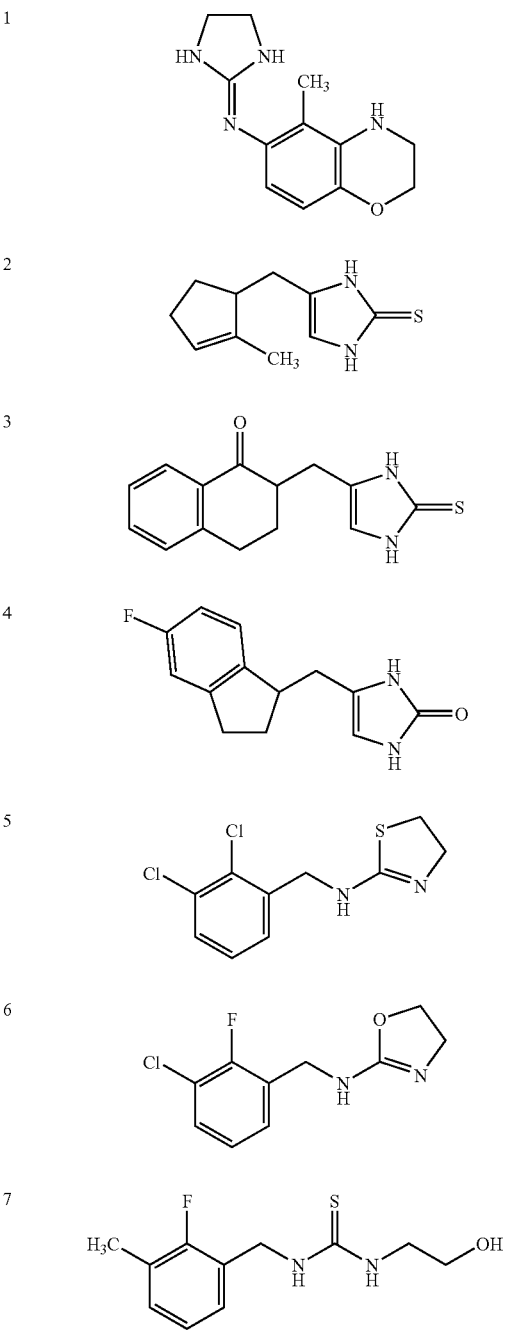

TABLE 1-continued

Structures of Various alpha-Adrenergic Agonists and Antagonists

| COMPOUND | |
|---|---|
| 8 | Cl—(C6H3)(F)—CH2—NH—C(=S)—NH—CH2CH2—OH |
| 9 | Et-cyclohexenyl-CH2-imidazole |
| 10 | tetralone-CH-(imidazole-2-thione) (−) optically pure |
| 11 | cyclopentenyl-CH2-(imidazole-2-thione) |
| 12 | F-indanyl-CH-(imidazol-2-one) (+) optically pure |
| 13 | tetrahydrobenzothiophene-CH2-imidazole |
| 14 | Br,F-phenyl-CH2-NH-(oxazoline) |

As further disclosed herein in Example III, diverse structural classes of α-adrenergic agonists with minimal α-2A activity, such as Compounds 3, 4, 5, 6, 7 and 14, produced analgesia without concomitant sedation when administered by intraperitoneal injection to Chung model rats (see Table 2 below). These results demonstrate that the analgesic activity of α-adrenergic agonists with minimal α-2A agonist activity is distinct from the previously described analgesic activity of α-adrenergic agents and further indicate that α-adrenergic agonists characterized by having minimal α-2A agonist activity can be useful peripheral analgesic drugs.

The results disclosed herein in Example IV further demonstrate that α-adrenergic agonists with minimal α-2A agonist activity can produce long-term pain relief lasting for at least six weeks following several days of drug administration. As disclosed herein, Chung model animals were treated for three to seven days using a subcutaneous osmotic minipump with Compound 8, Compound 9, Compound 3 or Compound 4, which are structurally diverse α-adrenergic agonists with minimal α-2A agonist activity. Pain relief was observed during the period of drug treatment; for example, Compound 8 alleviated allodynia 90-100%, and Compound 9 alleviated allodynia 60-80%. Furthermore, the analgesic effects of each of the agonists tested continued for over a month after treatment was concluded, and this long-term pain relief was not a property of a variety of other analgesic agents tested.

As further disclosed herein, sampling of plasma concentrations of Compound 8 at various time points revealed that very low drug levels were present by day 10 following initiation of drug treatment, and no plasma drug was detectable by day 14 (see FIG. 5B), although pain was largely alleviated at this time. In addition, the α-2 antagonist, rauwolscine, was assayed for the ability to inhibit the analgesic activity of Compound 8 at various time points following several days of dosing by oral gavage or osmotic minipump. Notably, rauwolscine inhibited the analgesic activity of Compound 8 on the third day of treatment but not on the fourth day (see FIG. 6). In sum, these results indicate that the duration of analgesic activity extends beyond the time drug remains in the blood and that, following extended dosing, α-adrenergic agonists with minimal α-2A agonist activity can provide prolonged pain relief even in the absence of continued receptor activation or plasma drug levels.

Additional results disclosed herein show that α-adrenergic agonists with minimal α-2A agonist activity also produce long-term pain relief in the Bennett partial sciatic nerve ligation model and in an animal model of irritable bowel syndrome (see Example IV, FIG. 7B and FIG. 8), demonstrating that the observed long-term analgesic effects are not specific to neuropathic pain. These results indicate that an α-adrenergic agonist with minimal α-2A agonist activity can be used to treat a variety of types of acute and chronic pain including, but not limited to, neuropathic pain, visceral pain, inflammatory pain, post-surgical pain and cancer pain.

Based on these findings, the present invention provides a method of alleviating pain in a subject by agonizing a peripheral α-adrenergic receptor other than the α-2A receptor. In one embodiment, the invention provides a method of alleviating pain in a subject by agonizing a peripheral α-2B receptor. The present invention also provides a method of alleviating pain in a subject by administering to the subject a pharmaceutical composition containing an effective amount of an α-adrenergic agonist and a pharmaceutical composition containing an effective amount of a selective α-2A antagonist. Such methods are useful for alleviating a variety of types of pain including, but not limited to, neuropathic pain such as the pain resulting from diabetic neuropathy; visceral pain; post-operative pain; pain resulting from cancer or cancer treatment; inflammatory pain resulting, for example, from arthritis or irritable bowel syndrome; headache pain and muscle pain.

A variety of α-adrenergic agonists are useful in the invention including pan-α-2 agonists and pan-α-1 pan-α-2 agonists as well as α-2B agonists. α-adrenergic agonists useful in alleviating pain according to a method of the invention encompass, without limitation, clonidine, brimonidine, tizanidine, dexemedetomidine, norepinephrine, Compound 1 and Compound 2, and all pharmaceutically acceptable salts, esters, amides, sterioisomers and racemic mixtures thereof.

A variety of selective α-2A antagonists also are useful in the invention. Such selective α-2A antagonists include, without limitation, Compound 13 and pharmaceutically acceptable salts, esters, amides, sterioisomers and racemic mixtures thereof, and BRL 48962 and BRL 44408 and pharmaceutically acceptable salts, esters, amides, sterioisomers and racemic mixtures thereof (Young et al., *Eur. J. Pharmacol.* 168:381-386 (1989)). In one embodiment, the invention is practiced with a peripherally limited selective α-2A antagonist.

Various routes of administration can be useful for alleviating pain according to a method of the invention. In one embodiment, both the α-adrenergic agonist and selective α-2A antagonist are administered peripherally. In other embodiments, the α-adrenergic agonist is administered orally or through a subcutaneous minipump. In further embodiments, the α-adrenergic agonist is administered orally or through a subcutaneous minipump, and the selective α-2A antagonist is administered by any peripheral route. In yet other embodiments, the selective α-2A antagonist is administered orally or through a subcutaneous minipump. If desired, the selective α-2A antagonist can be administered orally or through a subcutaneous minipump while the α-adrenergic agonist is administered peripherally, for example, orally or via subcutaneous minipump.

The invention also provides a method of alleviating pain in a subject by administering to the subject a pharmaceutical composition containing an effective amount of an α-adrenergic agonist and a pharmaceutical composition containing an effective amount of a selective α-2A antagonist, where the α-adrenergic agonist and the selective α-2A antagonist each is administered repeatedly or continuously over a period of at least three days. In such a method, pain alleviation can continue, for example, in the absence of significant α-adrenergic agonist levels in the subject.

The present invention provides methods that rely on administration of one or more pharmaceutical compositions to a subject. As used herein, the term "subject" means any animal capable of experiencing pain, for example, a human or other mammal such as a primate, horse, cow, dog or cat.

The methods of the invention are used to treat both acute and chronic pain, and, as non-limiting examples, pain which is neuropathic, visceral or inflammatory in origin. In particular embodiments, the methods of the invention are used to treat neuropathic pain; visceral pain; post-operative pain; pain resulting from cancer or cancer treatment; and inflammatory pain.

Both acute and chronic pain can be treated by the methods of the invention, and the term "pain" encompasses both acute and chronic pain. As used herein, the term "acute pain" means immediate, generally high threshold, pain brought about by injury such as a cut, crush, burn, or by chemical stimulation such as that experienced upon exposure to capsaicin, the active ingredient in chili peppers. The term "chronic pain," as used herein, means pain other than acute pain and includes, without limitation, neuropathic pain, visceral pain, inflammatory pain, headache pain, muscle pain and referred pain. It is understood that chronic pain is of relatively long duration, for example, several years and can be continuous or intermittent.

In one embodiment, the methods of the invention are used to treat "neuropathic pain," which, as used herein, is a term that means pain resulting from injury to a nerve. Neuropathic pain is distinguished from nociceptive pain, which is the pain caused by acute tissue injury involving small cutaneous nerves or small nerves in muscle or connective tissue. In contrast to neuropathic pain, pain involving a nociceptive mechanism usually is limited in duration to the period of tissue repair and generally is alleviated by available analgesic agents or opioids (Myers, *Regional Anesthesia* 20:173-184 (1995)).

Neuropathic pain typically is long-lasting or chronic and can develop days or months following an initial acute tissue injury. Neuropathic pain can involve persistent, spontaneous pain as well as allodynia, which is a painful response to a stimulus that normally is not painful, or hyperalgesia, an accentuated response to a painful stimulus that usually is trivial, such as a pin prick. Neuropathic pain generally is resistant to opioid therapy (Myers, supra, 1995).

The methods of the invention are useful in alleviating neuropathic pain resulting from, without limitation, a trauma, injury or disease of peripheral nerve, dorsal root ganglia, spinal cord, brainstem, thalamus or cortex. Examples of neuropathic pain which can be treated by the methods of the invention include neuralgia such as postherpetic neuralgia, deafferentation pain and diabetic neuropathy. It is understood that the methods of the invention are useful in alleviating neuropathic pain regardless of the etiology of the pain. As examples, the methods of the invention can be used to alleviate neuropathic pain resulting from a peripheral nerve disorder such as neuroma; from nerve compression; from nerve crush or stretch or incomplete nerve transsection; or from a mononeuropathy or polyneuropathy. As further examples, the methods of the invention are useful in alleviating neuropathic pain resulting from a disorder such as dorsal root ganglion compression; inflammation of the spinal cord; contusion, tumor or hemisection of the spinal cord; and tumors or trauma of the brainstem, thalamus or cortex.

As indicated above, the methods of the invention can alleviate neuropathic pain resulting from a mononeuropathy or polyneuropathy. A neuropathy is a functional disturbance or pathological change in the peripheral nervous system and is characterized clinically by sensory or motor neuron abnormalities. The term mononeuropathy indicates that a single peripheral nerve is affected, while the term polyneuropathy indicates that several peripheral nerves are affected. The etiology of a neuropathy can be known or unknown. Known etiologies include complications of a disease or toxic state such as diabetes, which is the most common metabolic disorder causing neuropathy, or irradiation, ischemia or vasculitis. Polyneuropathies that can be treated by a method of the invention can result, without limitation, from postpolio syndrome, diabetes, alcohol, amyloid, toxins, HIV, hypothyroidism, uremia, vitamin deficiencies, chemotherapy, ddC or Fabry's disease. It is understood that the methods of the invention can be used to alleviate pain of these or other neuropathies of known or unknown etiology.

As additional non-limiting examples, the methods of the invention can be used to treat chronic gastrointestinal inflammations including Crohn's disease, ulcerative colitis, gastritis, irritable bowel disease; and chronic visceral pain such as pain caused by cancer or attendant to the treatment of cancer, for example, attendant to chemotherapy or radiation therapy. Similarly, the methods of the invention can be used to treat chronic inflammatory pain resulting, for example, from arthritis such as rheumatoid arthritis, gouty arthritis, or osteoarthritis; spondylitis; or autoimmune diseases such as lupus erythematosus. The methods of the invention further can be used to treat headache pain; muscle pain; and the pain associated with substance abuse or withdrawal and other types of pain of known or unknown etiology.

Several of the methods of the invention rely, in part, on an "α-adrenergic agonist," which, as used herein, is a term which means a compound having greater than 25% efficacy relative to brimonidine at one or more α-2 adrenergic receptors or having greater than 25% efficacy relative to phenylephrine at one or more α-1 adrenergic receptors. Such a compound can be selective for one or more α-adrenergic receptors, or can be non-selective. Thus, the term α-adrenergic agonist encompasses, without limitation, "pan-α-1 pan-α-2 agonists" such as norepinephrine, which have agonist activity at all α-1 and α-2 receptors; pan-α-2 agonists; α-2 selective agonists; α-2B agonists; and agonists that are specific for a single α-adrenergic receptor. In particular embodiments, a method of the invention utilizes an α-adrenergic agonist having greater than 30%, 40%, 50%, 60%, 70%, 80%, 90%, 100% or 200% efficacy relative to brimonidine at one or more α-2 adrenergic receptors. In additional embodiments, a method of the invention utilizes an α-adrenergic agonist having greater than 30%, 40%, 50%, 60%, 70%, 80%, 90%, 100% or 200% efficacy relative to phenylephrine at one or more α-1 adrenergic receptors. In another embodiment, the invention relies on an α-adrenergic agonist lacking significant α-2A antagonist activity.

Efficacy, also known as intrinsic activity, is a measure of maximal receptor activation achieved by a compound and can be determined using any accepted assay of α-adrenergic receptor activation, such as a cAMP or Receptor Selection and Amplification Technology (RSAT) assay described hereinbelow. Efficacy is represented as a ratio or percentage of the maximal effect of the drug to the maximal effect of a standard agonist for each receptor subtype. Brimonidine (UK14304) generally is used as the standard agonist for the α-2A, α-2B and α-2C receptors and is used as the standard herein where efficacy of an α-2 receptor is defined. Phenylephrine is an accepted standard agonist for the α-1A, α-1 and α-1D receptors and is used herein as the standard where efficacy of an α-1 receptor is defined (Messier et al., supra, 1995; Conklin et al., supra, 1993).

As disclosed herein, α-2B agonists can be useful in alleviating pain or for the long-term relief of chronic pain. The term "α-2B agonist," as used herein, means a compound having greater than 25% efficacy relative to brimonidine at the α-2B adrenergic receptor. It is understood that this term encompasses agonists that are either selective or non-selective for the α-2B receptor as compared to other α-adrenergic receptors. Thus, the term "α-2B agonist" encompasses pan-α-2 agonists and pan-α-1 pan-α-2 agonists as well as agonists that are selective or specific for the α-2B receptor, as described further below. In particular embodiments, a method of the invention utilizes an α-2B agonist having greater than 30%, 40%, 50%, 60%, 70%, 80%, 90%, 100% or 200% efficacy relative to brimonidine at the α-2B adrenergic receptor. Exemplary α-2B agonists include clonidine, brimonidine, Compounds 1 and 2, and Compounds 3 through 12 and 14, and all pharmaceutically acceptable salts, esters, amides, sterioisomers and racemic mixtures of these compounds. In a further embodiment, a method of the invention relies on an α-2B agonist lacking significant α-2A antagonist activity.

The term "pan-α-2 agonist," as used herein, means a compound having greater than 25% efficacy relative to brimonidine at each of the α-2A, α-2B and α-2C adrenergic receptors and encompasses pan-α-1 pan-α-2 agonists. A variety of pan-α-2 agonists are known in the art and include clonidine, brimonidine, tizanidine, dexemedetomidine and norepinephrine. A pan-α-2 agonist has, at a minimum, greater than 25% efficacy relative to brimonidine at each of the α-2A, α-2B and α-2C receptors; in particular embodiments, a method of the invention is practiced with a pan-α-2 agonist having greater than 30%, 40%, 50%, 60%, 70%, 80%, 90%, 100% or 200% efficacy relative to brimonidine at the α-2A, α-2B and α-2C adrenergic receptors. It is understood that the efficacy of a pan-α-2 agonist can be different at the various α-2 receptors; as an example, a pan-α-2 agonist can have greater than 25% efficacy at the α-2A receptor, greater than 80% efficacy at the α-2B receptor and greater than 40% efficacy at the α-2C receptor.

The term "pan-α-1 pan-α-2 agonist," as used herein, means a compound having greater than 25% efficacy relative to phenylephrine at all α-1 receptors and having greater than 25% efficacy relative to brimonidine at all α-2 adrenergic receptors. In particular embodiments, a method of the invention relies on a pan-α-1 pan-α-2 agonist having greater than 30%, 40%, 50%, 60%, 70%, 80%, 90%, 100% or 200% efficacy at all α-1 and α-2 receptors relative to phenylephrine or brimonidine, respectively.

As disclosed herein, a selective α-2A antagonist is administered in conjunction with an α-adrenergic agonist to alleviate pain or for the long-term relief of chronic pain. As used herein, the term "selective α-2A antagonist" means a compound having (1) an efficacy of less than 25% relative to brimonidine at α-2A; (2) a Ki of less than 100 nM at α-2A; and further having (3) at least a 10-fold greater Ki at α-2B than at α-2A or an efficacy of greater than 25% relative to brimonidine at α-2B. From this definition, it is clear to the skilled person that non-selective antagonists such as rauwolscine are not included within the scope of this term. Exemplary selective α-2A antagonists are provided herein as Compound 13, BRL 48962 and BRL 44408. Pharmaceutically acceptable salts, esters, amides, sterioisomers and racemic mixtures of these compounds also are useful in the invention. A selective α-2A antagonist can be a peripherally limited compound. Such a compound does not readily cross the blood-brain barrier and, thus, upon peripheral administration, is excluded from the central nervous system.

In addition to α-2A antagonist activity, a "selective α-2A antagonist" also can have agonist or antagonist activity at one or more adrenergic or other receptors, provided that the compound satisfies the three criteria set forth above. As an example, a compound having α-2C antagonist activity, characterized by a Ki at α-2C of less than 100 nM and an efficacy at α-2C of less than 25% relative to brimonidine, and further having (1) an efficacy of less than 25% relative to brimonidine at α-2A, a Ki of less than 100 nM at α-2A, and (3) at least a 10-fold greater Ki at α-2B than at α-2A is encompassed by the term "selective α-2A antagonist" as defined herein. Similarly, compounds exhibiting α-2B or other agonist activity in addition to α-2A antagonist activity also are encompassed by the term "selective α-2A antagonist." As an example, Compound 13 exhibits α-2B agonist activity characterized by about 40% efficacy at α-2B relative to brimonidine, thus satisfying criteria (3), and further has (1) an efficacy of 5% relative to brimonidine at α-2A and (2) a Ki of about 0.08 nM at α-2A and, therefore, falls within the definition of the term "selective α-2A antagonist" as used herein. In particular embodiments, a method of the invention is practiced with a selective α-2A antagonist having a Ki of less than 80 nM, 60 nM, 40 nM, 20 nM, 10 nM, 1 nM or 0.1 nM. In further embodiments, a method of the invention is practiced with a selective α-2A antagonist having at least a 20-fold, 30-fold, 40-fold, 50-fold, 100-fold, 200-fold, 500- fold or 1000-fold greater Ki at α-2B than at α-2A. In still further embodiments, a method of the invention is practiced with a selective α-2A antagonist having an efficacy of greater than 30%, 40%, 50%, 60%, 70%, 80%, 90%, 100% or 200% relative to brimonidine at α-2B.

In one embodiment, the invention relies on a selective α-2A antagonist with minimal α-2B antagonist activity. As used herein, the term "selective α-2A antagonist with minimal α-2B antagonist activity" means a selective α-2A antagonist, as defined hereinabove, further having a Ki at α-2B greater than 100 nM. As non-limiting examples, such an antagonist can have a Ki at α-2B of greater than 200 nM, 300 nM, 400 nM, 500 nM, 1000 nM, 2000 nM, 3000 nM, 4000 nM or 5000 nM.

A specific α-2A antagonist also can be used to prevent α-2A receptor activation in a method of the invention. As used herein, the term "specific α-2A antagonist" means a compound having (1) an efficacy of less than 25% relative to brimonidine at α-2A; (2) a Ki of less than 100 nM at α-2A; and further having (3) at each of the α-adrenergic receptors other than α-2A either at least a 10-fold greater Ki than at α-2A or an efficacy of greater than 25% relative to brimonidine or phenylephrine.

The present invention also provides compositions and methods which rely on an α-adrenergic agonist with minimal α-2A agonist activity. In particular, the present invention provides an analgesic composition that contains an α-adrenergic agonist with minimal α-2A agonist activity having the ability to produce peripheral analgesia without concomitant sedation. In one embodiment, the analgesic composition produces peripheral analgesia without concomitant sedation and in the substantial absence of hypotensive effects. In another embodiment, the invention provides an analgesic composition that produces peripheral analgesia sufficient to reduce pain by at least 50% without concomitant sedation. In further embodiments, at least a 10-fold, 100-fold or 1000-fold greater dose of the analgesic composition is required to produce a 20% reduction in motor or muscular activity than the dose of the analgesic composition required to reduce pain by at least 50%. In yet a further embodiment, the invention provides an analgesic composition that produces peripheral analgesia sufficient to reduce pain by at least 50% without concomitant sedation and in the substantial absence of hypotensive effects. In another embodiment, the invention provides an analgesic composition that contains an α-adrenergic agonist with minimal α-2A agonist activity having the ability to produce peripheral analgesia without concomitant sedation, where the agonist is not a thiourea or derivative thereof. In a further embodiment, the invention provides an analgesic composition that contains an α-adrenergic agonist with minimal α-2A agonist activity having the ability to produce peripheral analgesia without concomitant sedation, where the agonist is not a thiourea or 4-imidazole or derivative thereof.

The invention also provides a method of alleviating pain in a subject by peripherally administering to the subject a pharmaceutical composition containing an effective amount of an α-adrenergic agonist with minimal α-2A agonist activity, thereby producing peripheral analgesia without concomitant sedation. Such peripheral analgesia can be sufficient to reduce pain, for example, by at least 50% without concomitant sedation. In another embodiment, the peripheral analgesia occurs in the substantial absence of hypotensive effects. In a further embodiment, the method is practiced using an α-adrenergic agonist with minimal α-2A agonist activity which is not a thiourea or derivative thereof. And, in yet a further embodiment, the method is practiced using an α-adrenergic agonist with minimal α-2A agonist activity which is not a thiourea or 4-imidazole or derivative thereof. Pain of various types and etiologies can be alleviated according to a method of the invention. As non-limiting examples, the methods of the invention can be useful in alleviating neuropathic pain, such as the pain resulting from diabetic neuropathy; visceral pain; post-operative pain; pain resulting from cancer or cancer treatment; inflammatory pain such as arthritic pain or irritable bowel syndrome pain; headache pain and muscle pain.

A variety of α-adrenergic agonists with minimal α-2A agonist activity can be useful in the methods of the invention. In one embodiment, the α-adrenergic agonist with minimal α-2A agonist activity is an α-2B agonist with minimal α-2A agonist activity. Such an agonist can be, for example, a thione such as Compound 3, or Compound 11 or a pharmaceutically acceptable salt, ester, amide, sterioisomer or racemic mixture thereof. In one embodiment, a method of the invention is practiced with an α-2B agonist with minimal α-2A agonist activity which is the (−) enantiomer of Compound 3 or a pharmaceutically acceptable salt or ester thereof.

α-2B agonists with minimal α-2A agonist activity useful in the invention further include, but are not limited to, imidazolones. A useful imidazolone α-2B agonist with minimal α-2A agonist activity can be, for example, Compound 4 or a pharmaceutically acceptable salt, ester, amide, sterioisomer or racemic mixture thereof. In one embodiment, the α-2B agonist with minimal α-2A agonist activity is the (+) enantiomer of Compound 4 or a pharmaceutically acceptable salt, ester or amide thereof. In additional embodiments, a method of the invention is practiced using one of the following α-2B agonists with minimal α-2A agonist activity: Compound 5, Compound 6, Compound 7, Compound 8, Compound 9, Compound 14 or a pharmaceutically acceptable salt, ester, amide, sterioisomer or racemic mixture thereof. An α-adrenergic agonist with minimal α-2A agonist activity can be peripherally administered by any of a variety of routes including, without limitation, oral administration and administration via subcutaneous minipump.

As used herein, the term "peripheral analgesia" means a reduction in pain obtained following peripheral administration. As discussed further below, peripheral administration means introduction of an agent into a subject outside of the central nervous system and encompasses any route of administration other than direct administration to the spine or brain. The peripheral analgesia can be sufficient to reduce pain, for example, by at least 30%, 40%, 50%, 60%, 70%, 80%, 90% or 100%.

The compositions of the invention produce peripheral analgesia without concomitant sedation. Sedation, as used herein, is a term that means a reduction in motor or muscular activity. The term "without concomitant sedation," as used herein, means that relatively little reduction in motor or muscular activity accompanies peripheral analgesia at one or more doses of drug. In particular, a drug produces "peripheral analgesia without concomitant sedation" if, upon peripheral administration, the dose required to produce a 20% reduction in motor or muscular activity is at least 3-fold greater than the dose required to reduce pain by at least 50%. In particular embodiments, the dose required to produce a 20% reduction in motor or muscular activity is at least 4-fold greater than, 5-fold greater than, 6-fold greater than, 7-fold greater than, 8-fold greater than, 9-fold greater than, 10-fold greater than, 25-fold greater than, 50-fold greater than, 100-fold greater than, 200-fold greater than, 500-fold greater than, 1000-fold greater than, 2000-fold greater than, or 5000-fold greater than the dose required to reduce pain by at least 50%. Methods of determining the extent of pain reduction and the extent of sedation following peripheral administration are well known in the art and are described hereinbelow.

As used herein, the term "α-adrenergic agonist with minimal α-2A agonist activity" means an α-adrenergic agonist, as defined above, further characterized by (1) having less than 25% efficacy relative to brimonidine at the α-2A adrenergic receptor and (2) the ability to produce peripheral analgesia without concomitant sedation in genetically unaltered animals. It is understood that efficacy is measured using any standard assay of agonist activity such as a cAMP or RSAT assay described hereinbelow. Compounds 3, 4, 5, 6, 7, 8, 9, 10, 11 and 12 as well as pharmaceutically acceptable salts, esters, amides, sterioisomers and racemic mixtures thereof are provided herein as exemplary α-adrenergic agonists with minimal α-2A agonist activity; such compounds belong to diverse structural classes as shown in Table 1 above. α-adrenergic agonists with minimal α-2A agonist activity useful in the invention encompass α-adrenergic agonists with activity at one or more α-1 receptors, α-2B/C agonists with minimal α-2A agonist activity, specific α-2B agonists with minimal α-2A activity and specific α-2C agonists with minimal α-2A activity, as described further below.

α-adrenergic agonists with minimal α-2A agonist activity can readily be identified by screening α-adrenergic agonists, for example, by screening those exhibiting less than 25% efficacy at α-2A for functional activity in various in vitro or in vivo assays. In particular, such agonists can be assayed for peripheral analgesic activity without concomitant sedation in both wild type and α-2A knockout mice, for example, using the well-accepted model of sulprostone sensitized pain. Agonists with more than minimal α-2A agonist activity can be eliminated as those compounds which fail to produce peripheral analgesia without concomitant sedation in wild type sulprostone sensitized animals, although peripheral analgesia without concomitant sedation is observed in α-2A knockout mice, as described further below. In particular embodiments, a method of the invention is practiced using an α-adrenergic agonist with minimal α-2A agonist activity which produces, without concomitant sedation, peripheral analgesia sufficient to reduce pain by at least 50%, or by at least 60%, 70%, 80%, 90% or 100% in genetically unaltered animals.

As used herein, the term "α-2B agonist with minimal α-2A agonist activity" means a compound characterized by having (1) greater than 25% efficacy relative to brimonidine at the α-2B receptor; (2) a potency of less than 1000 nM at α-2B or at least 100-fold greater potency at α-2B than at α-2A; (3) less than 25% efficacy relative to brimonidine at the α-2A receptor; and (4) the ability to produce peripheral analgesia without concomitant sedation in genetically unaltered animals. Provided herein as exemplary α-2B agonists with minimal α-2A agonist activity are Compounds 3, 4, 5, 6, 7, 8, 9, 10, 11, 12 and 14 and pharmaceutically acceptable salts, esters, amides, sterioisomers and racemic mixtures of these compounds; as exemplified herein, these compounds are characterized, in part, by the ability to produce peripheral analgesia without concomitant sedation in genetically unaltered animals. In particular embodiments, an α-2B agonist with minimal α-2A agonist activity useful in the invention has an efficacy of greater than 30%, 40%, 50%, 60%, 70%, 80%, 90%, 100% or 200% relative to brimonidine at α-2B. In additional embodiments, an α-2B agonist with minimal α-2A agonist activity has less than 20%, 15%, 10%, 5%, 2% or 1% efficacy relative to brimonidine at α-2A. In further embodiments, an α-2B agonist with minimal α-2A agonist activity has a potency of less than 900 nM, 800 nM, 700 nM, 600 nM, 500 nM, 400 nM, 300 nM, 200 nM, 100 nM, 50 nM, 10 nM or 1 nM at α-2B. In still further embodiments, an α-2B agonist with minimal α-2A agonist activity has at least 200-fold, 300-fold, 400-fold, 500-fold, 1000-fold or 10,000-fold greater potency at α-2B than at α-2A. In additional embodiments, the methods of the invention rely on an α-2B agonist with minimal α-2A agonist activity having the ability to produce, without concomitant sedation, peripheral analgesia sufficient to reduce pain by at least 50% or by at least 60%, 70%, 80%, 90% or 100% in genetically unaltered animals.

The term "α-2B/C agonist with minimal α-2A agonist activity" as used herein, means a compound characterized by having (1) greater than 25% efficacy relative to brimonidine at the α-2B or α-2C receptor or both; (2) a potency of less than 1000 nM at the α-2B or α-2C receptor or both, or at least 100-fold greater potency relative to the α-2A receptor at the α-2B or α-2C receptor or both; (3) less than 25% efficacy relative to brimonidine at the α-2A receptor; and (4) the ability to produce peripheral analgesia without concomitant sedation in genetically unaltered animals.

The term "specific α-2B agonist with minimal α-2A activity," as used herein, means a compound characterized by having (1) greater than 25% efficacy relative to brimonidine at α-2B; (2) a potency of less than 1000 nM at α-2B or at least 100-fold greater potency at α-2B than α-2A; (3) less than 25% efficacy or 50-fold less potency relative to brimonidine at α-2A and α-2C; (4) less than 25% efficacy or 50-fold less potency relative to phenylephrine at all α-1 receptors; and (5) the ability to produce peripheral analgesia without concomitant sedation in genetically unaltered animals.

Similarly, the term "specific α-2C agonist with minimal α-2A activity," as used herein, means a compound characterized by having (1) greater than 25% efficacy relative to brimonidine at α-2C; (2) a potency of less than 1000 nM at α-2C or at least 100-fold greater potency at α-2C than α-2A; (3) less than 25% efficacy or 50-fold less potency relative to brimonidine at α-2A and α-2B; (4) less than 25% efficacy or 50-fold less potency relative to phenylephrine at all α-1 receptors; and (5) the ability to produce peripheral analgesia without concomitant sedation in genetically unaltered animals.

Agonist and antagonist activity, including selectivity and specificity, can be characterized using any of a variety of routine assays, including, without limitation, Receptor Selection and Amplification Technology (RSAT) assays (Messier et al., *Pharmacol. Toxicol.* 76:308-11 (1995); Conklin et al., *Nature* 363:274-6 (1993)); cyclic AMP assays (Shimizu et al., *J. Neurochem.* 16:1609-1619 (1969)); and cytosensor microphysiometry assays (Neve et al., *J. Biol. Chem.* 267:25748-25753 (1992)). Such assays generally are performed using cells that naturally express only a single α-adrenergic receptor subtype, or using transfected cells expressing a single recombinant α-adrenergic receptor subtype. The adrenergic receptor can be a human receptor or homolog thereof having a similar pharmacology. As disclosed herein, RSAT assays were performed using cells transiently transfected with human α-2A (c10 gene); rat α-2B (RNG gene); human α-2C (c4 gene); bovine α-1A; hamster α-1B; and rat α-1D.

The RSAT assay measures receptor-mediated loss of contact inhibition resulting in selective proliferation of receptor-containing cells in a mixed population of confluent cells. The increase in cell number is assessed with an appropriate detectable marker gene such as β-galactosidase, if desired, in a high throughput or ultra high throughput assay format. Receptors that activate the G protein, Gq, elicit the proliferative response. α-adrenergic receptors, which normally couple to Gi, activate the RSAT response when coexpressed with a hybrid Gq protein containing a Gi receptor recognition domain, designated Gq/i5.

As an example, an RSAT assay can be performed essentially as follows. NIH-3T3 cells are plated at a density of $2 \times 10^6$ cells in 15 cm dishes and maintained in Dulbecco's modified Eagle's medium supplemented with 10% calf serum. One day later, cells are cotransfected by calcium phosphate precipitation with mammalian expression plasmids encoding p-SV-β-galactosidase (5-10 μg), receptor (1-2 μg) and G protein (1-2 μg). Carrier DNA, for example 40 μg salmon sperm DNA, also can be included to increase transfection efficiency. Fresh media is added on the following day; one to two days later, cells are harvested and frozen in 50 assay aliquots. Transfected cells are thawed, and 100 μl of cells added to 100 μl aliquots of compound to be tested, with various concentrations assayed in triplicate, for example, in 96-well plates. Incubation continues for 72 to 78 hours at 37°. After washing with phosphate-buffered saline, β-galactosidase activity is determined by adding 200 μl of chromogenic substrate (3.5 mM O-nitrophenyl-β-D-galactopyranoside/0.5% NP-40 in phosphate buffered saline), incubating overnight at 30°, and measuring optical density at 420 nm. The absorbancy is a measure of enzyme activity, which depends on cell number and reflects receptor-mediated cell proliferation. The $EC_{50}$ and maximal effect (efficacy) of each drug at each receptor is determined.

The present invention further provides a method for the long-term relief of chronic pain in a subject. The method is practiced by activating in the subject an analgesic α-adrenergic receptor in the absence of α-2A receptor activation over a period of at least three days, such that relief of chronic pain is maintained in the absence of continued receptor activation. In one embodiment, a method of the invention is practiced by administering to the subject a pharmaceutical composition containing an effective amount of an α-adrenergic agonist with minimal α-2A agonist activity over a period of at least three days, such that relief of chronic pain is maintained in the absence of significant agonist levels in the subject. Relief of chronic pain can be maintained, for example, for at least three weeks in the absence of significant agonist levels in the subject. It is understood that the methods of the invention can be used for the long-term relief of any type of chronic pain. As non-limiting examples, such methods can be used for the long-term relief of neuropathic pain; visceral pain; post-operative pain; pain resulting from cancer or cancer treatment; and inflammatory pain.

Long-term chronic pain relief can be achieved according to a method of the invention with any of a variety of α-adrenergic agonists with minimal α-2A agonist activity. Long-term chronic pain relief can be achieved, for example, using an α-2B agonist with minimal α-2A agonist activity. Exemplary α-2B agonists with minimal α-2A agonist activity include, without limitation, thiones such as Compound 3 and Compound 11, and pharmaceutically acceptable salts, esters, amides, sterioisomers and racemic mixtures thereof. In one embodiment, such a thione α-2B agonist with minimal α-2A agonist activity is the (−) enantiomer of Compound 3, or a pharmaceutically acceptable salt or ester thereof. Exemplary α-2B agonists with minimal α-2A agonist activity further include, without limitation, imidazolones such as Compound 4 or a pharmaceutically acceptable salt, ester, amide, sterioisomer or racemic mixture thereof. In one embodiment, such a imidazolone α-2B agonist with minimal α-2A agonist activity is the (+) enantiomer of Compound 4, or a pharmaceutically acceptable salt or ester thereof. Exemplary α-2B agonists with minimal α-2A agonist activity also include, without limitation, Compound 5, Compound 6, Compound 7, Compound 8 and Compound 9, and pharmaceutically acceptable salts, esters, amides, sterioisomers and racemic mixtures thereof. In the methods of the invention, an α-adrenergic agonist with minimal α-2A agonist activity can be administered by any of a variety of routes including, but not limited to, a route of peripheral administration such as oral administration or administration via subcutaneous minipump.

The present invention further provides a method for the long-term relief of chronic pain in a subject by administering to the subject a pharmaceutical composition containing an effective amount of an α-adrenergic agonist and a pharmaceutical composition containing an effective amount of a selective α-2A antagonist over a period of at least three days, such that relief of chronic pain is maintained in the absence of significant agonist levels in the subject. Chronic pain relief can be maintained, for example, for at least three weeks in the absence of significant agonist levels in the subject. A variety of α-adrenergic agonists are useful in the invention including clonidine, brimonidine, tizanidine, dexemedetomidine, norepinephrine and other pan-α-2 agonists and pan-α-1 pan-α-2 agonists as well as Compound 1 or Compound 2, and pharmaceutically acceptable salts, esters, amides, sterioisomers and racemic mixtures thereof. Similarly, a variety of selective α-2A antagonists are useful in long-term relief of chronic pain including, without limitation, Compound 13 and pharmaceutically acceptable salts, esters, amides, sterioisomers and racemic mixtures thereof. It is understood that various routes of administration are useful for delivering pharmaceutical compositions for the long-term relief of chronic pain as discussed further below. Such routes of administration encompass, but are not limited to, peripheral administration, for example, oral administration or administration via subcutaneous minipump.

The methods of the invention provide long-term relief of chronic pain. As used herein," the term "long-term relief" means a significant reduction in pain that lasts for at least ten days following last administration of the pharmaceutical composition. In particular embodiments, the relief lasts for at least fourteen days, at least 21 days, at least 28 days, at least 60 days, or at least 90 days following last administration of the pharmaceutical composition. In further embodiments, the invention provides a method for the long-term relief of chronic pain in which the pain is reduced by at least 50% for at least ten days, at least fourteen days, at least 21 days, at least 28 days, at least 60 days, or at least 90 days following last administration of the pharmaceutical composition. In additional embodiments, the invention provides a method for the long-term relief of chronic pain in which the pain is reduced by at least 80% for at least ten days, at least fourteen days, at least 21 days, at least 28 days, at least 60 days, or at least 90 days following last administration of the pharmaceutical composition. In other embodiments, the invention provides a method for the long-term relief of chronic pain in which the pain is reduced by at least 90% for at least ten days, at least fourteen days, at least 21 days, at least 28 days, at least 60 days, or at least 90 days following last administration of the pharmaceutical composition.

Methods for the long-term relief of chronic pain are practiced by administering an α-adrenergic agonist with minimal α-2A activity over a period of at least three days.

The agonist can be administered by repeated dosing or continuous dosing over a period of at least three days, for example, over three days, four days, five days, six days, seven days, eight days, nine days or ten days. As non-limiting examples, the α-adrenergic agonist with minimal α-2A activity can be administered three times a day for three days, or three times a day for four days, for example, orally three times a day for three days, or orally three times a day for four days. As further examples, the α-adrenergic agonist with minimal α-2A activity can be administered continuously, for example, intravenously, via implanted infusion minipump or using an extended release formulation for three days, four days, five days, six days or seven days.

It is understood that slow-release formulations can be useful in the methods of the invention for the long-term relief of chronic pain. It is further understood that, where repeated administration is used, the frequency of administration depends, in part, on the half-life of the agonist. If desired, a method of the invention can be practiced by administering a single dose, or just two or three doses, of an agonist with a long half-life, for example, a half-life of at least 24 hours, 36 hours, 48 hours, or 72 hours.

It is understood that different means of drug delivery can be combined in a method of the invention. As an example, continuous intravenous administration on the first day can be combined with repeated oral dosing on the second and third days to activate an analgesic α-adrenergic receptor in the absence of α-2A receptor activation over a period of at least three days, such that relief of chronic pain is maintained in the absence of significant agonist levels in said subject. It is understood that the frequency and duration of dosing will be dependent, in part, on the relief desired and the half-life of the agonist, and that a variety of routes of administration are useful in the methods of the invention, as detailed further hereinbelow.

Also encompassed by the invention are pharmaceutically acceptable salts, esters and amides derived from the formula representing the specified agonist or antagonist. Suitable pharmaceutically acceptable salts of the agonists and antagonists useful in the invention include, without limitation, acid addition salts, which can be formed, for example, by mixing a solution of the agonist or antagonist with a solution of an appropriate acid such as hydrochloric acid, sulfuric acid, fumaric acid, maleic acid, succinic acid, acetic acid, benzoic acid, citric acid, tartaric acid, carbonic acid or phosphoric acid. Where an agonist or antagonist carries an acidic moiety, suitable pharmaceutically acceptable salts thereof can include alkali salts such as sodium or potassium salts; alkaline earth salts such as calcium or magnesium salts; and salts formed with suitable organic ligands, for example, quaternary ammonium salts. Representative pharmaceutically acceptable salts include, yet are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

The functional groups of agonists and antagonists useful in the invention can be modified to enhance the pharmacological utility of the compound. Such modifications are well within the knowledge of the skilled chemist and include, without limitation, esters, amides, ethers, N-oxides, and pro-drugs of the indicated agonist or antagonist. Examples of modifications that can enhance the activity of an agonist or antagonist include, for example, esterification such as the formation of $C_1$ to $C_6$ alkyl esters, preferably $C_1$ to $C_4$ alkyl esters, wherein the alkyl group is a straight or branched chain. Other acceptable esters include, for example, $C_1$ to $C_7$ cycloalkyl esters and arylalkyl esters such as benzyl esters. Such esters can be prepared from the compounds described herein using conventional methods well known in the art of organic chemistry.

Other pharmaceutically acceptable modifications include the formation of amides. Useful amide modifications include, for example, those derived from ammonia; primary $C_1$ to $C_6$ dialkyl amines, where the alkyl groups are straight or branched chain; and arylamines having various substitutions. In the case of secondary amines, the amine also can be in the form of a 5 or 6 membered ring. Methods for preparing these and other amides are well known in the art.

It is understood that, where an agonist or antagonist useful in the invention has at least one chiral center, the agonist or antagonist can exist as chemically distinct enantiomers. In addition, where an agonist or antagonist has two or more chiral centers, the compound exists as diastereomers. All such isomers and mixtures thereof are encompassed within the scope of the indicated agonist or antagonist. Similarly, where an agonist or antagonist possesses a structural arrangement that permits the structure to exist as tautomers, such tautomers are encompassed within the scope of the indicated agonist or antagonist. Furthermore, in crystalline form, an agonist or antagonist may exist as polymorphs; in the presence of a solvent, an agonist may form a solvate, for example, with water or a common organic solvent. Such polymorphs, hydrates and other solvates also are encompassed within the scope of the indicated agonist or antagonist as defined herein.

An agonist or antagonist useful in the invention generally is administered in a pharmaceutical composition. If desired, the composition may, in some cases, be administered in conjunction with one or more other therapeutic or analgesic substances, in the same or different pharmaceutical compositions and by the same or different routes of administration. As one example, an an α-adrenergic agonist with minimal α-2A agonist activity can be administered together with an analgesic agent such as gabapentin. As another example, an α-adrenergic agonist with minimal α-2A agonist activity can be administered together with one or more cancer chemotherapeutic agents in an intravenous cocktail.

A pharmaceutical composition useful in the invention includes the active agonist or antagonist and further can include, if desired an excipient such as a pharmaceutically acceptable carrier or a diluent, which is any carrier or diluent that has substantially no long term or permanent detrimental effect when administered to a subject. Such an excipient generally is mixed with active compound, or permitted to dilute or enclose the active compound. A carrier can be a solid, semi-solid, or liquid agent that acts as an excipient or vehicle for the active compound. Examples of pharmaceutically acceptable carriers and diluents include, without limitation, water, such as distilled or deionized water; saline; and other aqueous media. It is understood that the active ingredients can be soluble or can be delivered as a suspension in the desired carrier or diluent.

A pharmaceutical composition further can include, if desired, one or more agents such as emulsifying agents, wetting agents, sweetening or flavoring agents, tonicity adjusters, preservatives, buffers or anti-oxidants. Tonicity adjustors useful in a pharmaceutical composition include salts such as sodium chloride, potassium chloride, mannitol or glycerin and other pharmaceutically acceptable tonicity adjustors. Preservatives useful in the pharmaceutical compositions of the invention include, without limitation, benzalkonium chloride, chlorobutanol, thimerosal, phenylmercuric acetate, and phenylmercuric nitrate. Various buffers and means for adjusting pH can be used to prepare a pharmaceutical composition, including, but not limited to, acetate buffers, citrate buffers, phosphate buffers and borate buffers. Similarly, anti-oxidants useful in the pharmaceutical compositions of the invention are well known in the art and include, for example, sodium metabisulfite, sodium thiosulfate, acetylcysteine, butylated hydroxyanisole and butylated hydroxytoluene. It is understood that these and other substances known in the art of pharmacology can be included in a pharmaceutical composition useful in the invention.

The agonists and antagonists of the invention are administered in effective amounts. Such an effective amount generally is the minimum dose necessary to achieve the desired therapeutic effect, which can be, for example, that amount roughly necessary to reduce the discomfort caused by the pain to tolerable levels. Such a dose generally is in the range of 0.1-1000 mg/day and can be, for example, in the range of 0.1-500 mg/day, 0.5-500 mg/day, 0.5-100 mg/day, 0.5-50 mg/day, 0.5-20 mg/day, 0.5-10 mg/day or 0.5-5 mg/day, with the actual amount to be administered determined by a physician taking into account the relevant circumstances including the severity of the pain, the age and weight of the patient, the patient's general physical condition, the cause of pain and the route of administration. Suppositories and extended release formulations can be useful in the invention and include, for example, dermal patches, formulations for deposit on or under the skin and formulations for intramuscular injection.

A pharmaceutical composition useful in the methods of the invention can be administered to a subject by a variety of means depending, for example, on the type of pain to be treated, the agonist or antagonist to be included in the composition, and the history, risk factors and symptoms of the subject. Routes of administration suitable for the methods of the invention include both systemic and local administration. As non-limiting examples, a pharmaceutical composition useful for alleviating pain or for the long-term relief of chronic pain can be administered orally or by subcutaneous pump; by dermal patch; by intravenous, subcutaneous or intramuscular injection; by topical drops, creams, gels or ointments; as an implanted or injected extended release formulation; by subcutaneous minipump or other implanted device; by intrathecal pump or injection; or by epidural injection.

In particular embodiments, a method of the invention is practiced by peripheral administration of a pharmaceutical composition containing an agonist, a pharmaceutical composition containing an antagonist, or both. As an example, one or both of a pharmaceutical composition containing an α-adrenergic agonist and a pharmaceutical composition containing a selective α-2A antagonist can be administered peripherally. As used herein, the term "peripheral administration" or "administered peripherally" means introducing an agent into a subject outside of the central nervous system. Peripheral administration encompasses any route of administration other than direct administration to the spine or brain. As such, it is clear that intrathecal and epidural administration as well as cranial injection or implantation are not within the scope of the term "peripheral administration" or "administered peripherally." It further is clear that some analgesic agents can cross the blood-brain barrier and, thus, become distributed throughout the central and peripheral nervous systems following peripheral administration.

Peripheral administration can be local or systemic. Local administration results in significantly more of a pharmaceutical composition being delivered to and about the site of local administration than to regions distal to the site of administration. Systemic administration results in delivery of a pharmaceutical composition to essentially the entire peripheral nervous system of the subject and may also result in delivery to the central nervous system depending on the properties of the composition.

Routes of peripheral administration useful in the methods of the invention encompass, without limitation, oral administration, topical administration, intravenous or other injection, and implanted minipumps or other extended release devices or formulations. A pharmaceutical composition useful in the invention can be peripherally administered, for example, orally in any acceptable form such as in a tablet, liquid, capsule, powder, or the like; by intravenous, intraperitoneal, intramuscular, subcutaneous or parenteral injection; by transdermal diffusion or electrophoresis; topically in any acceptable form such as in drops, creams, gels or ointments; and by minipump or other implanted extended release device or formulation.

In some embodiments, the invention is practiced by administering both a pharmaceutical composition containing an effective amount of an α-adrenergic agonist and a pharmaceutical composition containing an effective amount of a selective α-2A antagonist to a subject. In such "combination" therapy, it is understood that the agonist and antagonist can be delivered independently or simultaneously, in the same or different pharmaceutical compositions, and by the same or different routes of administration. As an example, both agonist and antagonist can be administered orally, with the agonist given twice daily and the antagonist given once daily. As another example, the agonist can be administered epidurally while the antagonist is administered orally. As a further example, the agonist and antagonist can be administered together in an intravenous "cocktail."

The present invention also provides a method of screening for effective agents that produce peripheral analgesia without concomitant sedation by contacting an α-2A receptor with an α-adrenergic agonist having analgesic activity; and determining whether the agonist has α-2A agonist activity, where the absence of α-2A agonist activity indicates that the α-adrenergic agonist having analgesic activity is an effective agent that produces peripheral analgesia without concomitant sedation.

Further provided herein is a method of screening for effective agents that produce peripheral analgesia without concomitant sedation by contacting an α-2A receptor with an agent; determining whether the agent has α-2A agonist activity; contacting an α-2B receptor with the agent; and determining whether the agent has α-2B agonist activity, where the absence of α-2A agonist activity and the presence of α-2B agonist activity indicate that the agent is an effective agent that produces peripheral analgesia without concomitant sedation.

The invention also provides a method of screening for effective agents that produce peripheral analgesia without concomitant sedation by peripherally administering an α-adrenergic agonist to a control animal having at least wild type levels of α-2A receptor activity; assaying for analgesia in the control animal; peripherally administering to a corresponding animal having reduced levels of α-2A receptor expression or activity an amount of the α-adrenergic agonist similar or greater than the amount administered to the control animal; and assaying for analgesia in the corresponding animal having reduced levels of α-2A receptor expression or activity, where the absence of analgesia in the control animal and the presence of analgesia in the corresponding animal having reduced levels of α-2A receptor expression or activity indicate that the α-adrenergic agonist has excessive α-2A agonist activity, and where the presence of analgesia in the control animal and the presence of analgesia in said corresponding animal having reduced levels of α-2A receptor expression or activity indicate that the α-adrenergic agonist is an effective agent that produces peripheral analgesia without concomitant sedation. In such a method of the invention, the control animal can be, for example, wild type at both α-2A receptor loci. In one embodiment, the control animal is a wild type animal such as a wild type mouse. A variety of corresponding animals are useful in a screening method of the invention. In one embodiment, the invention is practiced with a corresponding animal having a homozygous point mutation at the α-2A receptor locus. In another embodiment, the invention is practiced with a corresponding animal having a point mutation within the α-2A receptor coding sequence. Such a point mutation can occur, for example, at a residue analogous to Asp79 and can be, for example, an Asp79 to Asn mutation. In a further embodiment, the invention is practiced with a corresponding animal having a homozygous α-2A knockout mutation. It is understood that a variety of methodologies can be used to assay for analgesia in the methods of the invention, including, but not limited to, assaying for analgesia following sulprostone sensitization.

If desired, a method of the invention for screening for effective agents that produce peripheral analgesia without concomitant sedation can be practiced by (a) peripherally administering an α-adrenergic agonist to a control animal having at least wild type levels of α-2A and α-2B receptor activity; (b) assaying for analgesia in the control animal; (c) peripherally administering to a corresponding animal having reduced levels of α-2A receptor expression or activity an amount of the α-adrenergic agonist similar or greater than the amount administered to the control animal; (d) assaying for analgesia in the corresponding animal having reduced levels of α-2A receptor expression or activity; (e) peripherally administering the α-adrenergic agonist to a corresponding animal having reduced levels of α-2B receptor expression or activity; and (f) assaying for analgesia in the corresponding animal having reduced levels of α-2B receptor expression or activity, where the absence of analgesia in the control animal and the presence of analgesia in the corresponding animal having reduced levels of α-2A receptor expression or activity indicate that the α-adrenergic agonist has excessive α-2A agonist activity, and where the presence of analgesia in the control animal, the presence of analgesia in said corresponding animal having reduced levels of α-2A receptor expression or activity, and the absence of analgesia in the corresponding animal having reduced levels of α-2B receptor expression or activity indicate that the α-adrenergic agonist is an effective agent that produces peripheral analgesia without concomitant sedation.

The present invention additionally provides a method of screening for effective agents that produce peripheral analgesia without concomitant sedation by peripherally administering an α-adrenergic agonist to a control animal having at least wild type levels of α-2B receptor activity; assaying for analgesia in the control animal; peripherally administering the α-adrenergic agonist to a corresponding animal having reduced levels of α-2B receptor expression or activity; and assaying for analgesia in the corresponding animal having reduced levels of α-2B receptor expression or activity, where the presence of analgesia in the control animal and the absence of analgesia in the corresponding animal having reduced levels of α-2B receptor expression or activity indicate that the α-adrenergic agonist is an effective agent that produces peripheral analgesia without concomitant sedation.

Such a method of the invention can be practiced with a variety of control animals, for example, a control animal which is wild type at both α-2B receptor loci. In one embodiment, the control animal is a wild type animal. In a further embodiment, the control animal is a wild type mouse. Similarly, a variety of corresponding animals are useful in the screening methods of the invention, including corresponding animals which have a heterozygous α-2B knockout mutation or a homozygous α-2B knockout mutation. Analgesia can be assayed using any of a variety of methodologies. In one embodiment, analgesia is assayed following sulprostone sensitization.

The term "control animal," as used herein, means any animal capable of experiencing pain. A control animal can, for example, express wild type levels of endogenous α-2A receptor or can express an α-2A receptor transgene in addition to endogenous α-2A. Where a control animal is "wild type" at both α-2A receptor loci, the animal has α-2A receptor sequences that are naturally occurring and expressed at levels normally found in nature. Similarly, where a control animal is "wild type" at both α-2B receptor loci, the animal has α-2B receptor sequences that are naturally occurring and expressed at levels normally found in nature.

As used herein, the term "wild type animal" means an animal such as a mouse or rat that is unaltered through molecular genetics. A "wild type animal" can be a wild animal found in nature or can be an inbred animal or other laboratory strain with a well characterized genetic system.

The term "corresponding animal," as used herein, means an animal of the same species as the control animal, which has reduced levels of α-2A receptor expression or activity or which has reduced levels of α-2B receptor expression or activity. A corresponding animal generally is genetically identical to the control animal except at one or more α-2A receptor loci or at one or more α-2B receptor loci. As non-limiting examples, a corresponding animal can entirely lack one or both α-2A genes or one or both α-2B genes, have a deletion, insertion or point mutation in the α-2A or α-2B receptor coding sequence, a deletion, insertion or point mutation in the 5' or 3' regulatory sequence that reduces or eliminates α-2A or α-2B expression, or express wild type levels of α-2A receptor or α-2B receptor with reduced activity, such as a murine α-2A receptor having an Asp79 to Asn mutation, which abolishes about 80% of receptor activity. Thus, in one embodiment, a screening method of the invention is practiced with a corresponding animal having reduced levels of α-2A receptor expression or activity due to a homozygous point mutation at a residue analogous to Asp79; such an "analogous" residue is that asparagine residue occurring in the same relative position in a homolog of the murine α-2A receptor. α-2A and α-2B knockout mouse strains as well as strains bearing homozygous point mutations resulting in reduced levels of α-2A receptor expression or activity are well known in the art or can be prepared by standard methods (Hein et al., *Ann. NY Acad. Science* 881:265-271 (1999); and Kable et al., *J. Pharm. Exper. Therapeutics* 293:1-7 (2000)).

A screening method of the invention relies, in part, on peripherally administering an α-adrenergic agonist to a control animal and to a corresponding animal with reduced levels of α-2A receptor expression or activity or a corresponding animal with reduced levels of α-2B receptor expression or activity, or both corresponding animals. It is understood that administration to the control animal and administration to the one or more corresponding animals can be performed simultaneously or in any order. Similarly, it is understood that the two or more steps in which analgesia is assayed can be performed simultaneously or in any order. Assays for analgesic activity can be performed using any established or reproducible pain model, including, but not limited to, those exemplified herein. It is understood that analgesic activity in the control and corresponding animals is assayed under the same or similar conditions.

The following examples are intended to illustrate but not limit the present invention.

EXAMPLE I

Preparation of α-Adrenergic Agonist and Antagonist

This example describes synthesis of various α-adrenergic agonist, including α-adrenergic agonist with minimal α-2A agonist activity such as α-2B agonist with minimal α-2A agonist activity, and synthesis of a selective α-2A antagonist.

A. Synthesis of Compound 1

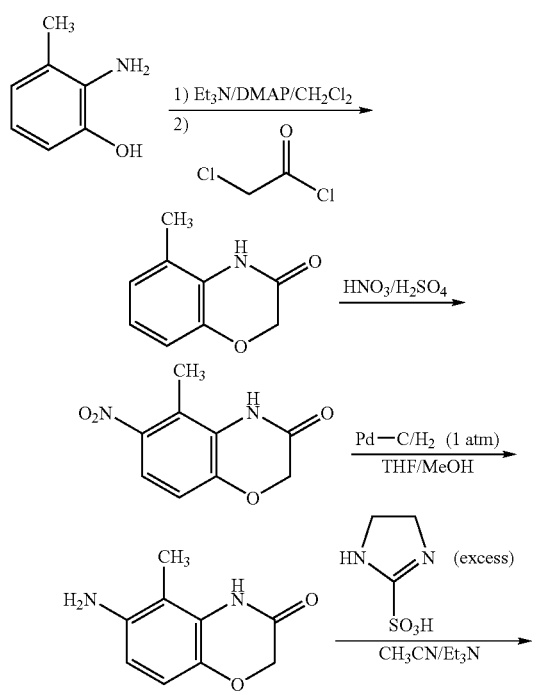

B. Synthesis of Compound 2

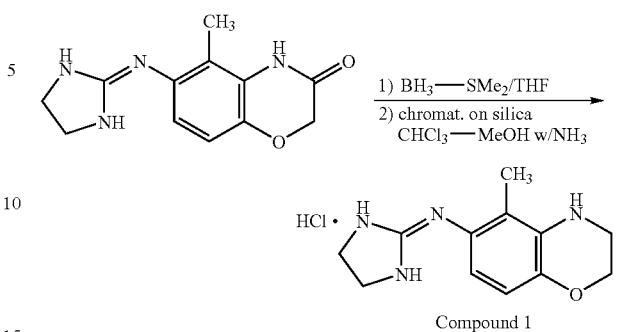

C. Synthesis of Compound 3

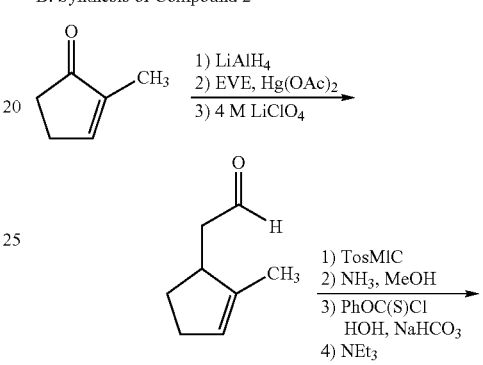

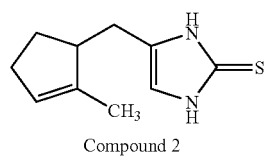

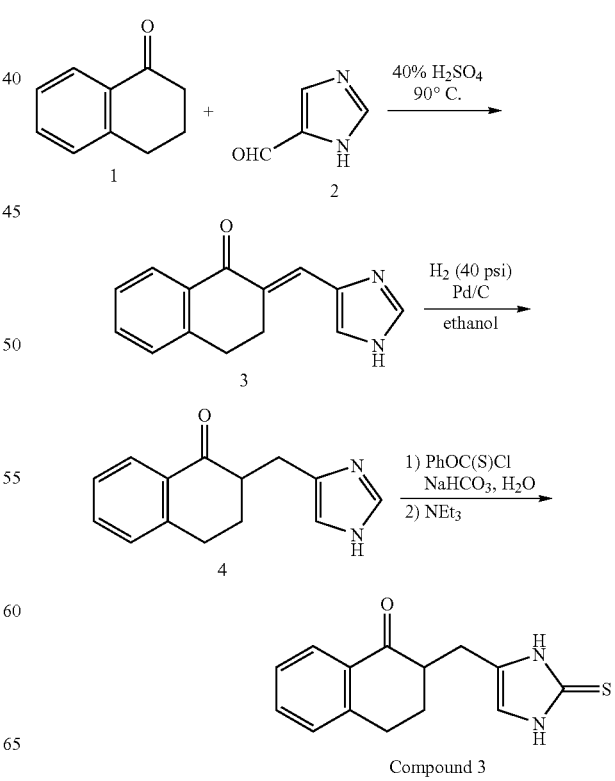

-continued
D. Synthesis of Compound 4
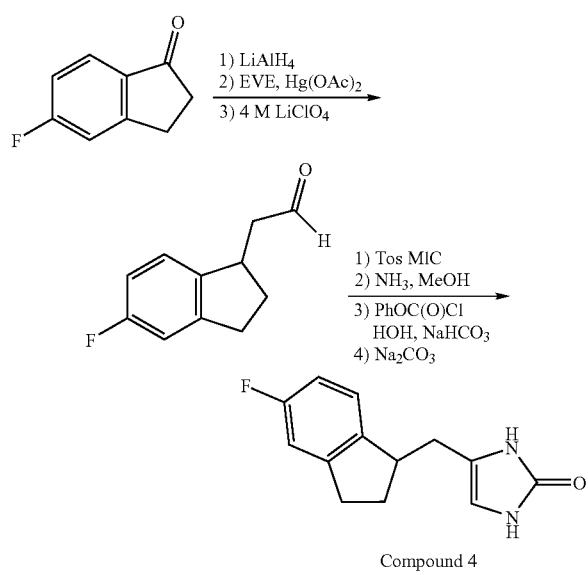
Compound 4
E. Synthesis of Compound 5
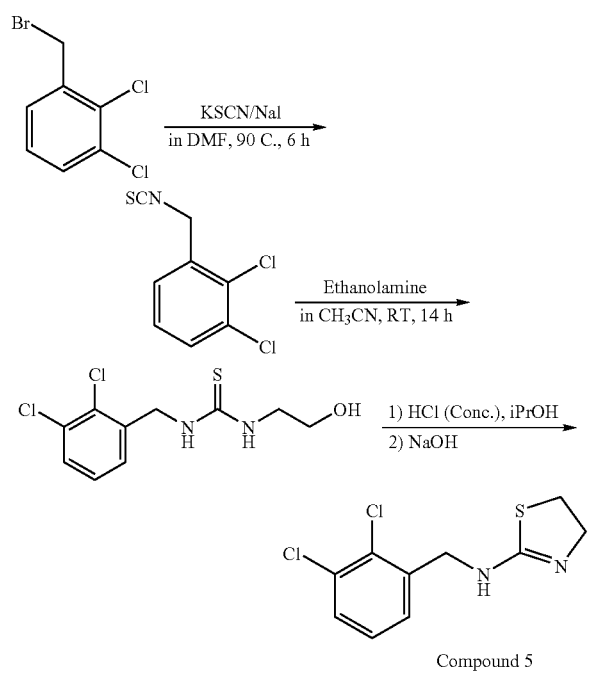
Compound 5
F. Synthesis of Compound 6
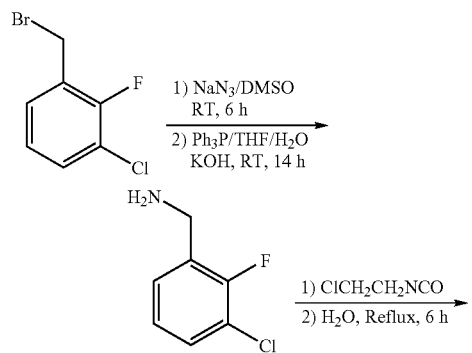
-continued
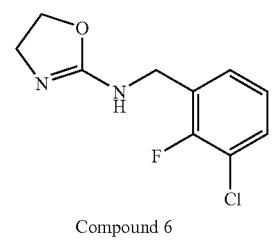
Compound 6
G. Synthesis of Compound 7
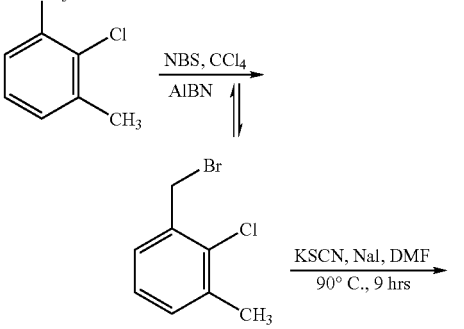
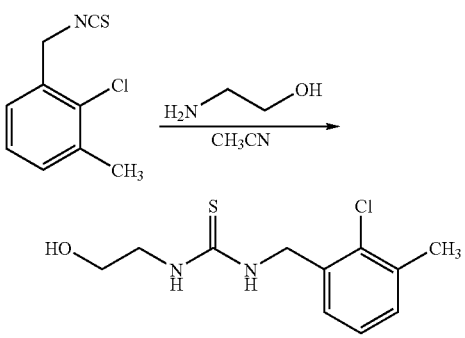
Compound 7
H. Synthesis of Compound 8
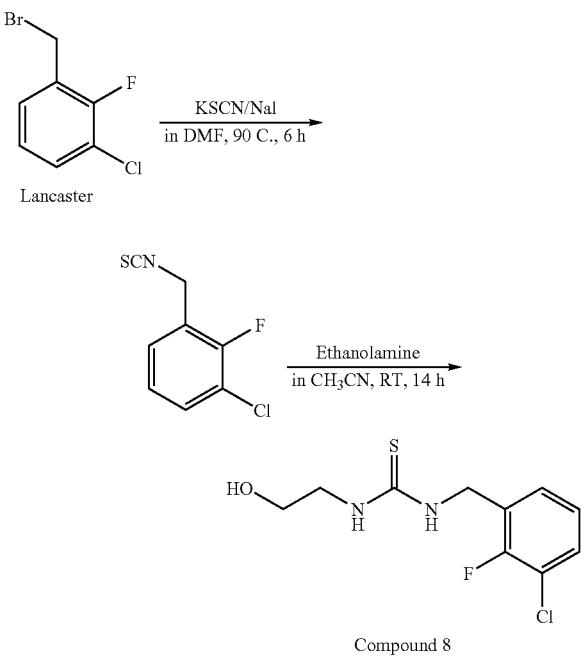
Compound 8

I. Synthesis of Compound 9
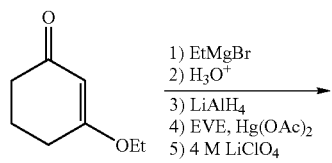
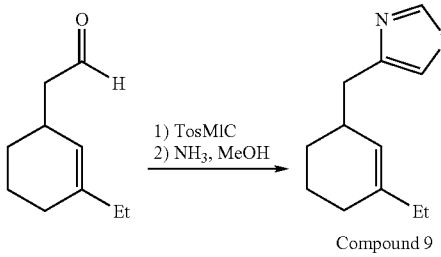
Compound 9
J. Synthesis of Compound 10
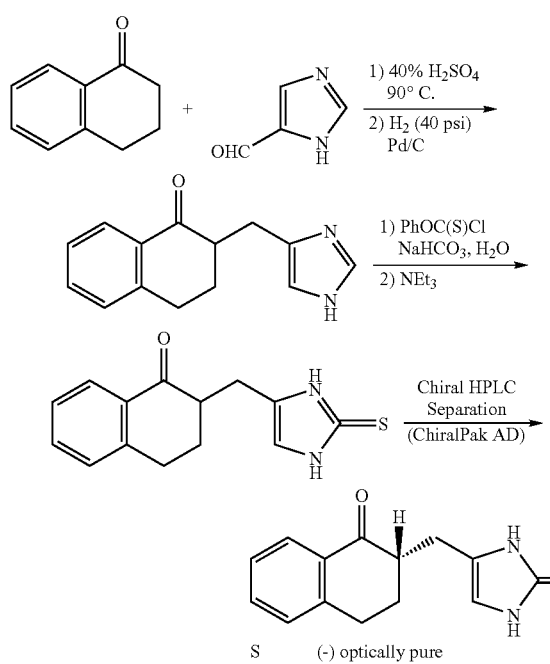
S (−) optically pure
Eluted first
Compound 10
K. Synthesis of Compound 11
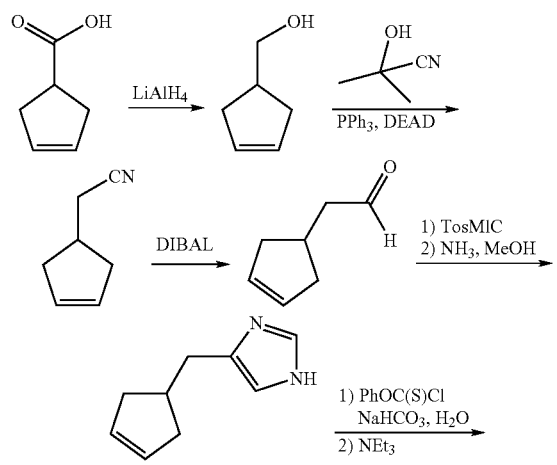
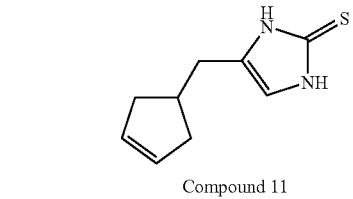
Compound 11
L. Synthesis of Compound 12
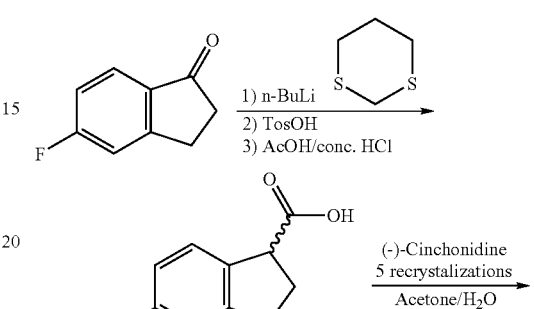
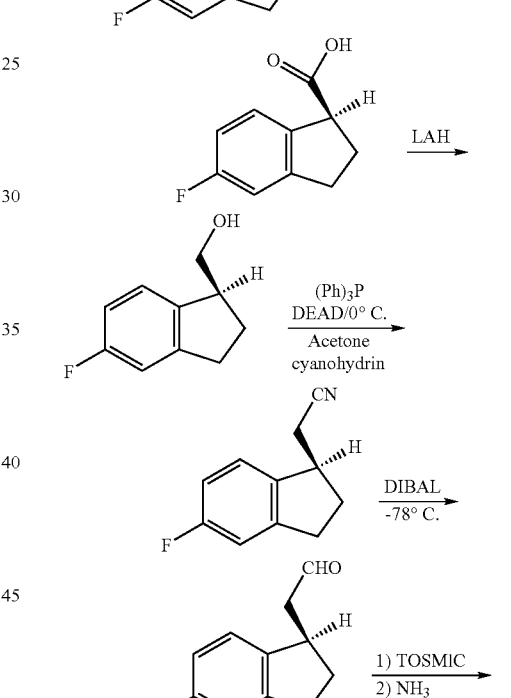
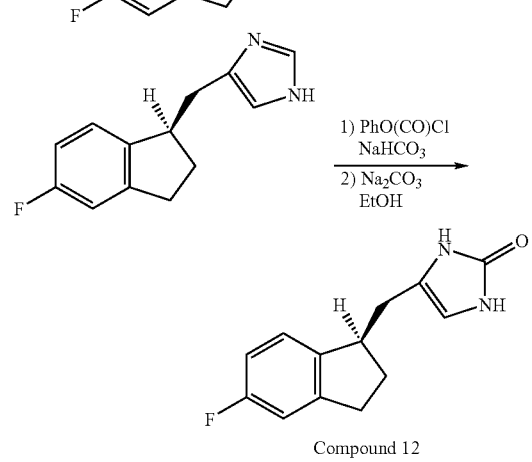
Compound 12

M. Synthesis of Compound 13

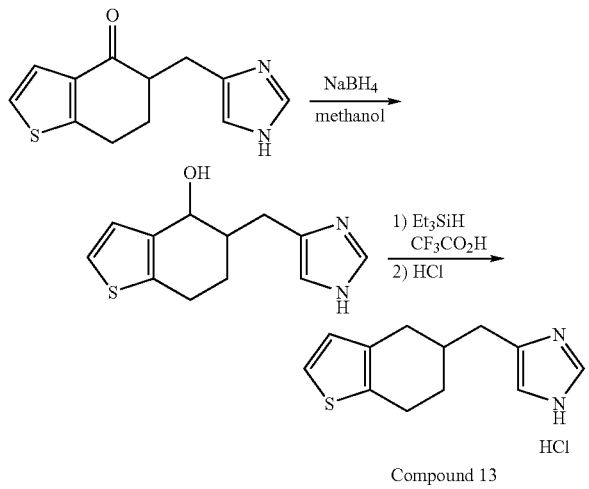

Compound 13

N. Synthesis of Compound 14

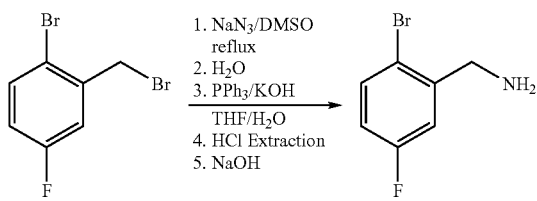

2-Bromo-5-fluorobenzyl bromide (3.0 g, 11 mmol, 1.0 equiv) was dissolved in dimethyl sulfoxide (100 mL) at ambient temperature. Sodium azide (2.8 g, 44 mmol, 4.0 equiv) was added to the solution and the reaction mixture heated at reflux for one day. The solution was cooled, quenched with water, and then extracted with ethyl acetate. The organic extracts were combined, washed with brine, dried over sodium sulfate and concentrated in vacuo. Purification by column chromatography (10:1 hexanes/ethyl acetate) afforded the azide (0.85 g, 34w). The azide (0.85 g, 3.7 mmol, 1.0 equiv) was dissolved in tetrahydrofuran (25 mL) and water (5.0 mL). KOH (0.20 g, 3.6 mmol, 0.97 equiv) was added to the solution followed by triphenylphosphine (1.1 g, 4.4 mmol, 1.2 equiv). The reaction mixture was stirred overnight at ambient temperature. The reaction was quenched with hydrochloric acid (conc.) and extracted with ethyl acetate. The aqueous layers were combined and made basic with sodium hydroxide (pellet) until pH reached ~14. The aqueous layer was extracted with ethyl acetate, the organic layers combined, washed with brine, dried over sodium sulfate and concentrated in vacuo to afford the crude amine (0.35 g, 46%) as an orange oil.

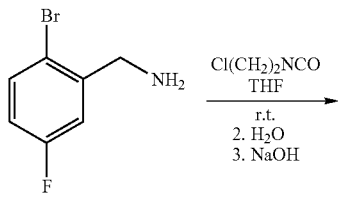

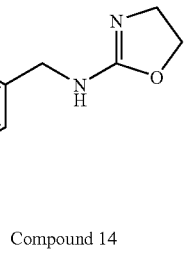

Compound 14

2-Bromo-5-fluorobenzyl amine (0.35 g, 1.7 mmol, 1.0 equiv) was dissolved in tetrahydrofuran (20 mL) and stirred overnight at ambient temperature. The solvent was removed in vacuo and water (30 mL) was used to dissolve the concentrate. The solution was heated at reflux overnight and then cooled to ambient temperature. Sodium hydroxide (pellet) was added to the solution until the pH was ~14. The solution was extracted with ethyl acetate, the organic extracts combined, washed with brine and dried over sodium sulfate. The solution was concentrated in vacuo. The concentrate was purified by column chromatography (30:1 chloroform /methanol sat'd with ammonia). The product was isolated as a white solid. H NMR (300 MHz, CDCl3 w/TMS): δ7.46-7.50 (m, 1H), 7.16-7.19 (m, 1H), 6.83-6.90 (m, 1H), 4.43 (s, 2H), 4.31 (t, 2H, J=8.5 Hz), 3.79 (t, 2H, J=8.8Hz).

EXAMPLE II

Peripheral Treatment of Pain in α2-A Receptor Knock-out Mice Using α-Adrenergic Agonists This example demonstrates that α-adrenergic agonists are effective analgesic agents when administered peripherally in the absence of α-2A receptor activation.

A. Peripherally Administered α-Adrenergic Agonists are Effective Analgesic Agents in α-2A Knockout Mice Non-specific α-adrenergic agonists were assayed in α-2A receptor deficient ("knockout") mice (Hein et al., supra, 1999) using a mouse model of sulprostone sensitized pain in which allodynia is evoked by intrathecal administration of a selective prostaglandin E2 receptor agonist to conscious mice essentially as described in Minami et al., Pain 57:217-223 (1994). In this model, the pain response to stroking the flank with a paint brush is scored eight times over a 35 minute period starting 15 minutes following spinal administration of sulprostone and intrathecal or intraperitoneal administration of drug or control vehicle. Sulprostone elicits a "pain" score of 12-13 on a 16-point scale.

Consistent with previous clinical data, intrathecal injection of clonidine, brimonidine (UK14304) or the charged α-adrenergic agonist Compound 1 produced significant analgesia separable from sedation in wild type mice. Furthermore, intrathecal injection of clonidine, brimonidine or Compound 1 into α-2A knockout mice did not produce analgesia, consistent with the therapeutic target of spinally administered α-adrenergic agonists being an α-2A receptor expressed in the dorsal horn of the spinal cord. FIGS. 1A and 1B show the results obtained with intrathecal administration of 1 μg Compound 1 in wild type and α-2A knockout mice. These results indicate that centrally mediated analgesia by non-selective α-adrenergic agonists requires α-2A receptor.

In contrast to the results obtained with intrathecal injection, intraperitoneal injection of 30 μg/kg Compound 1 as well as clonidine or brimonidine failed to produce analgesia separable from sedation in wild type mice. However, in α-2A knockout mice, peripheral (intraperitoneal) treatment with clonidine, UK14304 or Compound 1 resulted in significant analgesia without sedation. See FIGS. 1C and 1D, which show that, upon peripheral administration, Compound 1 only produced analgesia in α-2A knockout mice but not in wild type animals. These results indicate that α-adrenergic agonists can produce analgesia without significant sedation when administered peripherally in the absence of α-2A receptor activation.

Figure 2:
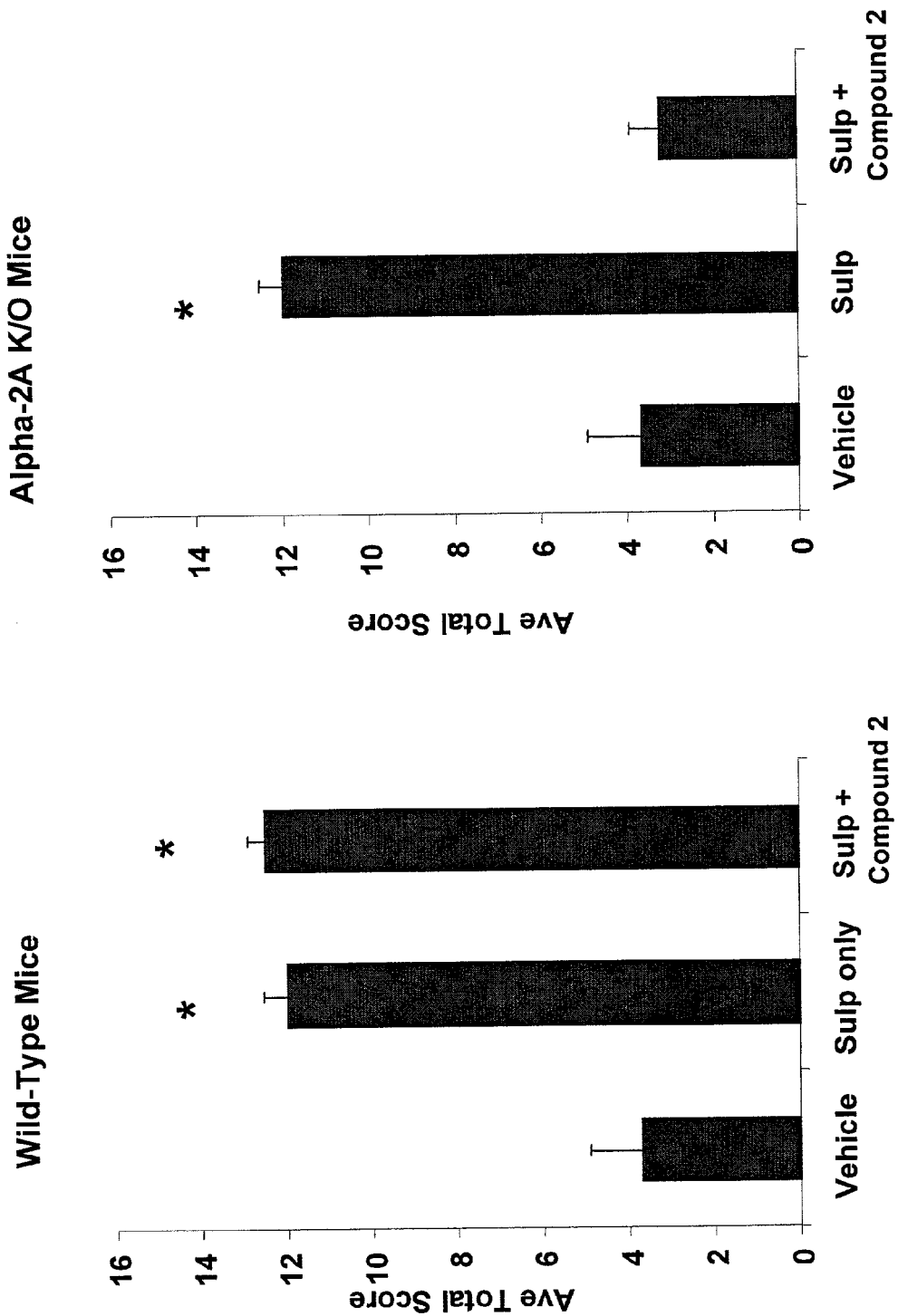
FIG. 2 shows the results obtained with intraperitoneal injection of Compound 2 into sulprostone-sensitized wild type and α-2A knockout mice. (A) Intraperitoneal injection of 100 μg/kg Compound 2 into wild type mice. (B) Intraperitoneal injection of 100 μg/kg Compound 2 into α-2A knockout mice. Asterisks indicate a significant result with a p value <0.05.

Wild type and α-2A knockout mice also were treated with 100 μg/kg of the α-adrenergic agonist, Compound 2, which, unlike clonidine, brimonidine, Compound 1 and PAC, has very little α-1 activity and only weakly activates the α-2A receptor with a relative efficacy of 40% relative to brimonidine in in vitro assays. Like clonidine, Compound 2 readily crosses the blood-brain barrier. In wild type mice, Compound 2 was not analgesic when administered intraperitoneally, but was fully analgesic in α-2A knockout mice when administered by the same route (see FIG. 2). These results indicate that a variety of α-adrenergic agonists with differing α-1 and α-2 receptor activity profiles and bioavailablility can be effective peripheral analgesic agents when α-2A receptor activation is prevented.

As disclosed above, activation of an α-2A receptor by α-adrenergic agonists masks the peripheral analgesic activity of these molecules. To test whether the masking effect was dependent on a spinal or peripherally localized α-2A receptor, mice were injected intrathecally or intraperitoneally with Compound 1, a highly charged α-adrenergic agonist that does not readily cross the blood-brain barrier. As indicated above, intrathecal, but not intraperitoneal, injection produced significant analgesia in wild type mice while the converse was true in α-2A knockout mice: intraperitoneal, but not intrathecal, injection resulted in analgesia. Similarly, another highly charged α-adrenergic agonist that does not readily cross the blood-brain barrier, para-amino clonidine (PAC), also was analgesic at 100 μg/kg in α-2A knockout mice when administered peripherally. These results indicate that a novel analgesic activity of non-selective α-adrenergic agonists such as pan-agonists is unmasked by preventing activation of a peripheral α-2A receptor.

Assays for allodynia in wild type and α-2A knockout mice were performed essentially according to the method of Yaksh and Harty, *J. Pharmacology Exp. Ther.* 244: 501-507 (1998). In brief, mice were divided into groups of 5-6 animals. Control mice were administered 5 ul DMSO while treated animals were injected with 5 ul DMSO containing various doses of the indicated agent. After intrathecal injection, each mouse was placed in an individual 13×8.5×13 cm Plexiglass enclosure with wood chips on the floor for observation. Allodynia was assessed once every five minutes over a 50 minute time period, with response recorded eight times in the 15 to 50 minute time frame. Allodynia was assessed by light stroking of the flank of the mice with a small paintbrush and ranked as follows: 0, no response; 1, mild squeaking with attempts to move away from the stroking probe; and 2, vigorous squeaking evoked by the stroking probe, biting at the probe and strong efforts to escape. The eight scores for each animal were added together, and the mean for the group determined to give an average total score.

B. A Peripheral α-2 Receptor Mediates Analgesia in α-2A Knockout Mice

Figure 3:
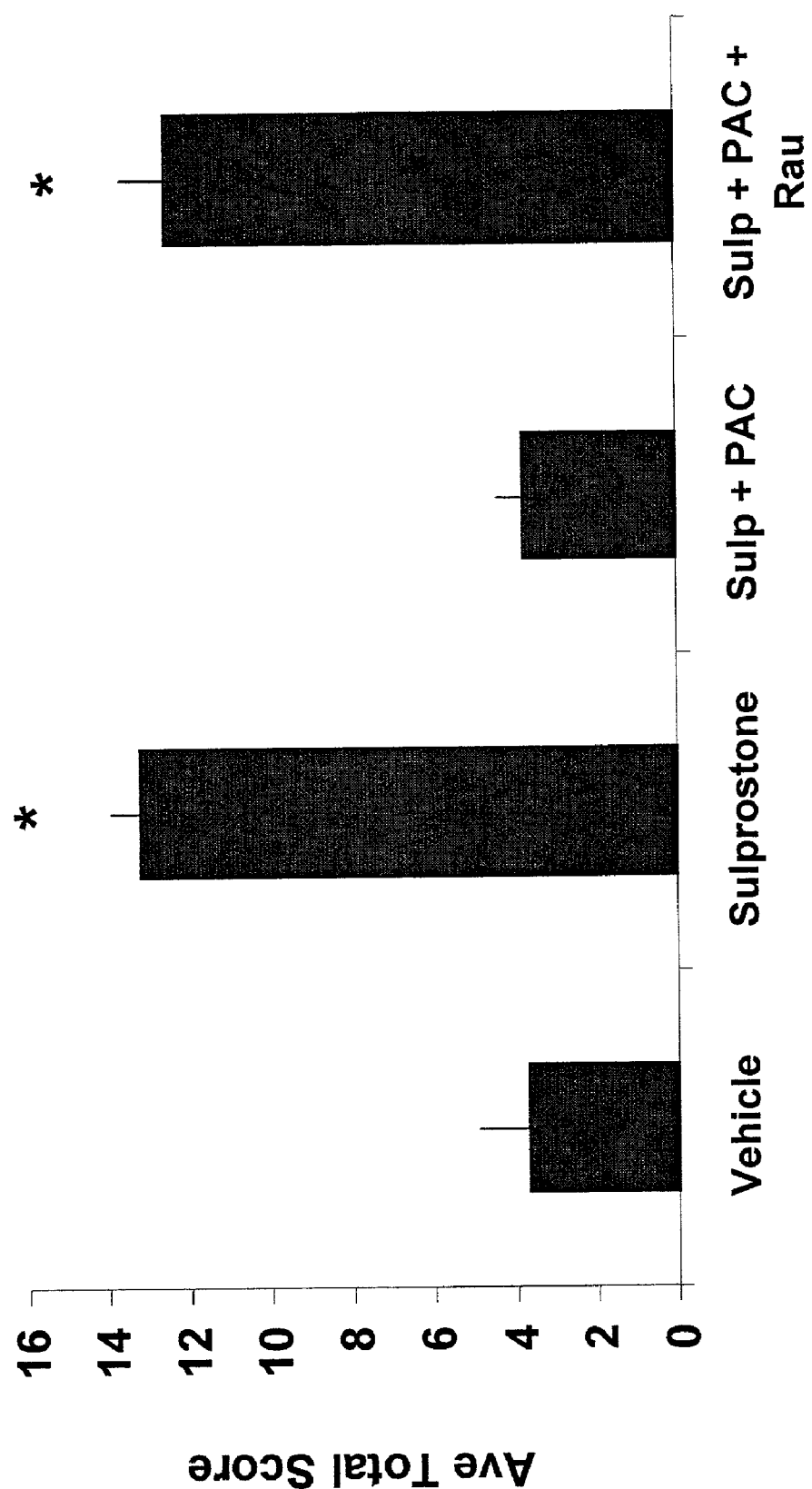
FIG. 3 shows that a peripheral α-2 receptor mediates analgesia in α-2A knockout mice. Para-amino clonidine (PAC) at 100 μg/kg, alone or in combination with rauwolscine (Rau) at 0.3 μg/kg, was administered to sulprostone-sensitized α-2A knockout mice by intraperitoneal injection. Asterisks indicate a significant result with a p value <0.05.

The non-selective α-2 antagonist, rauwolscine, was assayed for its ability to affect peripheral analgesia produced by para-amino-clonidine (PAC) in α-2A knockout mice. Sulprostone-sensitized α-2A knockout mice were treated with PAC, delivered at 100 μg/kg by intraperitoneal injection. As described above, PAC induced significant analgesia in the α-2A knockout mice. The analgesic effect of PAC was blocked, however, by intraperitoneal injection of rauwolscine (0.3 μg/kg) as shown in FIG. 3. These results indicate that a peripheral α-2 receptor mediates analgesia in α-2A knockout mice.

Sedative effects were analyzed by assessing exploratory behavior in a darkened chamber as follows. Mice were weighed, and test compound administered by intrathecal injection in a volume of 5 μl or by intraperitoneal injection in 1 ml/kg volume at the indicated dose. At predetermined time points corresponding with analgesia measurements 5 to 30 minutes following the injection, the animal's activity was determined automatically by placing the mouse in a digicom analyzer chamber (Omnitech Electronic; Columbus, Ohio). The digicom analyzer chamber contains photocell beams criss-crossing the box that are broken as the animal moves around; the chamber was modified for mice by raising the level of the floor. Computer analysis of total animal movement proceeded over a 5-minute time period. Any given animal was used at most twice for this protocol, as learned behavior can affect the data. All animals received at least two weeks rest between studies.

EXAMPLE III

Relief of Pain by Peripheral Administration of α-Adrenergic Agonists in Genetically Unaltered Animals This example demonstrates that α-adrenergic agonists can be peripherally administered to produce a significant analgesic effect with less than a 20% reduction in motor or muscular activity in animals having wild type α-adrenergic receptors.

A. Selective α-2A Antagonists can be Used in Combination With Peripherally Administered α-Adrenergic Agonists to Produce Analgesia The Chung rat nerve ligation model is a well accepted model of peripheral neuropathic pain. In the Chung model, partial ligation of left spinal nerves L-5 and L-6 produces a long-lasting hypersensitivity to light touch on the affected left foot. The hypersensitivity is similar to pain experienced by humans with the neuropathic condition of causalgia (Kim and Chung, *Pain* 50:355-363 (1992)).

When administered by intrathecal injection to Chung rats, the pan-α-2 agonist clonidine produced significant analgesia separable from sedation, while intraperitoneal administration only produced unremarkable analgesia in the absence of sedative effects. Compounds that do not readily cross the blood-brain barrier, Compound 1 and PAC, also were assayed for activity in the Chung rat model. As expected, neither compound was significantly analgesic at non-sedating doses when administered peripherally.

Figure 4:
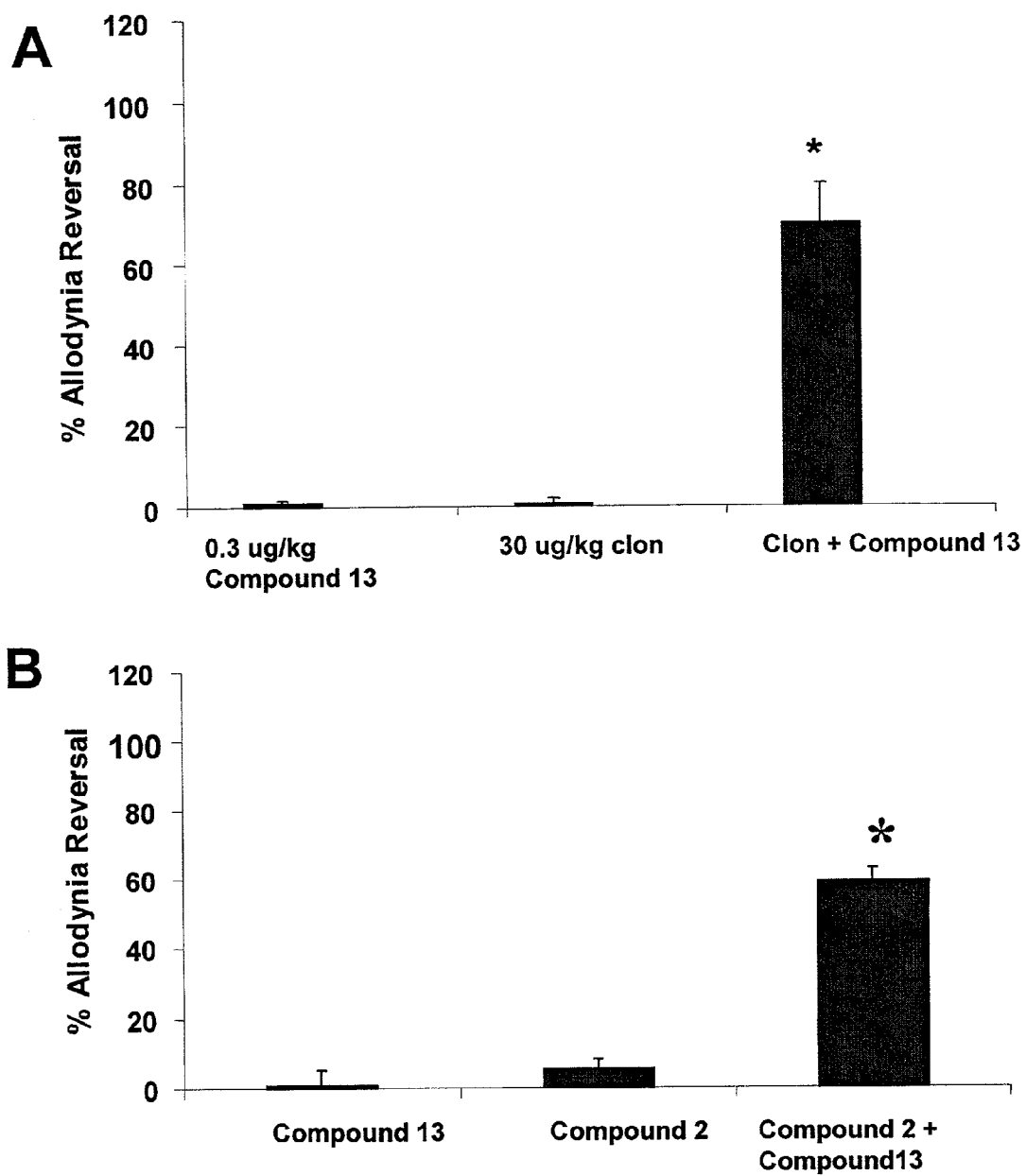
FIGS. 4A and 4B show that α-adrenergic agonists can be effective peripheral analgesic agents in wild type animals when α-2A receptor activation is blocked. Percentage allodynia reversal is shown for each set of animals. (A) Chung model rats were intraperitoneally administered 30 μg/kg clonidine, 0.3 μg/kg Compound 13, or both. (B) Chung model rats were intraperitoneally administered 100 μg/kg Compound 2, 0.3 μg/kg Compound 13, or both. Asterisks indicate a significant result with a p value <0.05.
FIGS. 4C and 4D compare the sedative and peripheral analgesic profiles of clonidine and Compound 3. (C) Total activity counts and percentage of allodynia reversal for intraperitoneally administered clonidine. (D) Total activity counts and percentage of allodynia reversal for intraperitoneally administered Compound 3. The total number of activity counts for vehicle-treated animals was approximately 2500. Asterisks indicate a significant result with a p value <0.05.
Figure 4:
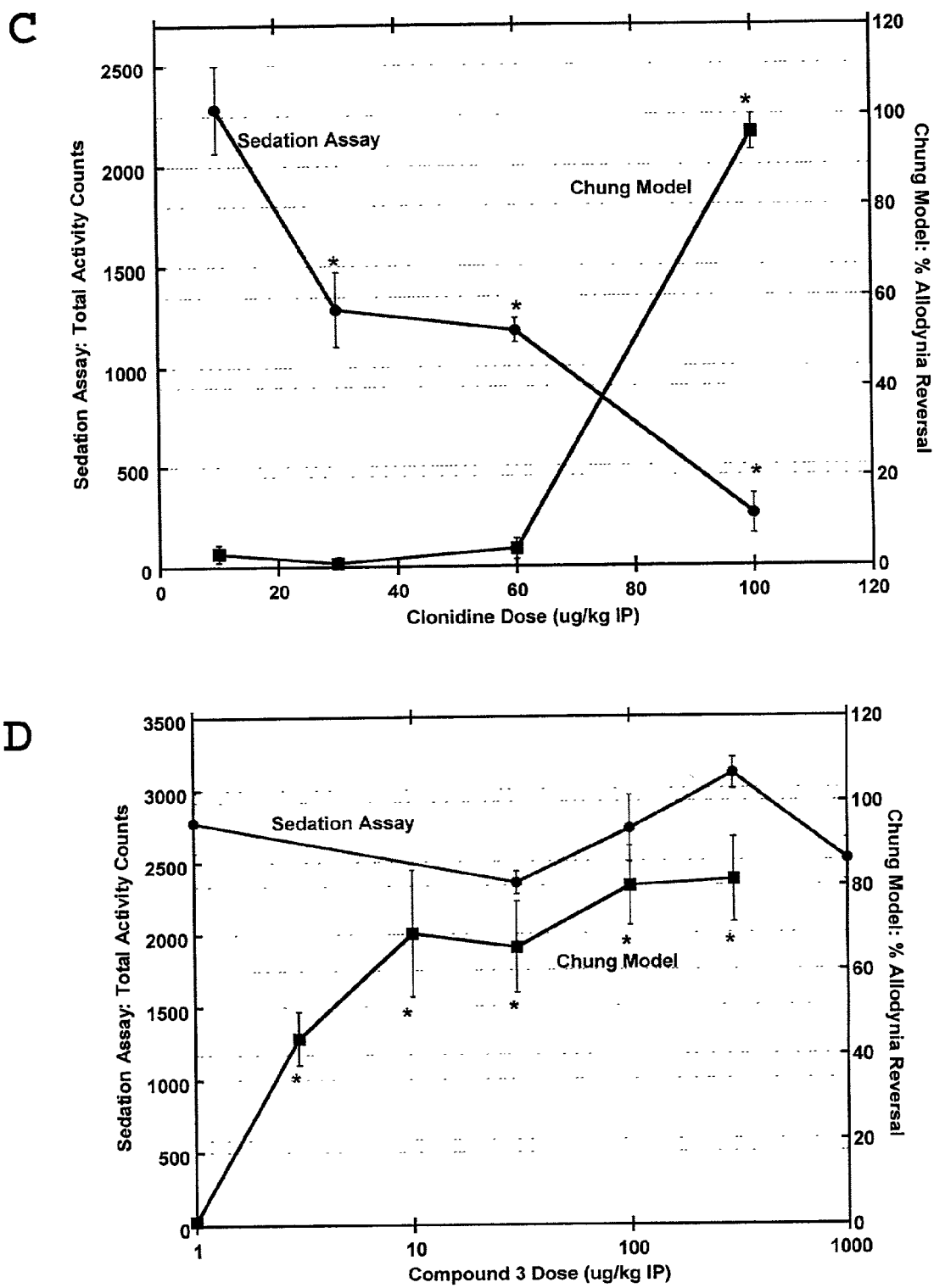

Coadministration of clonidine with the selective α-2A antagonist, Compound 13, shifted the analgesic dose response of intraperitoneally administered clonidine to the left; when combined with 0.3 μg/kg Compound 13, only 30 μg/kg was required to give dramatic allodynia reversal (see FIG. 4A). This concentration of clonidine reduces activity but was not nearly as sedating as the 100 µg/kg dose that reverses allodynia in the absence of Compound 13. Similarly, Compound 2 also was not analgesic when given alone by peripheral administration at 100 µg/kg to Chung rats, yet produced significant analgesia when co-administered with 0.3 µg/kg α-2A antagonist Compound 13 as shown in FIG. 4B; no significant sedative effects were observed at this concentration. Taken together, these results indicate that selective α-2A antagonists can be administered together with α-adrenergic agonists to unmask a novel, α-2A receptor-independent, peripheral analgesic property of α-adrenergic agonists.

α-2B/C selective agonists with some α-2A agonist activity were unable to produce significant analgesia separable from sedation when administered peripherally to Chung rats. As disclosed above, the thione Compound 2 has slight α-2A agonist activity, yet did not have analgesic activity when administered peripherally in the absence of an α-2A antagonist. This result indicates that peripheral analgesic activity of α-adrenergic agonists is dependent upon an extremely low level of α-2A receptor activation.

Chung rat surgeries of about 20 minutes duration were performed essentially as follows. Male Sprague-Dawley rats weighing 100 to 120 grams were anesthetized with isofluorane. After shaving and preparing the surgical site with betadine, an incision was made from thoracic vertebra XIII down toward the sacrum, and muscle separated from spinal vertebra (left side) at the L4-S2 levels. The L6 vertebra were located, and the transverse process carefully removed with a small rongeur to visually identify the L4-L6 spinal nerves. L5 and L6 spinal nerves were isolated and tightly ligated with 6-0 silk thread; the wound was sutured after complete hemostasis was confirmed. A small amount of antibiotic ointment was applied to the incised area before transferring the animals to a plastic recovery cage under a regulated heat-temperature lamp. Animals were not treated with any topical or local anesthetics post-operatively.

Assessment of pain in Chung model rats was performed by applying a light tactile stimulus (Von Frey hair) to the affected surgical paw as follows. A 50% pain threshold was established by applying the Von Frey hair in an up-and-down manner to the plantar surface of the surgical paw with just enough force to bend them. A positive response was recorded if the paw was withdrawn sharply. The 50% paw withdrawal threshold was determined using the method of Dixon et al., *Ann. Rev. Pharmacol. Toxicol.* 20:441-462 (1980). The post-drug threshold was compared to the pre-drug threshold, and the precent reversal of tactile sensitivity calculated based on a normal threshold of 15.1 grams. The results were expressed as % allodynia reversal, reflecting the percentage reversal of pain threshold relative to a normal rat (100%).

Male Sprague-Dawley rats that were not subject to surgery were used for assessment of sedative effects. Rats were weighed and compound administered by intravenous or intraperitoneal injection or given orally at the indicated dose. At a predetermined time point 5 to 30 minutes following injection, the animal's activity was determined automatically by placing the rat in a digicom analyzer chamber (Omnitech Electronic). Total activity was analyzed as described above.

B. Diverse Structural Classes of Peripherally Administered α-2B/C-Selective Compounds With Minimal α-2A Activity Relieve Pain α-adrenergic agonists of diverse structural classes with minimal α-2A agonist activity were administered peripherally and assayed for the ability to relieve pain in the Chung rat model. Table 2 shows the results obtained with the thione Compound 3, the imidazolone Compound 4, the thiazole Compound 5, the oxazole Compound 6, the thiourea Compound 7, and the 4-imidazole Compound 14. Each of these compounds, while structurally diverse, are β2-B/C selective α-adrenergic agonists having minimal α-2A agonist activity. As an example, Compound 14 is an α-2B selective agonist having minimal α-2A agonist activity yet having significant α-1 agonist activity.

As shown in Table 2, peripheral administration of each of the diverse compounds produced analgesic activity at a dose that did not reveal significant sedative effects. Conversely, diverse α-adrenergic agonists having α-2A activity were assayed and did not produce analgesia separable from sedation when administered by intraperitoneal injection. These results corroborate that diverse structural classes of α-adrenergic agonists having minimal α-2A activity are characterized by the ability to produce peripherally mediated analgesia without concomitant sedation.

TABLE 2

Peak Allodynia reversal in Chung rat model

| COMPOUND | Peak allodynia reversal (dose) | Sedative effect (1 mg/kg) |
| --- | --- | --- |
| COMPOUND 3 | 81% +/− 10% (300 µg/kg) | NS* |
| COMPOUND 4 | 80% +/− 6.5% (100 µg/kg) | NS* |
| COMPOUND 5 | 77% +/− 8.3% (30 µg/kg) | NS* |
| COMPOUND 6 | 92% +/− 5.2% (100 µg/kg) | NS* |
| COMPOUND 7 | 60% +/− 8.0% (3 µg/kg) | NS* |
| COMPOUND 14 | 77% +/− 6.2% (100 µg/kg) | NS* |

*No significant effect.

A full comparison of the sedative and analgesic dose response curves for clonidine and Compound 3 was performed using a single intraperitoneal dose from 20 µg/kg to 100 µg/kg for clonidine and 1 to 1000 µg/kg for Compound 3. The percentage of allodynia reversal and the reduction in total activity were determined as described above. As shown in FIG. 4C, clonidine sedation occurred at lower doses than the doses that produced analgesia. In particular, clonidine was extremely sedating at the 100 µg/kg dose that produced significant analgesia. These results demonstrate that the analgesia resulting from peripheral dosing with clonidine is not separable from sedation. In contrast, the results shown in FIG. 4D demonstrate that Compound 3 produced significant analgesia without producing sedation. Specifically, sedation did not occur at doses 100-fold greater than those producing a robust reversal of allodynia. These results demonstrate that an α-2B adrenergic agonist with minimal α-2A agonist activity can produce a 80% allodynia reversal without concomitant sedation.

In sum, these results demonstrate that non-selective α-adrenergic agonists with unremarkable analgesic activity following systemic dosing can be turned into very effective agents that produce peripheral analgesia without concomitant sedation when combined with an agent that prevents activation of the α-2A receptor. These results also demonstrate that the analgesic action of selective α-2 agonists having only minimal α-2A receptor agonist activity is distinct from the analgesic action of α-adrenergic agents previously described.

EXAMPLE IV

Long-Term Relief of Chronic Pain

This example demonstrates that α-adrenergic agonists with minimal α-2A activity can mediate a long-term reversal of the chronic pain phenotype.

A. Long-term Pain Relief in Chung Model Rats

Structurally distinct α-adrenergic agonists were assayed for the ability to produce prolonged relief of chronic pain in Chung model rats following extended dosing. In particular, Chung model animals were dosed for seven days using a subcutaneous osmotic minipump with vehicle control or 0.1 mg/kg/hour of the following α-adrenergic agonist with minimal α-2-A activity: Compound 8, Compound 9, Compound 3 or Compound 4. Pain relief was observed during the period of drug treatment; for example, Compound 8 alleviated the allodynia 90-100%, and Compound 9 alleviated the allodynia 60-80%, as shown in FIG. 5A. Notably, the analgesic effects of these compounds as well as Compound 3 and Compound 4 continued for over a month after treatment was concluded. Treated animals exhibited behavioral signs of being cured, differing from untreated or vehicle-treated rats in that they no longer guarded the surgical paw and placed this paw flat on the bottom of their cage.

Prolonged pain relief also was observed following three days of oral dosing. Chung model rats were administered three doses of 0.3 mg/kg Compound 8 by oral gavage between 8 a.m. and 6 p.m. for three consecutive days. A 70-80% reversal of allodynia was achieved, and allodynia did not increase during a more than three week period of follow-up testing. These results indicate that, in contrast to the relatively short duration of pain relief obtained following a single intraperitoneal or oral dose of an α-2B/C agonist such as Compound 8, a prolonged analgesic effect results from repeated dosing with α-2B/C selective agonists with minimal α2-A agonist activity.

Chung surgeries were performed, and pain assessed as described above. Drugs administered via osmotic minipump were delivered as follows. ALZET (Cupertino, Calif.) minipumps (Model #1007D) were implanted subcutaneously on the rats' back between the shoulder blades. Pumps were filled with test solution prior to surgery, which was performed with aseptic procedures and sterilized surgical instruments. After anesthetization with isoflorane and midline incision between the shoulder blades through the muscle, a subcutaneous pocket was exposed. The minipump was inserted into the exposed pocket, before stapling the wounds closed and allowing animals to recover under a warming light.

ALZET osmotic minipumps (model 1007D) hold a total volume of 100 µl and delivered drug at the set rat of 0.5 µl per hour the indicated time period. Drugs were administered at the indicated rate, typically 100 µg/hr/kg, dissolved in 50% DMSO, with the concentration of drug in the pump varied depending on animal weight. Pumps were removed seven days following pump insertion.

B. Analgesic Effects Extend Beyond the Time Drug Persists in the Plasma

Figure 5:
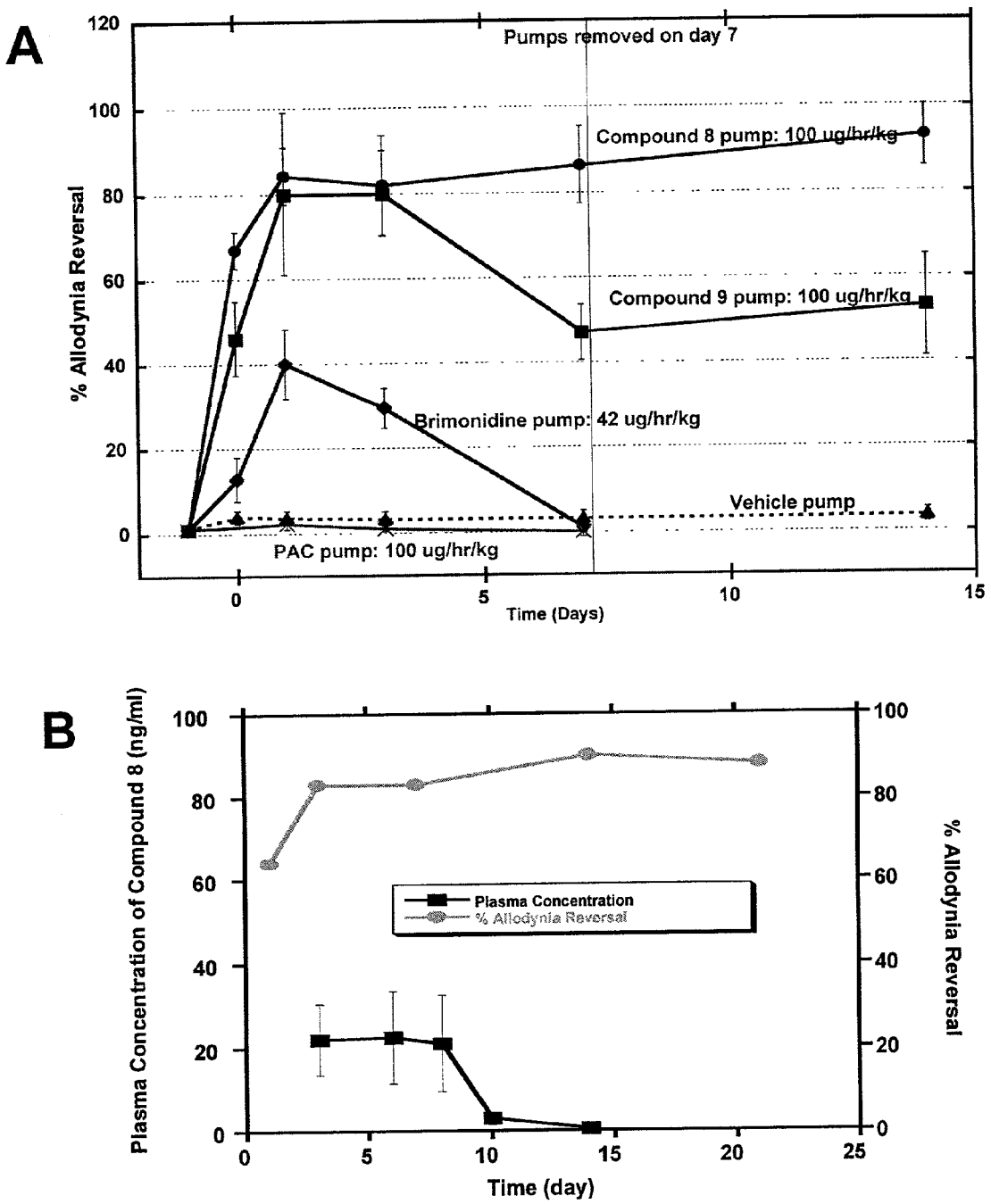
FIG. 5 shows that analgesic activity of an α-adrenergic agonist with minimal α-2A agonist activity continues in the absence of plasma drug levels. (A) Chung model rats were administered Compound 8, Compound 9, brimonidine, para-amino-clonidine or vehicle for seven days via osmotic minipump at the indicated concentrations. The percentage allodynia reversal was measured over the course of 15 days from the time of osmotic minipump implantation. The results obtained with Compounds 8 and 9 were significant with a p value of <0.05. (B) Chung model rats were administered 0.1 mg/hr/kg drug Compound 8 for seven days via osmotic minipump. The plasma concentration (ng/ml) of Compound 8 and the percentage of allodynia reversal (% MPE) at the same time point were measured on the indicated days following pump implantation.
Figure 6:
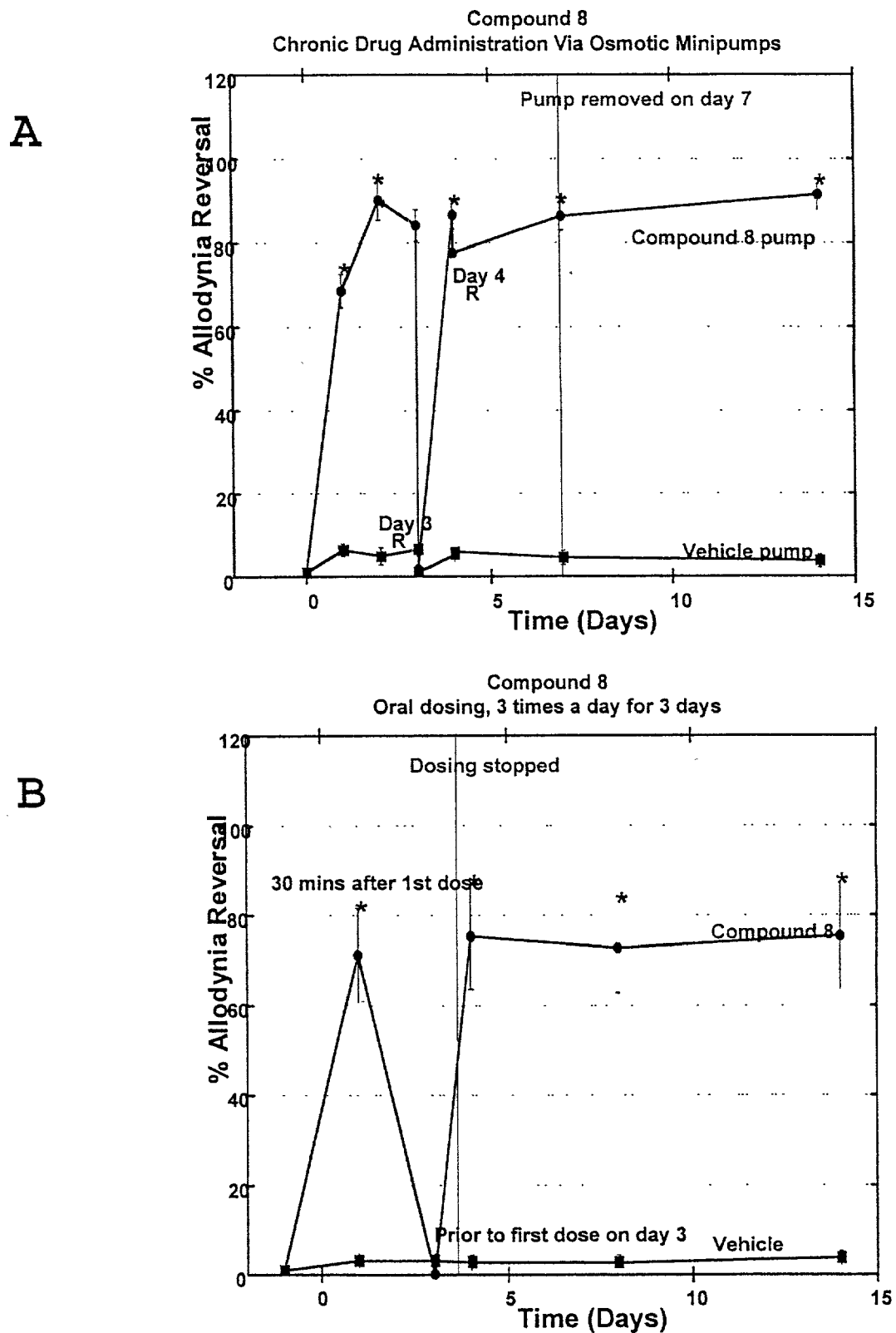
FIG. 6 shows that reversal of allodynia does not require ongoing receptor activation after several days dosing with Compound 8. The percentage of allodynia reversal in Chung model rats is indicated at various days after initiation of Compound 8 drug treatment. (A) Treatment with 0.1 mg/hr/kg Compound 8 via osmotic minipump for seven days. On days 3 and 4, measurements were made prior to and 30 minutes following a 0.3 μg/kg intraperitoneal dose of rauwolscine (R). (B) Treatment with 0.3 mg/kg Compound 8 by oral dosing three times a day for three days. Measurements were made after or prior to the first dose of the day as indicated. Measurements continued for 11 days after dosing was completed. Asterisks indicate a significant result with a p value <0.05.

To determine whether the persistent reversal of allodynia was due to the continued presence of drug in the animals, rats were treated for seven days using a subcutaneous osmotic minipump with 0.1 mg/kg/hour Compound 8. Plasma concentrations of Compound 8 were sampled on days 3, 6, 8, 10 and 14 following pump insertion and determined by liquid chromatography-mass spectrometry/mass spectrometry (LC-MS/MS). As shown in FIG. 5, minimal drug levels were detected on day 10, and no drug remained in the plasma by day 14. These results indicate that pain relief can be achieved following extended dosing, even in the absence of plasma drug levels.

C. Analgesia Does not Require Receptor Activation Following Extended Dosing

Chung model rats treated with Compound 8 for seven days by osmotic minipump or for three days by oral gavage consistently exhibited prolonged relief from allodynia. The α-2 antagonist, rauwolscine, was assayed for the ability to inhibit this anti-allodynic action at various time points. Notably, as shown in FIG. 6A, rauwolscine at 0.3 µg/kg i.p. inhibited the analgesic activity of Compound 8 when injected on the third day of treatment but not on the fourth day.

Similarly, oral dosing was performed three times a day with 0.3 mg/kg Compound 8 for three days. The morning assessment of analgesia was performed approximately 14 hours after the last dose. Chung model rats exhibited complete tactile allodynia on days 2 and 3, when assayed prior to the first Compound 8 dose of the morning. However, as shown in FIG. 6B, on the morning of day 4, allodynia was dramatically reduced and it did not reappear during the time frame of testing.

These results indicate that, following several days of dosing with an α-adrenergic agonist with minimal α-2A activity, drug is no longer required for continued analgesic activity. These results further indicate that receptor activation sufficient for a prolonged analgesic effect can be continuous or intermittent.

D. Long-Term Pain Relief is not a General Property of Analgesic agents

A variety of drugs that relieve acute pain were assayed for long-term pain alleviation in Chung rats. In particular, the anti-convulsant, gabapentin (3 mg/kg, oral, TID, three days); the anti-depressant, amitriptyline (0.1 mg/kg/hour, infusion minipump, seven days); and two non-selective α-adrenergic agonists with α-2A activity, brimonidine (0.04 mg/kg/hour, infusion minipump, seven days) and Compound 1 (0.1 mg/kg/hr, infusion minipump, seven days), were administered to Chung model rats at doses that acutely alleviated tactile allodynia in this model. In all cases, the allodynia returned completely prior to or following cessation of treatment.

Figure 7:
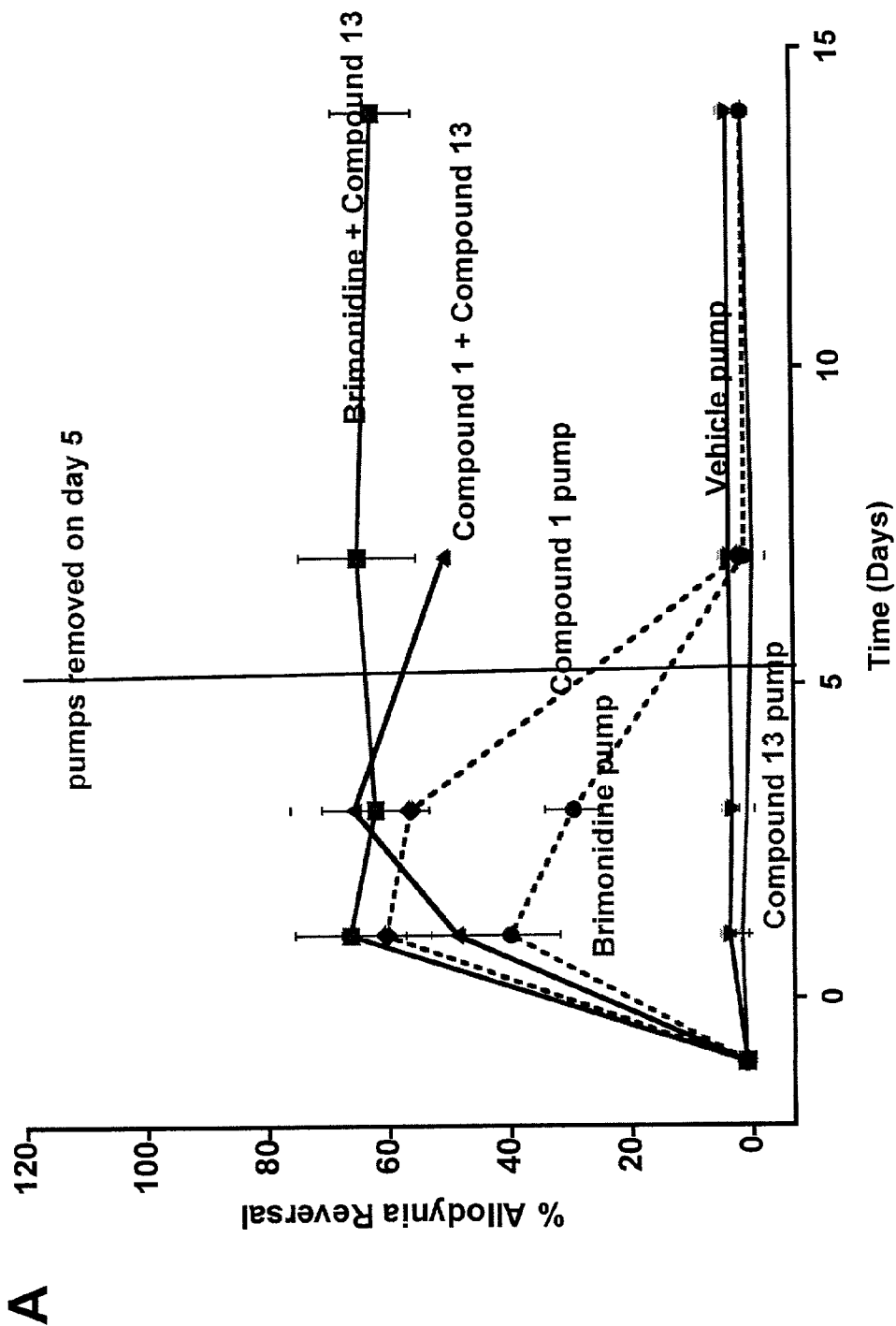
FIG. 7A shows that pan-α-2 agonists can produce long-term pain relief when combined with a selective α-2A antagonist. Drugs were administered for five days via osmotic minipump at the following doses: brimonidine (42 μg/kg/hr); Compound 1 (0.1 mg/kg/hr); and Compound 13 (8 μg/kg/hr). Each compound and vehicle was administered alone; brimonidine and Compound 1 also were administered together with Compound 13. The percentage allodynia reversal was determined at various days from the start of dosing. The results obtained after day 5 with the combination of brimonidine and Compound 13 or Compound 1 and Compound 13 were significant with a p value <0.05.
FIG. 7B shows that Compound 8 produces long-term pain relief of cold allodynia in the Bennett model. Animals were treated for four days with 0.1 mg/hr/kg Compound 8 or saline by osmotic minipump, which was removed on day 4. Paw withdrawal duration over a five minute period (in seconds) is shown on the indicated days following initiation of drug treatment.
Figure 7:
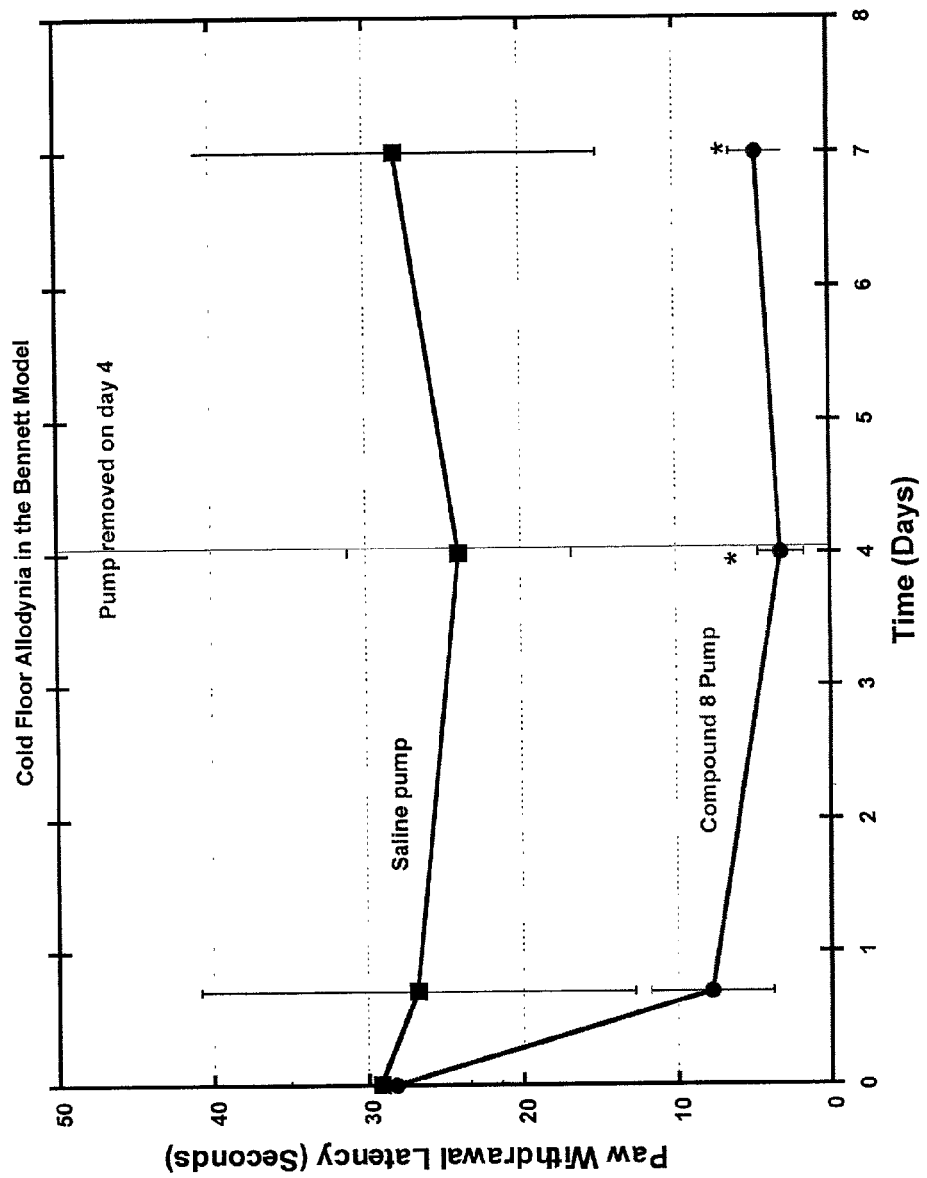
Figure 8:
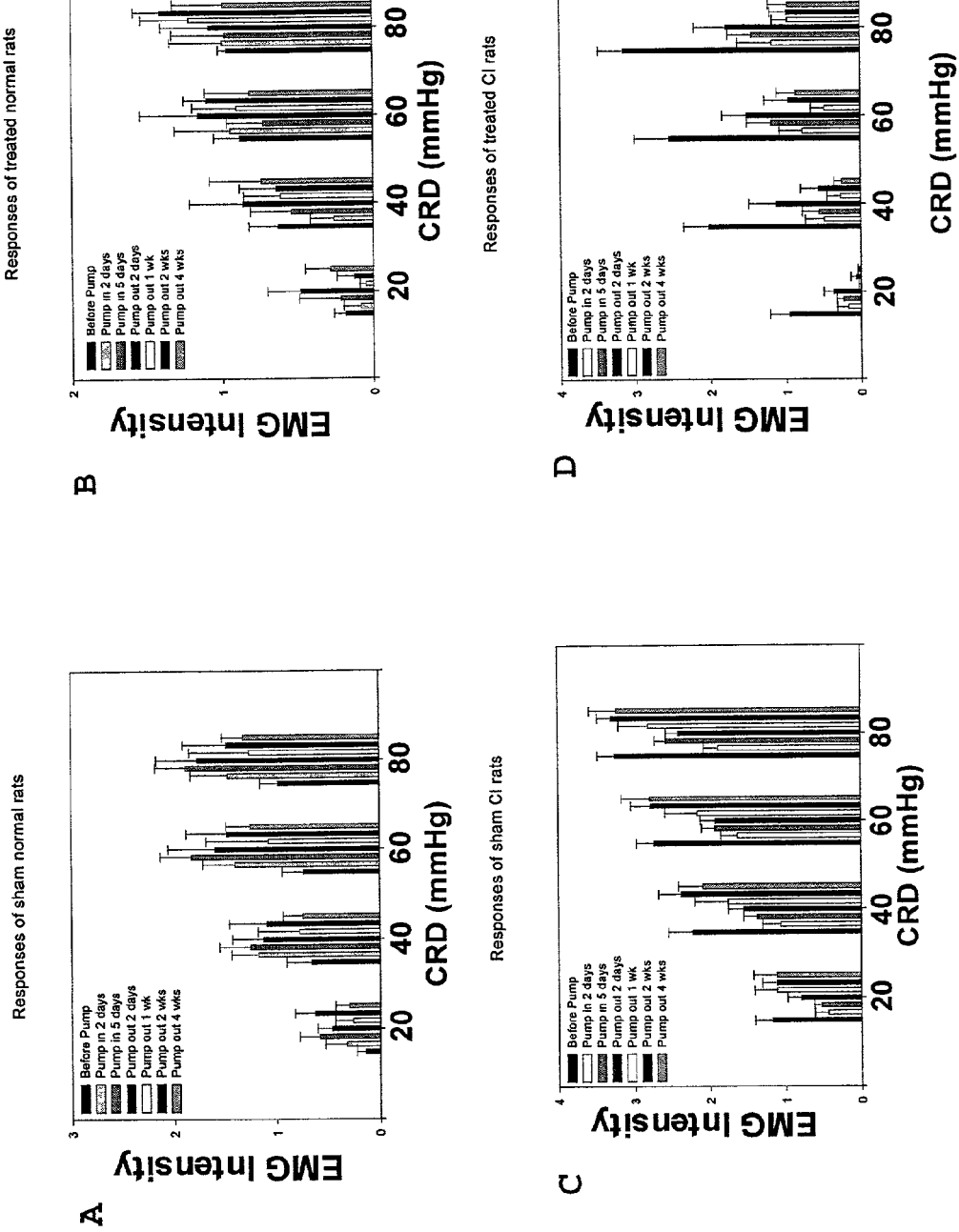
FIG. 8 shows that Compound 8 produces long-term pain relief in a rat model of irritable bowel syndrome. Rats were treated for seven days by osmotic minipump; the abdominal withdrawal reflex to a series of colorectal distensions (CRDs) was measured by electromyography prior to, during, and subsequent to treatment. (A) Normal rats treated with 50% DMSO vehicle. (B) Normal rats treated with Compound 8 at 0.1 mg/hr/kg. (C) Sensitized rats treated with 50% DMSO vehicle. (D) Sensitized rats treated with Compound 8 at 0.1 mg/hr/kg. CRD, colorectal distension

However, as shown in FIG. 7A, when brimonidine or Compound 1 was co-administered with the α-2A selective antagonist, Compound 13 at 0.2 mg/kg/day, greater analgesia was observed during the dosing period, and this analgesic effect continued after completion of drug administration. These results indicate that an α-adrenergic agonist with minimal α-2A agonist activity or a non-selective α-adrenergic agonist administered in conjunction with a selective α-2A antagonist can produce a long-lasting analgesic effect after extended dosing that cannot be achieved by similar compounds having α-2A agonist activity.

E. Long-Term Pain Relief in the Bennett Partial Sciatic Nerve Ligation Model

The α-2B/C selective agonist Compound 8 was tested in a second rat nerve injury model of neuropathic pain, the Bennett partial sciatic nerve ligation model. This rat model produces a peripheral mononeuropathy with disorders of pain sensation similar to those seen in man (Bennett and Xie, Pain 33:87-107 (1988)). In the Bennett model, nerve injury is created by loosely tying constrictive ligatures around the sciatic nerve, causing degeneration of nerve distal to the constriction. Allodynia and hyperalgesia are produced by the constriction injury in addition to spontaneous pain (Bennett and Xie, supra, 1988). In particular, cold allodynia, the sensation of pain from cold stimuli, is one manifestation of altered pain sensation: Bennett model animals frequently lift the paw of the surgical limb off the cold surface, in contrast to control animals.

Compound 8 was administered by osmotic minipump over a period of four days. As shown in FIG. 7B, cold allodynia was completely alleviated both during the four day treatment period and for the more than three week testing period following pump removal. These results indicate that α-2 adrenergic agonists with minimal α-2A agonist activity such as Compound 8 have analgesic properties applicable to different types of neuropathic pain.

Bennett surgeries of about 20 minute duration were performed as follows. Male Sprague-Dawley rats (approximately 250-300 grams) were anesthetized by isoflurane/oxygen inhalation. After preparing the surgical site by shaving and application of betadine, an incision was made slightly to the left of midline over the pelvic girdle. Slightly caudal and ventral to the left hip joint, a faint separation of muscle groups was visualized, and a small (approximately 10 to 25 mm) incision made just below the separation of the muscle groups. Muscle was bluntly separated until the sciatic nerve was visible parallel to the length of the femur. A 7 to 10 mm length of sciatic nerve was cleared carefully from underlying tissue, before loosely tying four ligatures (6/0, silk) around the sciatic nerve with approximately 1 mm spacing between ligatures. L igatures were tied so that the diameter of the nerve was slightly constricted and blood flow retarded but not arrested. Excess suture material was trimmed, the muscle groups approximated, and the skin incision closed with wound clips, which were removed 10-14 days post surgery. Animals were not administered any post-operative topical or local anesthetic.

Chronic drug administration was achieved via an osmotic minipump, which was implanted subcutaneously on the back of the rat one week after the Bennett surgery as described above. Assessment of pain response in Bennett animals was performed seven days after surgery as follows. To assess response to thermal stimuli, rats were placed under a clear plastic chamber (18 cm×29 cm×12.5 cm) on a chilled (0-4° C.) metal floor, which is not noxious to a normal animal, and the time that the surgical paw was raised off of the cold floor recorded over a 5 minute period. On the day of experiment, test drug was administered (IP or PO in 1 ml/kg volume in a dose ranging from 1 to 1000 ug/kg) without anesthetization. In some cases, animals were used for subsequent experiments over a 3 month period after receiving at least three days rest in between studies.

F. Long-Term Pain Relief in a Model of Irritable Bowel Syndrome

This example demonstrates that an α-2 adrenergic agonist with minimal α-2 activity such as Compound 8 alleviates pain in a rat model of chronic visceral hypersensitivity.

A well-accepted model of chronic visceral hypersensitivity is described in Al-Chaer et al., Gastroenterology 119: 1276-85 (2000). In brief, colons of neonatal male Sprague Dawley rats were sensitized by repeated inflation of a colonic balloon on postnatal days 8 to 21, with colonic balloons inflated to pressures ranging from 20-80 mm Hg. Three months later, the abdominal withdrawal reflex (AWR) response of the adult rats to graded colorectal distension (CRD) was quantified by electromyography (EMG) recording from the abdominal wall muscle. Sensitized rats exhibited both allodynic pain and hyperalgesia, showing an exaggerated response to normally nonpainful levels of balloon inflation (20 mm Hg) as well as to painful stimuli (40-80 mm Hg), which are visceral pain symptoms similar to those in human patients with irritable bowel syndrome. Unsensitized animals exhibited very little response to balloon inflation of 20 mm Hg and a mild response up to an EMG intensity unit of 1, with CRD up to 80 mm Hg. Each level of CRD was administered for 20 seconds every four minutes and repeated for a total of five times.

Groups of 8-10 normal and sensitized adult Sprague Dawley rats (approximately 3 months old) were implanted with subcutaneous minipumps to deliver either 50% DMSO or Compound 8 in 50% DMSO at a dose of 100 ug/kg/hr over a period of 7 days. The abdominal withdrawal reflex to a graded series of colorectal distensions (20, 40, 60, 80 mm Hg) was measured by abdominal EMG recording prior to pump implantation, on days 2 and 5 of the subcutaneous infusion, and 2 days, 1 week, 2 weeks, and 4 weeks after the pumps were removed.

As shown in FIGS. 8A and 8B, the EMG response following treatment of non-sensitized control rats with 50% DMSO vehicle (FIG. 8A) or Compound 8 (FIG. 8B) did not change significantly from pre-treatment levels; EMG intensity ranged from approximately 0 to about 1.5. In contrast, the EMG response in the sensitized rats was much greater, ranging approximately from intensities of 1 to 3.5 (see FIGS. 8C and 8D); this increased pain response in the sensitized rats was not reduced following treatment with vehicle as shown in FIG. 8C. In contrast, during and following the treatment with Compound 8, the increased EMG response in the sensitized rats was completely alleviated. As shown in FIG. 8D, pain was reduced to 0 to 1.5, which is the level seen in non-sensitized rats. Furthermore, colorectal allodynia and hyperalgesia did not return during the time period tested, which was 4 weeks following cessation of drug treatment.

These results demonstrate that an α-2 adrenergic agonist with minimal α2-A activity can be used for the long-term relief of colorectal pain such as irritable bowel syndrome pain. These results further indicate that the observed analgesic effects are not specific to peripheral neuropathic pain and that an α-2 adrenergic agonist with minimal α2-A activity or an α-2 adrenergic agonist administered in conjunction with a selective α2-A antagonist can be used to treat a variety of types of acute and chronic pain such as neuropathic, visceral, inflammatory, post-surgical and cancer pain.

EXAMPLE V

Peripheral α-Adrenergic Agonist Analgesic Activity is Mediated by the α-2B Receptor This example demonstrates that peripheral α-adrenergic agonist analgesic activity can be mediated by activation of the α-2B receptor.

In wild type mice, an intraperitoneal dose of clonidine (500 ug/kg) alleviated sulprostone-induced tactile allodynia but produced concomitant sedation. In contrast, intraperitoneal Compound 3 (100 ug/kg), an α-adrenergic agonist with minimal α-2A agonist activity, alleviated sulprostone-induced tactile allodynia without concomitant sedation. The analgesic effect of these doses of clonidine and Compound 3 was determined in α-2B heterozygous (−/+) and homozygous (−/−) knockout mice using the smallest Von Frey hair at 1.65 grams of force. At this force, the smallest Von Frey hair does not evoke a pain response in untreated α-2B knockout mice nor in their wild type litter-mates. Allodynia was assessed and ranked as described above.

Figure 9:
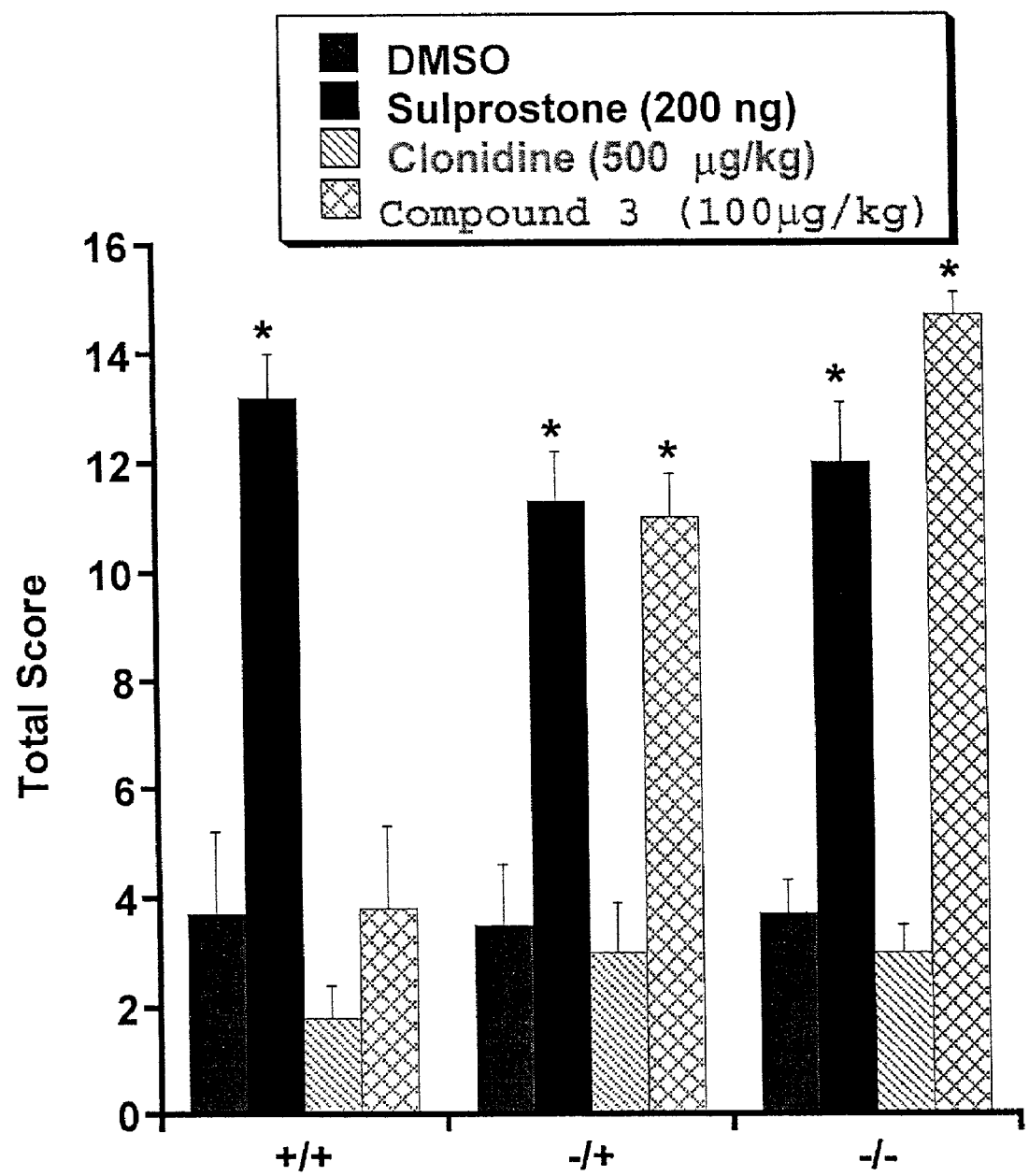
FIG. 9 shows the analgesia obtained with sulprostone-sensitized α-2B knockout mice. Wild type (+/+); heterozygous (+/−) or homozygous (−/−) α-2B knockout mice were treated with intrathecal vehicle (DMSO), intrathecal sulprostone, sulprostone with intraperitoneal clonidine, or sulprostone with intraperitoneal Compound 3. The total pain score in six mice was determined. Asterisks indicate a significant result with a p value <0.05.

As shown in FIG. 9, clonidine alleviated the analgesia in both heterozygous and homozygous α-2B knockout strains, with no difference from its effect in wild type mice; again, the analgesia was accompanied by sedation. In contrast, Compound 3 was not analgesic in either the heterozygous or homozygous α-2B knockout mice (FIG. 9). Similar results were obtained with other compounds. In particular, like clonidine, the α-adrenergic pan-agonist, brimonidine, was analgesic in α-2B knockout mice, while Compound 8, an α-adrenergic agonist with minimal α-2A agonist activity, failed to show analgesic activity in heterozygous or homozygous α-2B knockout mice.

These results demonstrate that the mechanism of analgesia of α-adrenergic agonists with minimal α-2A agonist activity is distinct from the mechanism of analgesia of α-adrenergic pan-agonists. These results further indicate that peripheral α-adrenergic analgesic activity is mediated by activation of the α-2B receptor.

EXAMPLE VI

Characterization of α-2B and α-2B/C Selective α-Adrenergic Agonists

This example describes the receptor subtype selectivity, oral analgesic activity and absence of sedative and cardiovascular side effects associated with Compounds 3, 11 and 4.

A. Receptor Subtype Selectivity Profiles of Compounds 3, 11 and 4

As shown in Table 3, each of Compounds 3, 11 and 4 are selective for α-2 adrenergic receptors, with little or no activity at α-1 receptors. Furthermore, each of these compounds is a α-2B/C selective compound exhibiting no detectable activity at the α-2A receptor in the in vitro RSAT assay. Compound 4 was selective for the α-2B receptor, exhibiting more than 10-fold greater activity at the α-2B receptor than the α-2C receptor. Compound 3 was specific for the α-2B receptor as it was characterized by about 100-fold greater activity at the α-2B receptor than the α-2C receptor.

TABLE 3

α-Adrenergic receptor selectivity profile

| Compound/class | RSAT activity (nM)/ % efficacy | | | | | |
|---|---|---|---|---|---|---|
| | 2A | 2B | 2C | 1A | 1B | 1D |
| Compound 3 thione/racemate | NA | 24 (90%) | >2000 | >2000 | NA | >2000 |
| Compound 11 thione | NA | 42 (80%) | 247 (0.3) | 1713 | NA | >2000 |

TABLE 3-continued

α-Adrenergic receptor selectivity profile

| Compound/class | RSAT activity (nM)/ % efficacy | | | | | |
|---|---|---|---|---|---|---|
| | 2A | 2B | 2C | 1A | 1B | 1D |
| Compound 4 imidazolone | NA | 15 (100%) | 202 (0.5) | NA | NA | >2000 |

NA = not active (EC$_{50}$ ≥ 10,000)

B. Oral Analgesic Activity of Compounds 3, 11 and 4

Figure 10:
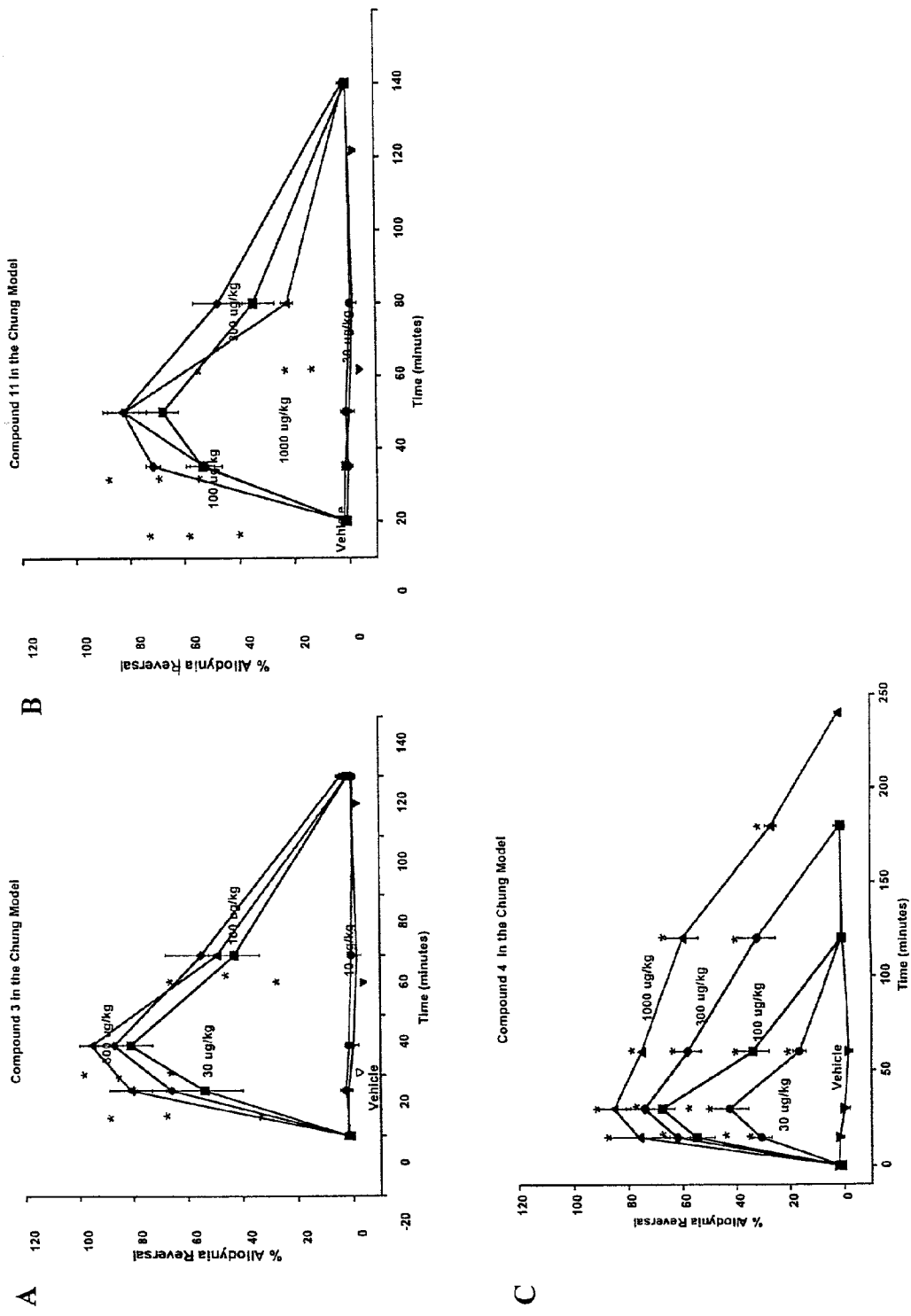
FIG. 10 shows the peripheral analgesic effects of Compound 3, Compound 11 and Compound 4 at various oral doses of drug in Chung model rats. (A) A single oral dose of 10 μg/kg, 30 μg/kg, 100 μg/kg or 300 μg/kg Compound 3. (B) A single oral dose of 30 μg/kg, 100 μg/kg, 300 μg/kg or 1000 μg/kg Compound 11. (C) A single oral dose of 30 μg/kg, 100 μg/kg, 300 μg/kg or 1000 μg/kg Compound 4. Asterisks indicate a significant result with a p value <0.05.

Various concentrations of Compounds 3, 11, and 4 were administered orally to Chung model rats as described above. As shown in FIG. 10A, 30 μg/kg oral Compound 3 resulted in 70-100% allodynia reversal. The analgesic effect was seen quickly, in less than 20 minutes. Moreover, when administered as a single oral dose, the effect was transient with analgesia essentially gone by 2 hours following administration. FIG. 10B shows that oral Compound 11 also alleviated pain in the Chung rat model. A dose of 0.1 mg/kg was sufficient to reduce the allodynia by about 60-90%. Again, the analgesic effect was gone by 2 hours post-administration following a single oral dose. As shown in FIG. 10C, Compound 4 exhibited linear dose-responsiveness in alleviating pain: a dose of 30 μg/kg was sufficient for an analgesic effect, and, at 0.3 mg/kg Compound 4, about 60-80% of the allodynia was reversed. At 1 mg/kg, the allodynia was reversed to a greater extent, and the pain relief was of longer duration. However, essentially no pain relief was observed after four hours, even at the highest dose (FIG. 10C). These results corroborate that α-adrenergic agonists with minimal α-2A activity can act as analgesic agents when administered orally.

C. Long-Term Pain Relief With Compounds 3, 11 and 4

Figure 11:
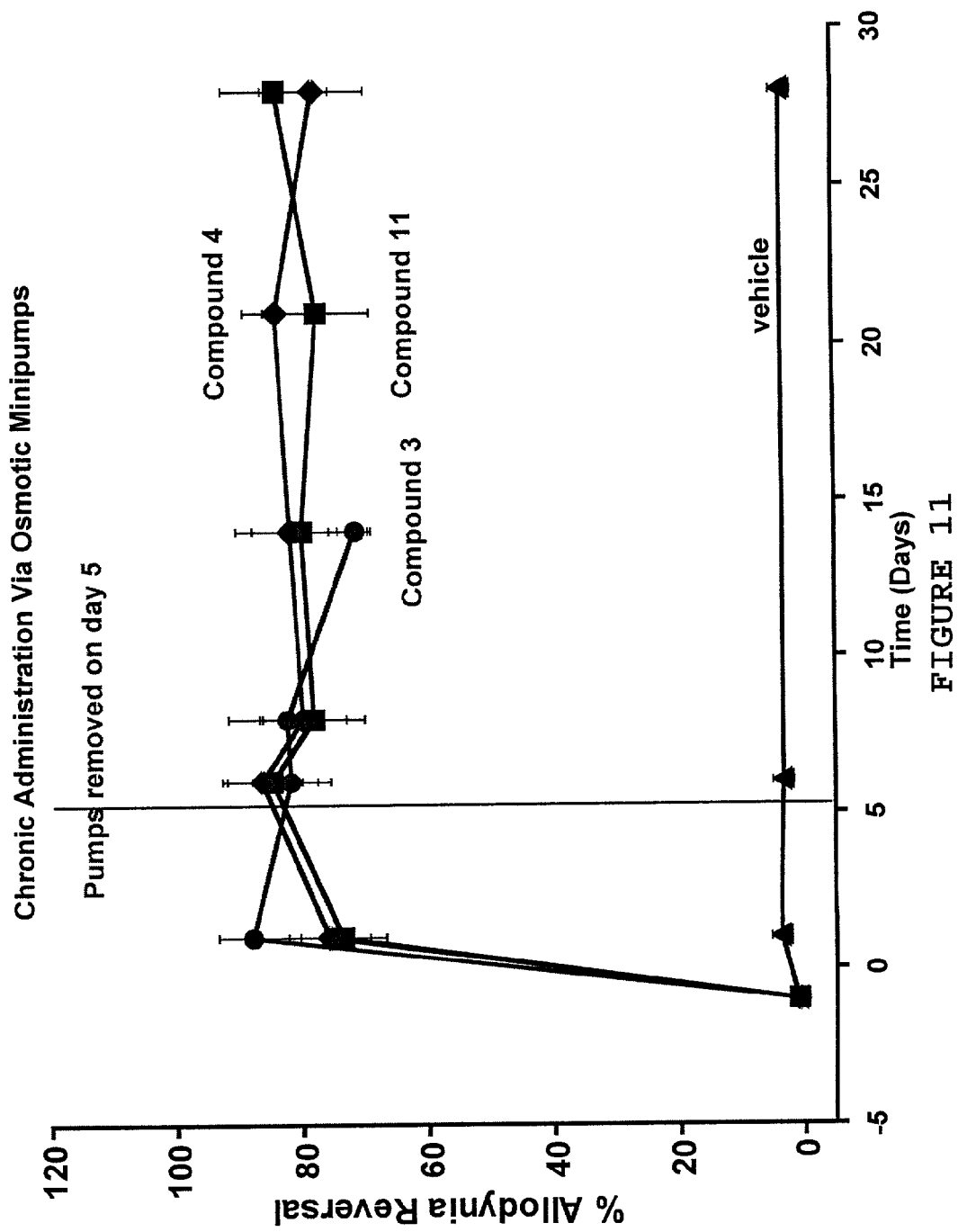
FIG. 11 shows long-term reversal of allodynia in Chung model rats following 5 days of treatment by osmotic minipump with 0.1 mg/kg/hour Compound 3, Compound 4 or Compound 11. The results obtained for all three compounds were significant, with a p value <0.05.

Compounds 3, 11, and 4 were administered for five days via osmotic minipump. Drug administration was discontinued on day 5, at which time the minipumps were removed. Allodynia was assayed over a period of about a month. As shown in FIG. 11, about 80% allodynia reversal was achieved by each of the three compounds. Furthermore, the analgesic effect of Compounds 11, and 4 was maintained at essentially the same level over the entire four week test period. These results indicate that Compounds 3, 11 and 4 are effective analgesic agents for long-term pain relief and further corroborate that, following extended dosing, α-adrenergic agonists with minimal α-2A activity can be used to treat chronic pain.

D. Side Effect Profiles of Compounds 3, 11 and 4

Compounds 3, 11 and 4 were administered intraperitoneally at 1 mg/kg, which is higher than the dose required to produce peak allodynia reversal (see Table 2). Sedative effects were assayed as above. In addition, these compounds were assayed for cardiovascular side effects in monkeys at 0.5 mg/kg intravenous administration, or 3 mg/kg orally, and Compound 3 was assayed for cardiovascular effects in rats. The lack of α-2 antagonist activity of a 3 mg/kg dose was assessed by testing reversal of the sedative effects of clonidine coadministered intraperitoneally at a 0.1 mg/kg dose ("sedation reversal").

As shown in Table 4, no significant sedative or cardiovascular side effects were observed for Compound 3, Compound 11 or Compound 4 at the indicated doses, which were higher than the doses required to achieve 60-90% allodynia reversal.

TABLE 4

Sedative and Cardiovascular side effects

| Compound | Rat sedation (i.p.) | Sedation reversal (i.p.) | Monkey cardiovascular (BP, HR) | Rat cardiovascular (BP, HR) |
|---|---|---|---|---|
| Compound 3 | NS* 1 mg/kg | NS 3 mg/kg | NS 0.5 mg/kg iv | NS 3 mg/kg i/a |
| Compound 11 | NS 1 mg/kg | NS 3 mg/kg | NS 0.5 mg/kg iv NS 3 mg/kg po | — |
| Compound 4 | NS 1 mg/kg | NS 3 mg/kg | NS 3 mg/kg po | — |

*No significant effect

Cardiovascular effects were assayed in approximately six cynomolgus monkeys weighing roughly 4 kg with the indicated dose and compound administered by intravenous or intraperitoneal administration. Monkeys were weighed, and the appropriate concentration of a 0.1 ml/kg intravenous dosing solution or a 1.0 ml/kg intraperitoneal dosing solution injected. Intravenous injections were via the cephalic arm vein. Blood pressure and heart rate measurements were made prior to and at 0.5, 1, 2, 4 and 6 hours after drug administration with a BP 100S automated sphygmomanometer (Nippon Colin; Japan). Cardiovascular effects were determined in rats as described in Altman et al., *Mol. Pharm.* 56:154-161 (1999).

These results indicate that the analgesic effects of α-adrenergic agonists with minimal α-2A activity can be achieved without significant sedative or cardiovascular side effects.

EXAMPLE VII

Analgesic Activity of Enantiomers of Compounds 3 and 4

This example demonstrates that enantiomers of the α-adrenergic agonists with minimal α-2A agonist activity can exhibit differential analgesic activity.

Figure 12:
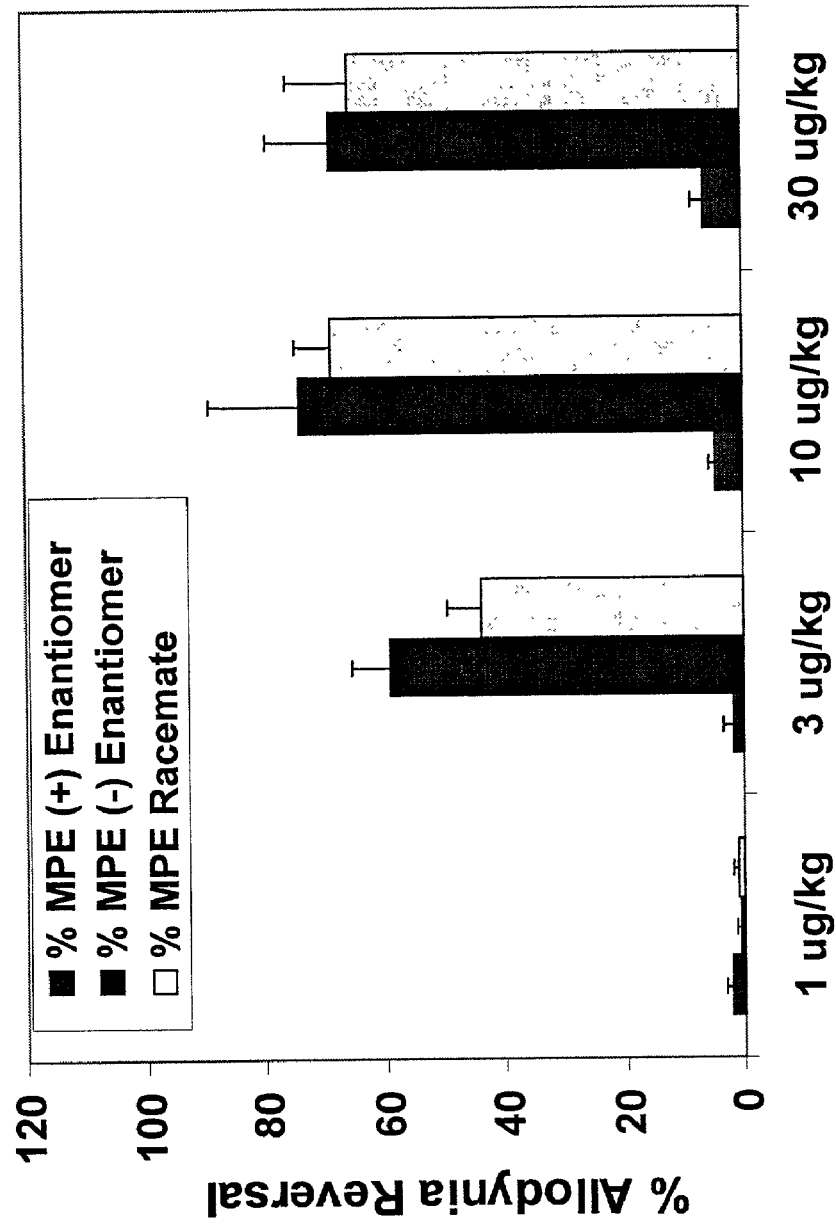
FIG. 12 shows differential analgesic activity of enantiomers of Compounds 3 and 4. (A) Percentage allodynia reversal obtained with enantiomers and parent racemate of Compound 3 at the indicated intraperitoneal doses. (B) Percentage allodynia reversal obtained with enantiomers and parent racemate of Compound 4 at the indicated intraperitoneal doses. The results obtained were significant, with a p value <0.05, where an analgesic effect was observed.
Figure 12:
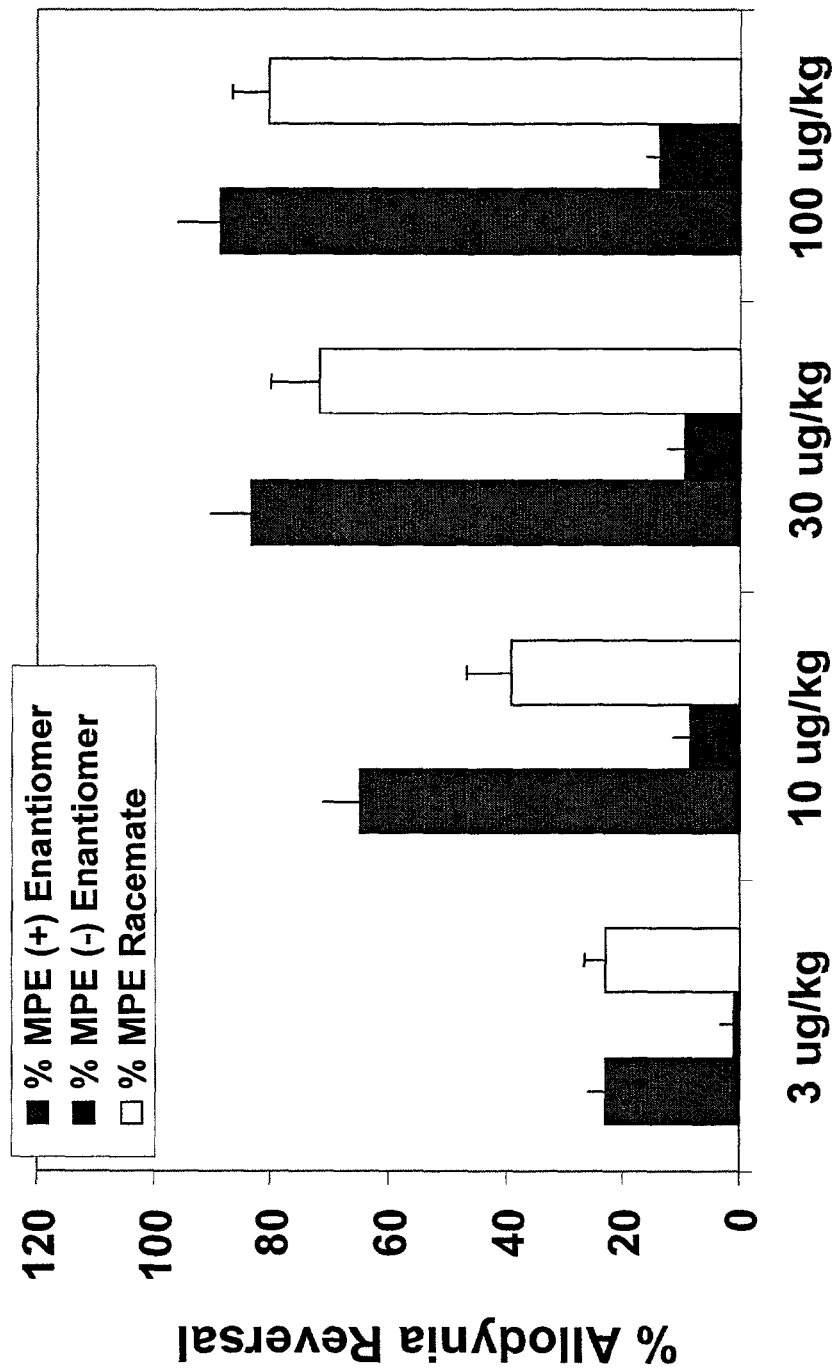

Enantiomers of Compound 3 and Compound 4 were prepared as described above in Example I and designated Compound 10 and Compound 12, respectively. Both enantiomers and the parent racemate were assayed for analgesic activity following intraperitoneal administration to Chung model rats. As shown in FIG. 12A, allodynia reversal was obtained with the (−) enantiomer of Compound 3 (designated Compound 10) but not with the (+) enantiomer. The (−) enantiomer was as effective as parent racemic mixture in relieving pain.

Similarly, FIG. 12B shows the percentage of allodynia reversal obtained in Chung model rats given various concentrations of each enantiomer and parent agonist Compound 4 by intraperitoneal administration. As shown in the figure, the (+) enantiomer (designated Compound 12) was at least as effective as the parent compound in reducing allodynia at all doses tested.

These results demonstrate that enantiomers of α-2B/2C selective agonists can exhibit differential analgesic activity and further indicate that the (−) enantiomer of Compound 3 and the (+) enantiomer of Compound 4 are effective analgesic agents.

All journal article, reference and patent citations provided above, in parentheses or otherwise, whether previously stated or not, are incorporated herein by reference in their entirety.

Although the invention has been described with reference to the examples provided above, it should be understood that various modifications can be made without departing from the spirit of the invention. Accordingly, the invention is limited only by the claims.

We claim:

1. A method for the long-term relief of chronic pain in a subject, comprising activating in said subject an analgesic α-adrenergic receptor in the absence of α-2A receptor activation over a period of at least three days,
    activating, no sooner than three days after the analgesic α-adrenergic receptor was last activated, the analgesic α-adrenergic receptor in the absence of α-2A receptor activation over a period of at least three days.

2. The method of claim 1, wherein said pain results from cancer or cancer treatment.

3. The method of claim 1, wherein said pain is inflammatory pain.

4. The method of claim 3, wherein said pain is arthritic pain.

5. The method of claim 3, wherein said pain is irritable bowel syndrome pain.

6. The method of claim 1, wherein said pain is headache pain.

7. The method of claim 1, wherein the analgesic α-adrenergic receptor is activated at least one week after it was last activated.

8. The method of claim 1, wherein the analgesic α-adrenergic receptor is activated at least two week after it was last activated.

9. The method of claim 1, wherein the analgesic α-adrenergic receptor is activated at least three weeks after it was last activated.

10. The method of claim 1, wherein the analgesic α-adrenergic receptor is activated at least four weeks after it was last activated.

11. The method of claim 1, wherein the analgesic α-adrenergic receptor is activated at least one month after it was last activated.

12. A method of relieving chronic pain in a subject, the method comprising the steps of
    administering to the subject over a period of at least three days a composition comprising an effective amount of an α-adrenergic agonist with minimal α-2A agonist activity,
    administering, no sooner than three days after the α-adrenergic agonist was last administered, the α-adrenergic agonist over a period of at least three days.

13. The method of claim 12, wherein the α-adrenergic agonist is administered no sooner than one week after it was last administered.

14. The method of claim 12, wherein the α-adrenergic agonist is administered no sooner than two weeks after it was last administered.

15. The method of claim 12, wherein the α-adrenergic agonist is administered no sooner than three weeks after it was last administered.

16. The method of claim 12, wherein the α-adrenergic agonist is administered no sooner than four weeks after it was last administered.

17. The method of claim 12, wherein the α-adrenergic agonist is administered no sooner than one month after it was last administered.

18. The method of claim 12, wherein the pain is neuropathic pain.

19. The method of claim 12, wherein the pain results from diabetic neuropathy.

20. The method of claim 12, wherein the pain is visceral pain.

21. The method of claim 12, wherein the pain is postoperative pain.

22. The method of claim 12, wherein the pain results from cancer or cancer treatment.

23. The method of claim 12, wherein the pain is inflammatory pain.

24. The method of claim 12, wherein the pain is arthritic pain.

25. The method of claim 12, wherein the pain is irritable bowel syndrome pain.

26. The method of claim 12, wherein the pain is headache pain.

27. The method of claim 12, wherein the α-adrenergic agonist with minimal α-2A agonist activity is an α-2B agonist with minimal α-2A agonist activity.

28. The method of claim 12, wherein the α-2B agonist with minimal α-2A agonist activity is a compound represented by a formula selected from the group consisting of

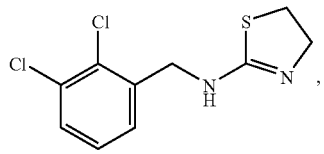
[FORMULA 5]

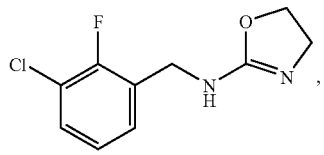
[FORMULA 6]

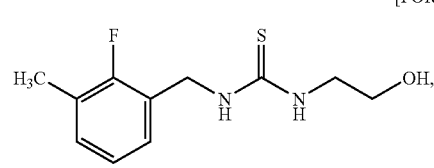
[FORMULA 7]

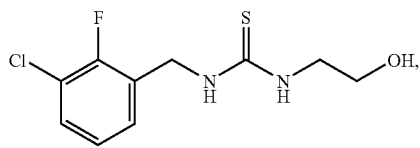
[FORMULA 8]

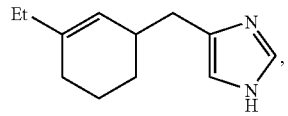
[FORMULA 9]

and all pharmaceutically acceptable salts, esters, am ides, sterioisomers and racemic mixtures thereof.

29. The method of claim 12, wherein the α-adrenergic agonist with minimal α-2A agonist activity is administered peripherally.

30. The method of claim 29, wherein the α-adrenergic agonist with minimal α-2A agonist activity is administered orally.

31. The method of claim 29, wherein the α-adrenergic agonist with minimal α-2A agonist activity is administered through a subcutaneous minipump.

32. A method of relieving chronic pain in a subject, the method comprising the steps of administering to the subject over a period of at least three days a composition comprising an effective amount of an α-adrenergic agonist and an effective amount of a selective α-2A antagonist, administering, no sooner than three days after the α-adrenergic agonist was last administered, the α-adrenergic agonist over a period of at least three days.

33. The method of claim 32, wherein the α-adrenergic agonist is administered no sooner than one week after it was last administered.

34. The method of claim 32, wherein the α-adrenergic agonist is administered no sooner than two weeks after it was last administered.

35. The method of claim 32, wherein the α-adrenergic agonist is administered no sooner than three weeks after it was last administered.

36. The method of claim 32, wherein the α-adrenergic agonist is administered no sooner than four weeks after it was last administered.

37. The method of claim 32, wherein the α-adrenergic agonist is administered no sooner than one month after it was last administered.

38. The method of claim 32, wherein the pain is neuropathic pain.

39. The method of claim 32, wherein the pain results from diabetic neuropathy.

40. The method of claim 32, wherein the pain is visceral pain.

41. The method of claim 32, wherein the pain is postoperative pain.

42. The method of claim 32, wherein the pain results from cancer or cancer treatment.

43. The method of claim 32, wherein the pain is inflammatory pain.

44. The method of claim 32, wherein the pain is arthritic pain.

45. The method of claim 32, wherein the pain is irritable bowel syndrome pain.

46. The method of claim 32, wherein the pain is headache pain.

47. The method of claim 32, wherein the α-adrenergic agonist and selective α-2A antagonist are administered peripherally.

48. The method of claim 47, wherein the α-adrenergic agonist and selective α-2A antagonist are administered orally.

49. The method of claim 47, wherein the α-adrenergic agonist and selective α-2A antagonist are administered through a subcutaneous minipump.

50. The method of claim 32, wherein the α-adrenergic agonist is a pan-α-2 agonist.

51. The method of claim 50, wherein the pan-α-2 agonist is a pan-α-1 pan-α-2 agonist.

52. The method of claim 32, wherein the α-adrenergic agonist is a compound selected from the group consisting of clonidine, brimonidine, tizanidine, dexemedetomidine, norepinephrine, a compound represented by the formula a compound represented by the formula

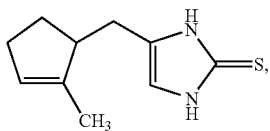
[FORMULA 1]

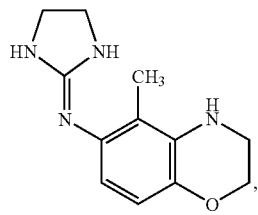
[FORMULA 2]

and all pharmaceutically acceptable salts, esters, amides, sterioisomers and racemic mixtures thereof.

53. The method of claim 32, wherein the selective α-2A antagonist is a 4-imidazole or a pharmaceutically acceptable salt, ester, amide, sterioisomer or racemic mixture thereof.

54. The method of claim 50, wherein the selective α-2A antagonist is a 4-imidazole or a pharmaceutically acceptable salt, ester, amide, sterioisomer or racemic mixture thereof.

55. The method of claim 51, wherein the selective α-2A antagonist is a 4-imidazole or a pharmaceutically acceptable salt, ester, amide, sterioisomer or racemic mixture thereof.

56. The method of claim 52, wherein the selective α-2A antagonist is a 4-imidazole or a pharmaceutically acceptable salt, ester, amide, sterioisomer or racemic mixture thereof.

57. The method of claim 53, wherein the selective α-2A antagonist is a compound represented by the formula

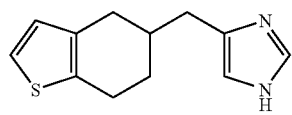
[FORMULA 13]

or a pharmaceutically acceptable salt, ester, amide, sterioisomer or racemic mixture thereof.

58. The method of claim 54, wherein the selective α-2A antagonist is a compound represented by the formula

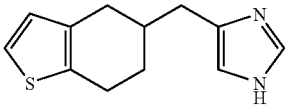
[FORMULA 13]

or a pharmaceutically acceptable salt, ester, amide, sterioisomer or racemic mixture thereof.

59. The method of claim 55, wherein the selective α-2A antagonist is a compound represented by the formula

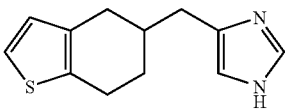
[FORMULA 13]

or a pharmaceutically acceptable salt, ester, amide, sterioisomer or racemic mixture thereof.

60. The method of claim 56, wherein the selective α-2A antagonist is a compound represented by the formula

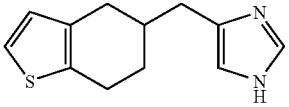
[FORMULA 13]

or a pharmaceutically acceptable salt, ester, amide, sterioisomer or racemic mixture thereof.

* * * * *

UNITED STATES PATENT AND TRADEMARK OFFICE
CERTIFICATE OF CORRECTION

PATENT NO. : 7,345,065 B2
APPLICATION NO. : 10/153154
DATED : March 18, 2008
INVENTOR(S) : Gil et al.

It is certified that error appears in the above-identified patent and that said Letters Patent is hereby corrected as shown below:

In column 6, line 19, after "such" delete "a" and insert -- as --, therefor.

In column 8, line 36, after "distension" insert -- . --.

In column 9, line 5, delete "norephinephrine" and insert -- norepinephrine --, therefor.

In column 9, line 30, delete "Artinano," and insert -- Artiñano --, therefor.

In column 15, line 38, delete "α-1" and insert -- α-1B --, therefor.

In column 22, line 2, after "such" delete "a" and insert -- as --, therefor.

In column 22, line 42, delete "herein,"" and insert -- herein, --, therefor.

In column 24, line 11, delete "$C_1$ to $C_7$" and insert -- $C_5$ to $C_7$ --, therefor.

In column 24, line 47, after "example, an" delete "an".

In column 35, line 43, delete "34w)." and insert -- 34%). --, therefor.

In column 35, line 52, delete "-14." and insert -- ~14. --, therefor.

In column 36, line 26, delete "CDC13" and insert -- $CDCl_3$ --, therefor.

In column 36, line 32, delete "α2-A" and insert -- α-2A --, therefor.

In column 37, line 24, delete "bioavailablility" and insert -- bioavailability --, therefor.

In column 40, line 11, delete "β2-B/C" and insert -- α2-B/C --, therefor.

In column 41, line 24, delete "α-2-A" and insert -- α-2A --, therefor.

In column 41, line 47, delete "α2-A" and insert -- α-2A --, therefor.

In column 43, line 40, delete "L igatures" and insert -- Ligatures --, therefor.

In column 44, line 50, delete "α2-A" and insert -- α-2A --, therefor.

In column 44, line 54, delete "α2-A" and insert -- α-2A --, therefor.

UNITED STATES PATENT AND TRADEMARK OFFICE
CERTIFICATE OF CORRECTION

PATENT NO. : 7,345,065 B2
APPLICATION NO. : 10/153154
DATED : March 18, 2008
INVENTOR(S) : Gil et al.

It is certified that error appears in the above-identified patent and that said Letters Patent is hereby corrected as shown below:

In column 44, line 56, delete "α2-A" and insert -- α-2A --, therefor.

In column 49, line 56, in Claim 28, delete "am ides," and insert -- amides, --, therefor.

In column 51, line 23, in Claim 52, delete "am ides," and insert -- amides, --, therefor.

Signed and Sealed this

First Day of July, 2008

JON W. DUDAS
*Director of the United States Patent and Trademark Office*